(12) United States Patent
Marsais et al.

(10) Patent No.: US 7,977,354 B2
(45) Date of Patent: Jul. 12, 2011

(54) HETEROCYCLIC COMPOUNDS, THEIR PREPARATION AND THEIR USE AS MEDICAMENTS, IN PARTICULAR AS ANTI-ALZHEIMER AGENTS

(75) Inventors: Francis Marsais, Rouen (FR); Pierre Bohn, Sotteville les Rouen (FR); Vincent Levacher, Bois-Guillaume (FR); Nicolas Le Fur, Rouen (FR)

(73) Assignees: Insa Rouen, Cedex (FR); Gous Inc., Quebec (CA)

( * ) Notice: Subject to any disclaimer, the term of this patent is extended or adjusted under 35 U.S.C. 154(b) by 297 days.

(21) Appl. No.: 11/909,911

(22) PCT Filed: Mar. 29, 2006

(86) PCT No.: PCT/EP2006/003787
§ 371 (c)(1),
(2), (4) Date: Jul. 16, 2008

(87) PCT Pub. No.: WO2006/103120
PCT Pub. Date: Oct. 5, 2006

(65) Prior Publication Data
US 2009/0062279 A1     Mar. 5, 2009

(30) Foreign Application Priority Data

Apr. 1, 2005   (EP) .................................. 05290719
Apr. 26, 2005  (EP) .................................. 05290914

(51) Int. Cl.
*A01N 43/40* (2006.01)
*A61K 31/47* (2006.01)
*A61K 31/44* (2006.01)
*C07D 215/00* (2006.01)

(52) U.S. Cl. ........ 514/311; 514/314; 514/356; 546/152; 546/165

(58) Field of Classification Search .................. 514/311, 514/314, 356; 546/152, 165
See application file for complete search history.

(56) References Cited

U.S. PATENT DOCUMENTS 5,714,615 A    2/1998 Powers et al.

FOREIGN PATENT DOCUMENTS

| EP | 0354994 A2 | 2/1990 |
| WO | 9708146 A | 3/1997 |
| WO | 02094833 A | 11/2002 |

OTHER PUBLICATIONS

Wuest, HM. et al. Some Derivatives of 3-Pyridol with Parasympathomimetic Properties. Journal of the American Chemical Society. vol. 73. 1951. pp. 1210-1216. XP002348929.

Wang, J-Q et al. Facile synthesis and initial PET imaging of novel potential heart acetylcholinesterase imaging agents [11C]pyridostigmine and its analogs. Nuclear Medicine and Biology. Elsevier Science Publishers. New York, NY, US. vol. 31. No. 7. 2004. pp. 957-964. XP004587529. ISSN: 0969-0851.

Mishra, NN et al. Highly Sensitive Assay for Anticholinesterase Compounds Using 96 Well Plate Format. ACS Symposium Series. Washington, DC, US. vol. 806. 2002. pp. 289-305. XP009033032, ISSN: 0097-06156.

Radic, Z et al. Expression of Recombinant Acetylcholinesterase in a Baculovirus System: Kinetic Properties of Glutamate 199 Mutants. Biochemistry, American Chemical Society. Easton, PA, US. vol. 31. 1992. pp. 9760-9767. XP001040344. ISSN: 006-2960.

Badawi, AM et al. New Quaternary Carbamates. Oriental Journal of Chemistry. Iqbal, Bhopal, IN. vol. 4. No. 1. 1988. pp. 76-83. XP009060208. ISSN: 0970-020X.

Kitz, RJ et al. The reaction of acetylcholinesterase with o-dimethylcarbamyl esters of quatenary quinolinium compounds. Biochemical Pharmacology. Pergamon, Oxford, GB. vol. 16. 1967. pp. 2201-2209. XP002367405. ISSN: 0006-252.

*Primary Examiner* — San-Ming Hui
*Assistant Examiner* — Paul Zarek
(74) *Attorney, Agent, or Firm* — Leslie S. Craig

(57) ABSTRACT

The invention is related to compound which comprises at least one radical C=Y, Y being O or S, and an oxidable and non protonable nitrogen atom N wherein the distance (d) between the at least one carbon atom of the radical group C=Y and the nitrogen atom, when oxidized, is comprised between 0.3 and 0.8 nanometers. The invention is related to new heterocyclic compounds defined by formula G, their preparation, to pharmaceutical compositions comprising them and to their use as therapeutic agents, particularly in the treatment of neurodegenerative or Alzheimer disease.

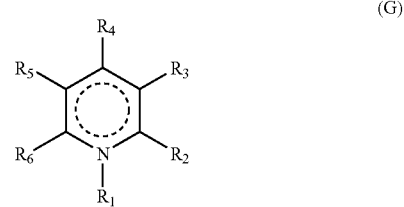

(G)

18 Claims, No Drawings

HETEROCYCLIC COMPOUNDS, THEIR PREPARATION AND THEIR USE AS MEDICAMENTS, IN PARTICULAR AS ANTI-ALZHEIMER AGENTS

FIELD OF THE INVENTION

The invention relates to new heterocyclic compounds, their preparation, to pharmaceutical compositions comprising them and to their use as therapeutic agents, particularly in the treatment of neurodegenerative or Alzheimer disease.

BACKGROUND OF THE INVENTION

The present invention relates to the prevention, treatment and amelioration of neurodegenerative or Alzheimer's disease, and more particularly to the prevention, treatment and amelioration of Alzheimer's disease with new heterocyclic compounds which act as inhibitors of central cholinesterase enzyme following the indirect cholinomimetic pathway described in the following bibliographic references:
1)—Kasa P, Rakonczay Z, Gulya K. The cholinergic system in Alzheimer's disease. Prog Neurobiol. 1997 August; 52(6):511-35.
2)—Francis P T, Palmer A M, Snape M, Wilcock G K. The cholinergic hypothesis of Alzheimer's disease: a review of progress.
3)—Davies P, Maloney A J F. Selective loss of central cholinergic neurones in Alzheimer's Disease. Lancet. 1976; ii: 1403.
4)—Bartus R. T., Dean R. L., Beer B and Lippa A. S. The cholinergic hypothesis of geriatric memory dysfunction. Science 1982; 217: 408-17.
5)—Taylor P. Development of acetylcholinesterase inhibitors in the therapy of Alzheimer's Disease. Neurology 1998; 51(1): S30-S35

Alzheimer's disease (AD) is characterised by a progressive, inexorable loss of cognitive function associated with an excessive number of senile plaques in the cerebral cortex and subcortical gray matter, which also contains amyloid and neurofibrillary tangles consisting of tau protein. While early-onset forms of AD account for 2%-7% of cases, the common form affects persons greater than 60 years old, and its incidence increases as age advances. Million of humans have AD, and the annual cost of the disease is very high.

Some pyridinium or quinolinium carbamate derivatives have been disclosed as acetylcholineserase inhibitors in WO97/08146; in Wuest & al JACS vol 73, 1951 p. 1210-1216; in Wang & al nuclear medicine and biology vol 31, no. 7 October. 2004, p. 957-964; in Mishra & al ACS symposium series vol 806, 2002, p. 289-306; in Radio & al Biochemistry, vol 31, 1992, p. 9760-9767; in Badwi & al Oriental J. of Chemistry, vol 4, no. 1, 1988, p. 76-83; and in Kitz & al Biochemical Pharmacology vol 16, 1967, p. 2201-2209. Nevertheless these compounds present the drawback of being unstable in vivo and very rapidly desactivated.

Today, only few cholinesterase inhibitors agents are known and used as a drug for the treatment of AD. These agents are Donepezil (1), Galantamine (2) and Rivastigmine (3). However the major drawback with these molecules is the loss of their therapeutical effect with time.

Thus the need of increasing the daily doses increases the side effects, until the interruption of the treatment. It is known that these side effects are specifically caused by the peripheral activity of these molecules on cholinesterase enzyme.

There is a need for new cholinesterase inhibitors agent which could act against neurodegenerative diseases. There is a need for anti Alzheimer molecules which decrease or avoid the side effects of the known commercial drugs. Specifically there is a need for new compounds which could act as anti-Alzheimer agents without interacting with peripheral cholinesterase enzyme.

SUMMARY OF THE INVENTION

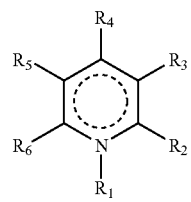

G

The present invention relates to compound of formula G wherein:
the dotted circle line represents one double bond between $CR_5$-$CR_6$, and another double bond between either $CR_2$-$CR_3$ or $CR_3$-$CR_4$; and either
a) $R_1$ $R_2$ $R_3$ $R_4$ $R_5$ $R_6$ which may be identical or different are hydrogen, OH, ($C_1$-$C_8$)alkyl, aryl, heteroaryl, ($C_1$-$C_8$) alkylaryl, aryl ($C_1$-$C_8$)alkyl, alkoxy, hydroxy ($C_1$-$C_8$) alkyl, alkoxy ($C_1$-$C_8$)alkyl, phenyl, $(CH_2)_n$—COOH, Z, $Z_1$; or
b) $R_4$ and $R_5$ or c) $R_5$ and $R_6$ taken together with the carbon atoms to which they are attached form a 6-membered aromatic ring or form a 5- or 6-membered heterocyclic ring being optionally substituted by one or more group, identical or different, defined as OH, ($C_1$-$C_8$) alkyl, aryl, heteroaryl, ($C_1$-$C_8$)alkylaryl, aryl ($C_1$-$C_8$)alkyl, alkoxy, hydroxy ($C_1$-$C_8$)alkyl, alkoxy ($C_1$-$C_8$)alkyl, phenyl, $(CH_2)_n$—COOH, Z, $Z_1$; and in all case a) and b) and c);
at least one group among $R_2$ $R_3$ $R_5$ is an electron withdrawing group selected from the group comprising COOR, COSR, CONRR', CN, COR, $CF_3$, SOR, $SO_2R$, SONRR', $SO_2NRR'$, $NO_2$, halogen, heteroaryl, wherein
R, R' being a group H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenalkyl, thioalkyl, thioalkoxyalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached form an heterocyclic ring of at least 3 members, preferably a 5 or 6 membered heterocyclic ring, optionally substituted by one or more groups being as defined for $R_2$, or R and R' taken together with the nitrogen atom to which they are attached form a fused polyheterocyclic system preferably tetrahydroisoquinoline, indoline, isoindoline, optionally substituted by one or more group being as defined for $R_2$;

and wherein
Z is a group defined by formula -(L)$_m$-$Z_1$, L is ($C_1$-$C_8$)alkyl, aryl, heteroaryl, phenyl, ($C_1$-$C_8$) alkylaryl, aryl($C_1$-$C_8$) alkyl;

$Z_1$ is defined by formula

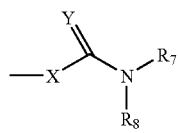

wherein X, Y is O, S; $R_7$, $R_8$ which may be identical or different are hydrogen, ($C_1$-$C_8$) alkyl, aryl, heteroaryl, ($C_1$-$C_8$)alkylaryl, phenyl, cyclopropyl, $(CH_2)_n$—COOH; and wherein n and m are an integer $\geq 1$, preferably m is comprised between 1 and 4 and n is comprised between 1 and 6;

and provided that at least one group $R_1$ $R_2$ $R_3$ $R_4$ $R_5$ or $R_6$ is Z or $Z_1$ and that $R_1$ is not H or $Z_1$;

or a pharmaceutical salts or a stereoisomer thereof.

Another object of the invention is a compound according to claim 1 of formula G⁺

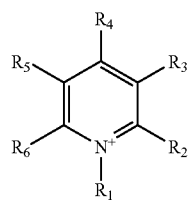

G⁺ optionally under a ammonium salt form G⁺W⁻ wherein W is the leaving group of an alkylating agent of formula $R_1$—W or under a pharmacological acceptable salt.

In a preferred embodiment the invention is related to a compound of formula G1a or G1b or G1⁺

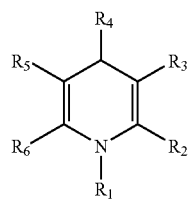

G1a

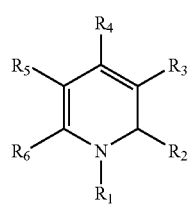

G1b

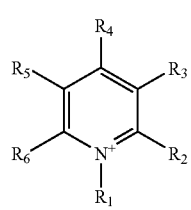

G1+ wherein $R_1$ $R_2$ $R_3$ $R_4$ $R_5$ $R_6$ have the same meaning as defined above. In another preferred embodiment $R_3$ or $R_5$ is an electron withdrawing group, or $R_3$ and $R_5$ are both an electron withdrawing group.

In a preferred embodiment the invention is related to a compound of formula G2 or G2⁺

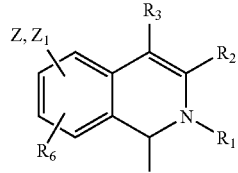

G2

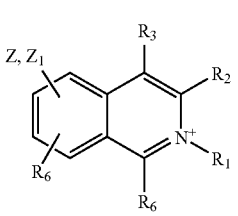

G2+ wherein $R_1$ $R_2$ $R_3$ $R_4$ $R_5$ $R_6$ Z, $Z_1$ have the same meaning as defined above In another preferred embodiment $R_2$ or $R_3$ is an electron withdrawing group, or $R_2$ and $R_3$ are both an electron withdrawing groups.

In a preferred embodiment the invention is related to a compound of formula G3a or G3b or G3⁺

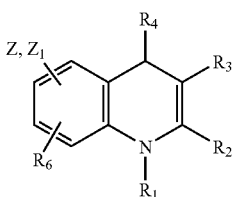

G3a

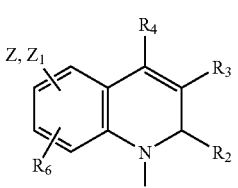

G3b

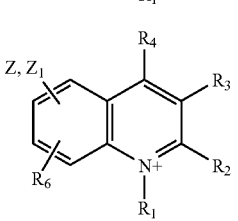

G3+ wherein $R_1$ $R_2$ $R_3$ $R_4$ $R_5$ $R_6$ Z, $Z_1$ have the same meaning as defined above. In another preferred embodiment $R_3$ is an electron withdrawing group.

In a preferred embodiment the invention is related to a compound G1a or G1b or G1+ as defined above wherein
a) $R_2$ and $R_3$ or $R_3$ and $R_4$ taken together with the carbon atoms to which they are attached form a 5 to 7 membered heterocycle, preferably selected from lactame, N-alkyllactame, N-aryllactame, N-heteroaryllactame, lactone, thiolactone; or b) $R_1$ and $R_6$ or $R_1$ and $R_2$ taken together with the atoms to which they are attached form a 5 to 7 membered heterocycle, optionally substituted by one or more groups being as defined above for $R_2$.

In a preferred embodiment the invention is related to a compound G2 or G2+ as defined above wherein a) $R_2$ and $R_3$ taken together with the carbon atoms to which they are attached form a 5 to 7 membered heterocycle, preferably selected from lactame, N-alkyllactame, N-aryllactame, N-heteroaryllactame, lactone, thiolactone; or b) $R_1$ and $R_6$ taken together on the same cycle or $R_1$ and $R_2$ taken together with the atoms to which they are attached form a 5 to 7 membered heterocycle optionally substituted by one or more group being as defined above for $R_2$.

In a preferred embodiment the invention is related to a compound G3a or G3b or G3+ as defined above a) $R_2$ and $R_3$ or $R_3$ and $R_4$ taken together with the carbon atoms to which they are attached form a 5 to 7 membered heterocycle, preferably selected from lactame, N-alkyllactame, N-aryllactame, N-heteroaryllactame, lactone, thiolactone; or b) $R_1$ and $R_6$ or $R_1$ and $R_2$ taken together with the atoms to which they are attached form a 5 to 7 membered heterocycle optionally substituted by one or more groups being as defined above for $R_2$.

In a more preferred embodiment the invention is related to a compound G3a or G3+ wherein $R_1$ is $(C_1-C_4)$alkyl, $R_2$ is H, $(C_1-C_4)$alkyl, $R_3$ is an electron withdrawing group as defined above, $R_4$ and $R_6$ is H, $Z_1$ is $OCONR_7R_8$, $R_7$ $R_8$ being as defined above.

In another embodiment the invention is related to a compound of formula G or G+ as defined above wherein $R_3$ is a heteroaryl group selected among oxazolinyl, thiazolinyl, oxazolyl, thiazolyl, triazolyl or tetrazolyl optionally substituted by one or more groups being as defined above for $R_2$.

In another embodiment the invention is related to a compound of formula G or G+ as defined above wherein $R_1$ is $(C_1-C_4)$alkyl, $-(L)_m-Z_1$ wherein L is aryl, m is 1; $R_2$ is H, $(C_1-C_4)$ alkyl, phenyl, aryl;

$Z_1$ is

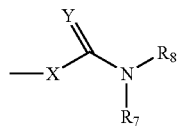

wherein X and Y are O, or X is O and Y is S or X is S and Y is O; $R_7$, $R_8$ which may be identical or different are hydrogen, $(C_1-C_4)$alkyl or $(C_1-C_4)$alkylaryl or phenyl.

Another object of the invention is the compound as defined above and comprising at least one radical C=Y, Y being O or S, and an oxidable and non protonable nitrogen atom N wherein the distance d between the at least one carbon atom of the radical group C=Y and the nitrogen atom, when oxidized, is comprised between 0.3 and 0.8 nanometers, preferably 0.4 and 0.7 nanometers.

Another object of the invention is the compound as defined above which is an acetylcholinesterase inhibitor, at least 500, preferably at least 1000 times more active in central nervous system CNS than in peripheral nervous system PNS. In a specific embodiment the compound is an acetylcholinesterase inhibitor, at least 500, preferably at least 1000 times more active in central nervous system CNS under its oxidized form than in peripheral nervous system PNS under its non oxidized form.

Another object of the invention is the compound of formula G or G+ as defined above, the names of which follow;

1. Ethyl 1-methyl-7-(N,N-dimethylcarbamate)-1,4-dihydroquinoline-3-carboxylate;
2. Ethyl 1-methyl-5-(N,N-dimethylcarbamate)-1,4-dihydroquinoline-3-carboxylate;
3. Ethyl 1-methyl-5,7-di(N,N-dimethylcarbamate)-1,4-dihydroquinoline-3-carboxylate;
4. Ethyl 1-methyl-5,8-di(N,N-dimethylcarbamate)-1,4-dihydroquinoline-3-carboxylate;
5. Ethyl 1-methyl-5-(N,N-dimethylthiocarbamate)-1,4-dihydro-5-O-quinoline-3-carboxylate;
6. Ethyl 1-methyl-5-(N,N-dimethylthiocarbamate)-1,4-dihydro-5-S-quinoline-3-carboxylate;
7. 1-Methyl-5-(N,N-dimethylcarbamate)-3-(N,N-diethylcarboxamido)-1,4-dihydroquinoline;
8. 1-Methyl-7-(N,N-dimethylcarbamate)-3-(4,5-dihydro-4,4-dimethyl-2-oxazolyl)-1,4-dihydroquinoline;
9. 1-Methyl-5-(N,N-dimethylcarbamate)-3-trifluoromethyl-1,4-dihydroquinoline;
10. (+/−)-1-Methyl-3-(4-methylphenylsulfinyl)-5-(N,N-dimethylcarbamate)-1,4-quinoline;
11. 1-Methyl-3-(4-methylphenylsulfonyl)-5-(N,N-dimethylcarbamate)-1,4-dihydroquinoline;
12. 1-Methyl-5-(N,N-dimethylcarbamate)-3-(N-phenylsulfomanide)-1,4-dihydroquinoline;
13. 1-Methyl-6,7-di(N,N-dimethylcarbamate)-3-nitro-1,4-dihydroquinoline;
14. Ethyl 1-methyl-2-phenyl-6,7-di(N,N-dimethylcarbamate)-1,4-dihydroquinoline-3-carboxylate;
15. Ethyl 1,2,4-trimethyl-7-(N,N-dimethylcarbamate)-1,4-dihydroquinoline-3-carboxylate;
16. 2-Methyl-7-(N,N-dimethylcarbamate)-1,2-dihydroisoquinoline;
17. 2-Methyl-7-(N,N-dimethylthiocarbamate)-1,2-dihydro-7-O-isoquinoline;
18. 2-Methyl-7-(N,N-dimethylthiocarbamate)-1,2-dihydro-7-S-isoquinoline;
19. 1,2-Dimethyl-7-(N,N-dimethylthiocarbamate)-1,2-dihydro-7-O-isoquinoline;
20. Ethyl 2,3-dimethyl-6,8-di(N,N-dimethylcarbamate)-1,2-dihydroisoquinoline-4-carboxylate;
21. 2,3-Dimethyl-6,8-di(N,N-dimethylcarbamate)-1,2-dihydroisoquinoline-4-carboxamide;
22. 2,3-Dimethyl-4-(4,5-dihydro-4,4-dimethyl-2-oxazolyl)-6,8-di(N,N-dimethylcarbamate)-1,2-dihydroisoquinoline;
23. (+/−)-2,3-Dimethyl-4-(4-methylphenylsulfinyl)-6,8-di(N,N-dimethylcarbamate)-1,2-dihydroisoquinoline;
24. 2,3-Dimethyl-4-(methylphenylsulfonyl)-6,8-di(N,N-dimethylcarbamate)-1,2-dihydroisoquinoline;
25. 2,3-Dimethyl-4-(N-phenylsulfonamide)-6,8-di(N,N-dimethylcarbamate)-1,2-dihydroisoquinoline;
26. 2,3-Dimethyl-4-(trifluoromethyl)-6,8-di(N,N-dimethylcarbamate)-1,2-dihydroisoquinoline;
27. Ethyl 1-methyl-5-(N,N-dimethylcarbamate)-1,4-dihydropyridine-3-carboxylate
28. Ethyl 1-methyl-5-(N,N-dimethylthiocarbamate)-1,4-dihydro-5-O-pyridine-3-carboxylate;
29. Ethyl 1-methyl-5-(N,N-dimethylthiocarbamate)-1,4-dihydro-5-S-pyridine-3-carboxylate;
30. 1-Methyl-3-(methylsulfonyl)-5-(N,N-dimethylcarbamate)-1,4-dihydropyridine;

31. 1-Methyl-3-(N,N-diethylcarboxamido)-5-(N,N-dimethylcarbamate)-1,4-dihydropyridine;
32. (+/−)-1-Methyl-3-(methylsulfinyl)-5-(N,N-dimethylcarbamate)-1,4-dihydropyridine;
33. 1-Methyl-3-(trifluoromethyl)-5-(N,N-dimethylcarbamate)-1,4-dihydropyridine;
34. 1-Methyl-3-(4,5-dihydro-4,4-dimethyl-2-oxazolyl)-5-(N,N-dimethylcarbamate)-1,4-dihydropyridine;
35. N,N-Diethyl-1-methyl-5-(N,N-dimethylcarbamate)-1,4-dihydro-3-pyridinesulfonamide;
36. Ethyl 1-[2-(N,N-dimethylcarbamate)benzyl]-1,4-dihydropyridine-3-carboxylate;
37. 1-[2-(N,N-dimethylcarbamate)benzyl]-3-(methylcarbamoyl)-1,4-dihydropyridine;
38. 1-[2-(N,N-dimethylcarbamate)benzyl]-3-(4,5-dihydro-4,4-dimethyl-2-oxazolyl)-1,4-dihydropyridine;
39. N,N-Diethyl-1-[2-(N,N-dimethylcarbamate)benzyl]-1,4-dihydropyridine-3-sulfonamide;
40. Ethyl 1-[2-(N,N-dimethylcarbamate)benzyl]-1,4-dihydroquinoline-3-carboxylate;
41. 1-[2-(N,N-dimethylcarbamate)benzyl]-1,4-dihydro-3-(dimethylcarbamoyl)quinoline;
42. 1-[2-(N,N-dimethylcarbamate)benzyl]-1,4-dihydro-3-(4,5-dihydro-4,4-dimethyl-2-oxazolyl)quinoline;
43. N,N-Dimethyl-1-[2-(N,N-dimethylcarbamate)benzyl]-1,4-dihydroquinoline-3-sulfonamide;
44. Ethyl 2-[2-(N,N-dimethylcarbamate)benzyl]-1,2-dihydroisoquinoline-4-carboxylate;
45. 2-[2-(N,N-dimethylcarbamate)benzyl]-4-(N-phenethylcarbamoyl)-1,2-dihydroisoquinoline;
46. 2-[2-(N,N-dimethylcarbamate)benzyl]-4-(4,5-dihydro-4,4-dimethyl-2-oxazolyl)-1,2-dihydroisoquinoline;
47. N,N-diethyl-2-[2-(N,N-dimethylcarbamate)benzyl]-1,2-dihydroisoquinoline-4-sulfonamide;
48. 1-[2-(N,N-dimethylcarbamate)benzyl]-3-(trifluoromethyl)-1,4-dihydropyridine;
49. 1-[2-(N,N-dimethylcarbamate)benzyl]-3-(trifluoromethyl)-1,4-dihydroquinoline;
50. 1-[2-(N,N-dimethylcarbamate)benzyl]-3-(trifluoromethyl)-1,2-dihydroisoquinoline;
51. Ethyl 1-methyl-2-[2-(N,N-dimethylcarbamate)phenyl]-1,4-dihydropyridine-3-carboxylate;
52. 1-Methyl-2-[2-(N,N-dimethylcarbamate)phenyl]-1,4-dihydro-N, N-dimethylnicotinamide;
53. 1-Methyl-2-[2-(N,N-dimethylcarbamate)phenyl]-3-(methylsulfonyl)-1,4-dihydropyridine;
54. N-Methyl 1-methyl-2-[2-(N,N-dimethylcarbamate)phenyl]-1,4-dihydropyridine-3-sulfonamide;
55. Ethyl 1-methyl-6-[2-(N,N-dimethylcarbamate)phenyl]-1,4-dihydropyridine-3-carboxylate;
56. Ethyl 1-methyl-5-[2-(N,N-dimethylcarbamate)phenyl]-1,4-dihydropyridine-3-carboxylate;
57. Ethyl 1-methyl-2-[2-(N,N-dimethylcarbamate)phenyl]-1,4-dihydroquinoline-3-carboxylate;
58. Ethyl 1-methyl-8-[2-(N,N-dimethylcarbamate)phenyl]-1,4-dihydroquinoline-3-carboxylate;
59. 1-[2-(N,N-dimethylcarbamate)phenyl]-2-methyl-1,2-dihydroisoquinoline;
60. 2-Methyl-4-[2-(N,N-dimethylcarbamate)phenyl]-1,2-dihydroisoquinoline;
61. Ethyl 1-methyl-7-(N,N-dimethylcarbamate)-1,2-dihydroquinoline-3-carboxylate;
62. Ethyl 1-methyl-5-(N,N-dimethylthiocarbamate)-1,2-dihydro-5-S-quinoline-3-carboxylate;
63. 1-Methyl 5-(N,N-dimethylcarbamate)-3-(4,5-dihydro-4,4-dimethyl-2-oxazolyl) 1,2-dihydroquinoline;
64. Ethyl 1-methyl-5-(N,N-dimethylcarbamate)-1,2-dihydropyridine-3-carboxylate;
65. Ethyl 1-methyl-5-(N,N-dimethylthiocarbamate)-1,2-dihydro-5-S-pyridine-3-carboxylate;
66. 1-Methyl-3-(N,N-diethylcarboxamido)-5-(N,N-dimethylcarbamate)-1,2-dihydropyridine;
67. Methyl 1-methyl-5-(N,N-dimethylcarbamate)-1,4-dihydroquinoline-3-carboxylate;
68. 1-Methyl-3-(N-methylcarboxamido)-5-(N,N-dimethylcarbamate)-1,4-dihydroquinoline;
69. [3-(N,N-methylcarboxamido)-5-(N,N-dimethylcarbamate)]-1,4-dihydroquinoline or 1,2-dihydroquinoline;
70. Morpholine 4-[1-methyl-5-(N,N-dimethylcarbamate)-1,4-dihydroquinolyl-3-carbonyl];
71. 2-Methyl-5-(N,N-dimethylcarbamate)-1,2-dihydroisoquinoline;
72. 2-Methyl-7-(N,N-dimethylcarbamate)-1,2-dihydroisoquinoline;
73. [Methyl 1-methyl-5,7-bis(N,N-dimethylcarbamate)-3-carboxylate]-1,4-dihydroquinoline or 1,2-dihydroquinoline;
74. [Methyl 1-methyl-8-(N,N-dimethylcarbamate)-3-carboxylate]-1,4-dihydroquinoline or 1,2-dihydroquinoline;
75. 2-methyl-5-(N,N-dimethylthiocarbamate)-O-1,2-dihydroisoquinoline;
76. Methyl 1-methyl-5-(N-ethylcarbamate)-1,4-dihydroquinoline-3-carboxylate;
77. [Ethyl 1-methyl-8-(N,N-dimethylcarbamate)-3-carboxylate]-1,4-dihydroquinoline or 1,2-dihydroquinoline;
78. 1-Methyl-3-(N-propylcarboxamido)-7-(N,N-dimethylcarbamate)-1,4-dihydroquinoline;
79. [Ethyl 1-methyl-5-(N,N-dimethylcarbamate)-3-carboxylate]-1,4-dihydropyridine;
80. Ethyl 1-[4-(N,N-dimethylcarbamate)benzyl)]pyridinium-3-carboxylate iodide;

or their corresponding ammonium form thereof.

Another object of the invention is an inclusion complex of a compound as defined above and of formula G, G1a, G1b, G2, G3a, G3b with a beta-cyclodextrine, preferably an hydroxypropyl-betacyclodextrine.

Another object of the invention is a pharmaceutical composition comprising at least one compound as defined above and a pharmacologically acceptable carrier, for its use as an acetylcholinesterase inhibitor in the CNS.

According to another object, the pharmaceutical composition is used in the treatment of neurodegenerative diseases, preferably Alzheimer's disease in a human or other animal subject.

Another object of the invention is a pharmaceutical composition comprising a compound of formula $G^+$, $G1^+$, $G2^+$ or $G3^+$ as defined above for its use as acetylcholinesterase inhibitor in the PNS, for its use in the treatment of myasteny disease in a human or other animal subject.

Another object of the invention is the use of a safe and effective amount of a compound of any one of formula G, G1a, G1b, G2, G3a, G3b as defined above for the manufacture of a prodrug for the treatment of disorders associated to neurodegenerative diseases in a human or other animal subject, wherein said treatment comprises administering said prodrug to said subject.

Another object of the invention is the use of a safe and effective amount of a compound of any one of formula G+, G1+, G2+, G3+ as defined above for the manufacture of a drug for the treatment of disorders associated to neurodegenerative diseases in a human or other animal subject, wherein said treatment comprises delivering said drug to the PNS of said subject.

Another object of the invention is a compound comprising at least one radical C=Y, Y being O or S, and an oxidable and non protonable nitrogen atom N wherein the distance (d) between the at least one carbon atom of the radical group C=Y and the nitrogen atom, when oxidized, is comprised between 0.3 and 0.8 nanometers, preferably between 0.4 and 0.7 nm.

In a preferred embodiment, the compound further comprises at least one electron withdrawing group in alpha or beta position to the oxidized nitrogen atom.

In a more preferred embodiment, the compound comprises one electron withdrawing group in beta position to the oxidized nitrogen atom.

In a specific embodiment, the at least one radical C=Y belongs to a carbamate or a thiocarbamate radical.

Another object of the invention is a compound which is an acetylcholinesterase inhibitor, at least 500, preferably at least 1000 times more active in central nervous system CNS than in peripheral nervous system PNS.

Another object of the invention is a compound which is an acetylcholinesterase inhibitor, at least 500 or at least 1000 times more active in central nervous system CNS under its oxidized form than in peripheral nervous system PNS under its non oxidized form.

Another object of the invention is an inclusion complex of a compound as above with a beta-cyclodextrine, preferably an hydroxypropyl-betacyclodextrine.

Another object of the invention is a pharmaceutical composition comprising at least one compound as defined above and a pharmacologically acceptable carrier.

Another object of the invention is the pharmaceutical composition defined above for its use as an acetylcholinesterase inhibitor in the CNS.

Another object of the invention is a compound of the following formula G'1, G'2, and G'3;

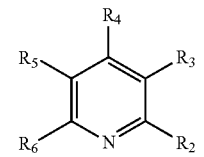

G'1

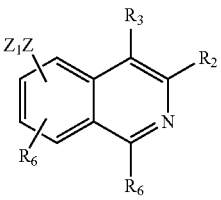

G'2

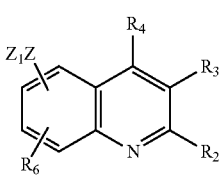

G'3 wherein $R_2$ $R_3$ $R_4$ $R_5$ $R_6$ Z, $Z_1$ are as defined above.

Another object of the invention is a process for the preparation of a compound of formula G, G1a, G1b, G2, G3a, G3b, as defined above which comprises the step of reduction of a compound of formula ($G^+$ or $G_i^+$) $W^-$ i being 1, 2 or 3, in the presence of a reducing agent.

Another object of the invention is a process for the preparation of a compound of formula ($G^+$ or $G_i^+$)$W^-$ i being 1, 2 or 3 as defined above, which comprises a step of quaternization of the nitrogen atom of a compound of formula G'1, G'2, G'3 as defined above, by an alkylating agent $R_1$—W, $R_1$ being $(C_1-C_8)$alkyl, aryl, $(C_1-C_8)$alkylaryl, aryl$(C_1-C_8)$alkyl, alkoxy, hydroxy$(C_1-C_8)$alkyl, alkoxy$(C_1-C_8)$alkyl, phenyl, $(CH_2)_n$—COOH; W being a leaving group, preferably selected from halogen, O-triflate, carboxylate, sulfate, tosylate, mesylate.

Another object of the invention is a process for the preparation of a compound of formula G'1, G'2, G'3 as defined above which comprises a step of carbamoylation of a compound of the following formula E1 or E2 or E3

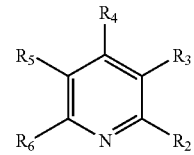

E1

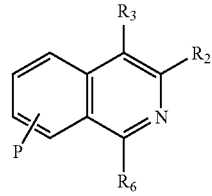

E2

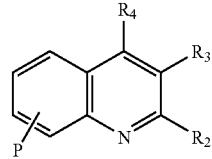

E3 wherein P is OH, $(L)_m$ OH and at least one $R_5$ or $R_6$ in formula E1 is OH or $(L)_m$ OH; with an agent of formula W'—Z or W'—$Z'_1$, wherein Z'1 is

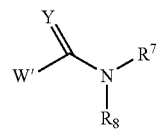

and W' is a leaving group, preferably selected from halogen, O-triflate, sulfate, tosylate, mesylate and $R_2$ $R_3$ $R_4$ $R_5$ L, m, Y, $R_7$, $R_8$ have the same meaning as defined above.

Another object of the invention is a process for the preparation of compound of formula $G^+W$ or $G_i^+$ $W^-$ i being 1, 2 or 3 as defined above and with $R_1$ being Z, which comprises a step of quaternization of a compound of the formula E1, E2 or E3

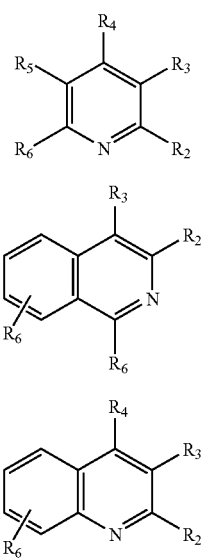

E1

E2

E3 with an alkylating agent bearing a carbamate group of formula W—Z, and $R_2$ $R_3$ $R_4$ $R_5$, $R_6$, Z and W have the same meaning as defined above.

DETAILED DESCRIPTION

One object of the invention is a compound which should be considered as a prodrug when it is in its oxidable and non protonable or neutral nitrogen form. This prodrug has no activity against central or peripheral acetylcholinesterase, because the oxidable nitrogen atom is non protonable at physiological pH.

This prodrug comprises at least one an electron withdrawing group (EWG). This EWG is in alpha or beta position to the nitrogen atom. Thus the presence of the EWG increases the stability of the final compound of formula G. Moreover the ability of the uncharged or oxidable nitrogen of being non protonable is enhanced by the presence in the compound of the invention of this electron withdrawing group (EWG) which draws electrons away from a reaction center. In a preferred embodiment, this EWG is in beta position to the nitrogen atom and thus allows the delocalisation of the nitrogen electronic doublet. This results in a non protonable compound with a enhanced stability in vivo and specifically in the PNS before the passage through the BBB towards the CNS.

Indeed, in its neutral form only, this prodrug is able to go from the blood to the central nervous system (CNS) through the blood brain barrier (BBB).

Then in vivo, in the CNS, the prodrug is converted into its oxidized form and the resultant charged form named drug, is active for action Indeed, once oxidized, the prodrug is transformed into a cholinesterase inhibitor because the distance d between the at least one carbon atom of the radical group C=Y and the oxidized $N^+$ atom is comprised between 0.3 and 0.8 nanometers. This distance allows the compound to be in the suitable form to block the active site of the central acetylcholinesterase.

In fact, due to the presence of the oxidized $N^+$ group and the radical group C=Y which belongs to a carbamate or thiocarbamate derivative, the compounds of the invention will be inserted in the active site of the enzyme and recognized by the catalytic triad of serine, histidine and glutamic acid where the serine moiety mediates the esterase activity of the acetylcholine esterase.

Finally, due to its oxidized form in the CNS compartment, the drug is entrapped in the CNS and can not go back from CNS to periphery through the BBB.

These particular features of the compound of the invention involve an effective central anticholinesterasic activity and reduction, or better suppression, of side effects due to a peripheral anticholinesterasic action.

In addition, the compound of the invention is an acetylcholinesterase inhibitor, at least 500 times more active in central nervous system CNS than in peripheral nervous system PNS or preferably at least 1000 times more active in central nervous system CNS than in peripheral nervous system PNS.

In one embodiment, the compound of the invention is an acetylcholinesterase inhibitor, at least 500 times more active in central nervous system CNS under its oxidized form than in peripheral nervous system PNS under its non oxidized form or under the prodrug in its non oxidized form.

In another embodiment, the compound of the invention is an acetylcholinesterase inhibitor, at least 1000 times more active in central nervous system CNS under its oxidized form than in peripheral nervous system PNS under its non oxidized form or under the prodrug in its non oxidized form.

The compound of the invention is selected for presenting the particular feature of having a distance d comprised between 0.3 and 0.8 nanometers preferably between 0.4 and 0.7 nanometers.

This distance is calculated on the oxidized form of a defined compound from a modelisation Chemdraw or a Cerius software on a Silicon graphic station.

The adequate distance d is defined from the structure of acetylcholinesterase enzyme active site reported in the literature ("Structure of acetylcholinesterase complexed with E2020 (Aricept®): implications for the design of new anti-Alzheimer drugs." Structure Pages 297-307 Gitay Kryger, Israel Silman and Joel L Sussman; "The rationale for E2020 as a potent acetylcholinesterase inhibitor" Bioorganic and Medicinal Chemistry. Pages 1429-1446 Yoshiyuki Kawakami, Atsushi Inoue, Takatoshi Kawai, Misako Wakita, Hachiro Sugimoto and Anton J. Hopfinger; "Transition State Structure and Rate Determination for the Acylation Stage of Acetylcholinesterase Catalyzed Hydrolysis of (Acetylthio) choline" Siobhan Malany, Monali Sawai, R. Steven Sikorski, Javier Seravalli, Daniel M. Quinn, Zoran Radic, Palmer Taylor, Chanoch Kronman, Baruch Velan, and Avigdor Shafferman Journal of American Chemical Society. pp 2981-2987; "Direct determination of Acetyl-Enzyme Intermediate in the Acetylcholinesterase-catalysed Hydrolysis of Acetylcholine and acetylthiocholine" Harry C. Froede and Irwin B. Wilson The journal of Biological Chemistry, 1984, 259, pp 11010-11013.)

The present invention relates to compounds described by structural formula G

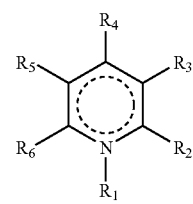

G wherein the dotted circle line represents one double bond between $CR_5$-$CR_6$, and another double bond between either $CR_2$-$CR_3$ or $CR_3$-$CR_4$; and either a) $R_1$ $R_2$ $R_3$ $R_4$ $R_5$ $R_6$ which may be identical or different are hydrogen, OH, ($C_1$-$C_8$)alkyl, aryl, heteroaryl, ($C_1$-$C_8$) alkylaryl, aryl ($C_1$-$C_8$)alkyl, alkoxy, hydroxy ($C_1$-$C_8$) alkyl, alkoxy ($C_1$-$C_8$)alkyl, phenyl, $(CH_2)_n$—COOH, Z, $Z_1$;

or b) $R_4$ and $R_5$ or c) $R_5$ and $R_6$ taken together with the carbon atoms to which they are attached form a 6-membered aromatic ring or form a 5- or 6-membered heterocyclic ring being optionally substituted by one or more group, identical or different, defined as OH, ($C_1$-$C_8$) alkyl, aryl, heteroaryl, ($C_1$-$C_8$)alkylaryl, aryl ($C_1$-$C_8$)alkyl, alkoxy, hydroxy ($C_1$-$C_8$)alkyl, alkoxy ($C_1$-$C_8$)alkyl, phenyl, $(CH_2)_n$ —COOH, Z, Za; and in all case a) and b) and c);

at least one group among $R_2$ $R_3$ $R_5$ is an electron withdrawing group selected from the group comprising COOR, COSR, CONRR', CN, COR, $CF_3$, SOR, $SO_2R$, SONRR', $SO_2NRR'$, $NO_2$, halogen, heteroaryl, wherein R, R' being a group H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenalkyl, thioalkyl, thioalkoxyalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached form an heterocyclic ring of at least 3 members, preferably a 5 or 6 membered heterocyclic ring such as for example morpholine, optionally substituted by one or more groups being as defined for $R_2$, or R and R' taken together with the nitrogen atom to which they are attached form a fused polyheterocyclic system preferably tetrahydroisoquinoline, indoline, isoindoline, optionally substituted by one or more group being as defined for $R_2$;

and wherein

Z is a group defined by formula $-(L)_m$-$Z_1$, L is ($C_1$-$C_8$)alkyl, aryl, heteroaryl, phenyl, ($C_1$-$C_8$) alkylaryl, aryl($C_1$-$C_8$) alkyl;

$Z_1$ is defined by formula

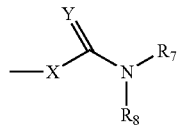

wherein X, Y is O, S; $R_7$, $R_8$ which may be identical or different are hydrogen, ($C_1$-$C_8$) alkyl, aryl, heteroaryl, ($C_1$-$C_8$)alkylaryl, phenyl, cyclopropyl, $(CH_2)_n$—COOH; and wherein n and m are an integer $\geq 1$, preferably m is comprised between 1 and 4 and n is comprised between 1 and 6;

and provided that at least one group $R_1$ $R_2$ $R_3$ $R_4$ $R_5$ or $R_6$ is Z or $Z_1$ and that $R_1$ is not H or $Z_1$;

or a pharmaceutical salts or a stereoisomer thereof.

By "alkyl" radical containing 1 to 8 carbon atoms, is intended to mean methyl, ethyl, propyl, isopropyl, as well as butyl, pentyl or hexyl etc. . . . linear or branched radical.

As used herein, "aryl" is intended to mean any stable monocyclic or bicyclic carbon ring of up to 7 atoms in each ring, wherein at least one ring is aromatic.

Examples of such aryl elements include, but are not limited to, phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The terms "arylakyl" or "alkylaryl" radical, include an alkyl portion where alkyl is as defined above and aryl portion where aryl are as defined above. Examples of arylalkyl include, but are not limited to, benzyl, halobenzyl, phenylethyl, phenylpropyl, halophenylethyl, thienylethyl, thienylpropyl. Examples of alkylaryl include toluene, ethylbenzene, propylbenzene.

By "halo" or "halogen" radical or by halogen atom is intended to mean fluorine, chlorine, bromine or iodine.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl.

"Alkoxy" represents either a cyclic or non-cyclic alkyl group of indicated number of carbon atoms attached through an oxygen bridge. "Alkoxy" therefore encompasses the definitions of alkyl and cycloalkyl above.

"heteroaryl" means a mono or polycyclic system of at least 5 members by cycle combining aliphatic and aromatic rings and may be selected among thienyl, furyle, pyrrolyl, imidazolyl, thiazolyl, thiazolinyl, oxazolyl, oxazolinyl, thiadiazolyl, oxadiazolyl, tetrazolyl, pyridyl, pyridazinyl, pyrazinyl, pyrimidinyl, indolyl, benzothienyl, benzofuranyl indazolyl, benzothiazolyl, naphtyridinyle, quinolyl, isoquinolyl, cinnolyl, quinazolyl, quinoxalyle, benzoxazolyl, benzimidazolyl, or triazolyl, optionally substituted by one or more groups as defined above.

An "electron withdrawing group" means a group which draws electrons away from a reaction center. The EWG removes electron density from a p system making it less nucleophilic either by electronic effect or by resonance effect.

The invention concerns also stereoisomer or a mixture of stereoisomers of the compound of formula G as defined above in any ratio, or a physiologically acceptable salt thereof.

The compound of the invention as cited above comprises an electron withdrawing group (EWG). This EWG is placed in alpha or beta position to the nitrogen atom. Thus the presence of the EWG increases the stability of the final compound of formula G. The EWG group being in the position as defined above is selected from the group comprising COOR, COSR, CONRR', CN, COR, $CF_3$, SOR, $SO_2R$, SONRR', $SO_2NRR'$, $NO_2$, halogen, heteroaryl, wherein R, R' being a group H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenalkyl, thioalkyl, thioalkoxyalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached form an heterocyclic ring of at least 3 members, preferably a 5 or 6 membered heterocyclic ring, optionally substituted by one or more groups being as defined for $R_2$, or R and R' taken together with the nitrogen atom to which they are attached form a fused polyheterocyclic system preferably tetrahydroisoquinoline, indoline, isoindoline, optionally substituted by one or more group being as defined for $R_2$;

In a preferred embodiment the electron withdrawing group EWG is constituted by $R_2$ and $R_3$ or $R_3$ and $R_4$ taken together with the carbon atoms to which they are attached form a 5 to 7 membered heterocycle, preferably selected from lactame, N-alkyllactame, N-aryllactame, N-heteroaryllactame, lactone, thiolactone.

In another embodiment $R_1$ and $R_6$ or $R_1$ and $R_2$ taken together with the atoms to which they are attached form a 5 to 7 membered heterocycle, optionally substituted by one or more groups being as defined above for the R group.

In a preferred embodiment of the invention, the compounds are selected from those of formula G1a or G1b:

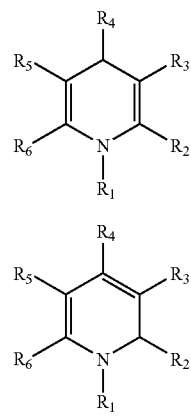

wherein $R_1$ $R_2$ $R_3$ $R_4$ $R_5$ $R_6$ have the same meaning as defined above. In a specific embodiment the compound of formula G1 comprises two electron withdrawing groups in beta position from the nitrogen atom namely in $R_3$ and $R_5$ position.

Among the compounds of formula G1a, a quite particular subject of the invention is the compounds the names of which follow:
Ethyl 1-methyl 5-(N,N-dimethylcarbamate)-1,4-dihydropyridine-3-carboxylate;
Ethyl 1-methyl-5-(N,N-dimethylthiocarbamate)-1,4-dihydro-5-O-pyridine-3-carboxylate;
Ethyl 1-methyl-5-(N,N-dimethylthiocarbamate)-1,4-dihydro-5-S-pyridine-3-carboxylate;
1-Methyl-3-(methylsulfonyl)-5-(N,N-dimethylcarbamate)-1,4-dihydropyridine;
1-Methyl-3-(N,N-diethylcarboxamido)-5-(N,N-dimethylcarbamate)-1,4-dihydropyridine;
(+/−)-1-Methyl-3-(methylsulfinyl)-5-(N,N-dimethylcarbamate)-1,4-dihydropyridine;
1-Methyl-3-(trifluoromethyl)-5-(N,N-dimethylcarbamate)-1,4-dihydropyridine;
1-Methyl-3-(4,5-dihydro-4,4-dimethyl-2-oxazolyl)-5-(N,N-dimethylcarbamate)-1,4-dihydropyridine;
N,N-diethyl-1-methyl-5-(N,N-dimethylcarbamate)-1,4-dihydropyridine-3-sulfonamide;
Ethyl 1-[2-(N,N-dimethylcarbamate)benzyl]-1,4-dihydropyridine-3-carboxylate;
1-[2-(N,N-dimethylcarbamate)benzyl]-3-(methylcarbamoyl)-1,4-dihydropyridine;
1-[2-(N,N-dimethylcarbamate)benzyl]-3-(4,5-dihydro-4,4-dimethyl-2-oxazolyl)-1,4-dihydropyridine;
N,N-diethyl-1-[2-(N,N-dimethylcarbamate)benzyl]-1,4-dihydropyridine-3-sulfonamide;
1-[2-(N,N-dimethylcarbamate)benzyl]-3-(trifluoromethyl)-1,4-dihydropyridine;
Ethyl 1-methyl-2-[2-(N,N-dimethylcarbamate)phenyl]-1,4-dihydropyridine-3-carboxylate;
1-Methyl-2-[2-(N,N-dimethylcarbamate)phenyl]-1,4-dihydro-N,N-dimethylnicotinamide;
1-Methyl-2-[2-(N,N-dimethylcarbamate)phenyl]-3-(methylsulfonyl)-1,4-dihydropyridine;
N-methyl-1-methyl-2-[2-(N,N-dimethylcarbamate)phenyl]-1,4-dihydropyridine-3-sulfonamide;
Ethyl 1-methyl-6-[2-(N,N-dimethylcarbamate)phenyl]-1,4-dihydropyridine-3-carboxylate;
Ethyl 1-methyl-5-[2-(N,N-dimethylcarbamate)phenyl]-1,4-dihydropyridine-3-carboxylate;
Ethyl 1-methyl-5-(N,N-dimethylcarbamate)1,4-dihydropyridine-3-carboxylate.

Among the compounds of formula G1b a quite particular subject of the invention is the compounds the names of which follow:
Ethyl 1-methyl 5-(N,N-dimethylcarbamate)-1,2-dihydropyridine-3-carboxylate;
Ethyl 1-methyl-5-(N,N-dimethylthiocarbamate)-1,2-dihydro-5-S-pyridine-3-carboxylate;
1-Methyl-3-(N,N-diethylcarboxamido)-5-(N,N-dimethylcarbamate)-1,2-dihydropyridine;
Ethyl 1-methyl-5-(N,N-dimethylcarbamate)-1,2-dihydropyridine-3-carboxylate.

In a preferred embodiment of the invention, the compounds are selected from those of formula G2:

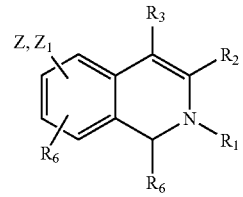

wherein $R_1$ $R_2$ $R_3$ & Z or $Z_1$ have the same meaning as defined above. In a specific embodiment the compound of formula G2 comprises two electron withdrawing groups in alpha and beta position from the nitrogen atom namely in $R_2$ and $R_3$ position.

Among the compounds of formula G2 a quite particular subject of the invention is the compounds the names of which follow:
2-Methyl-7-(N,N-dimethylcarbamate)-1,2-dihydroisoquinoline;
2-Methyl-7-(N,N-dimethylthiocarbamate)-1,2-dihydro-7-O-isoquinoline;
2-Methyl-7-(N,N-dimethylthiocarbamate)-1,2-dihydro-7-S-isoquinoline;
1,2-Dimethyl-7-(N,N-dimethylthiocarbamate)-1,2-dihydro-7-O-isoquinoline;
Ethyl 2,3-dimethyl-6,8-di(N,N-dimethylcarbamate)-1,2-dihydroisoquinoline-4-carboxylate;
2,3-Dimethyl-6,8-di(N,N-dimethylcarbamate)-1,2-dihydroisoquinoline-4-carboxamide;
2,3-Dimethyl-4-(4,5-dihydro-4,4-dimethyl-2-oxazolyl)-6,8-di(N,N-dimethylcarbamate)-1,2-dihydroisoquinoline;
(+/−)-2,3-Dimethyl-4-(4-methylphenylsulfinyl)-6,8-di(N,N-dimethylcarbamate)-1,2-dihydroisoquinoline;

2,3-Dimethyl-4-[(4-methylphenyl)sulfonyl]-6,8-di(N,N-dimethylcarbamate)-1,2-dihydroisoquinoline;
2,3-Dimethyl-4-[N-phenylsulfonamide]-6,8-di(N,N-dimethylcarbamate)-1,2-dihydroisoquinoline;
2,3-Dimethyl-4-(trifluoromethyl)-6,8-di(N,N-dimethylcarbamate)-1,2-dihydroisoquinoline;
Ethyl 2-[2-(N,N-dimethylcarbamate)benzyl]-1,2-dihydroisoquinoline-4-carboxylate;
2-[2-(N,N-dimethylcarbamate)benzyl]-4-(N—-phenethylcarbamoyl)-1,2-dihydroisoquinoline;
2-[2-(N,N-dimethylcarbamate)benzyl]-4-(4,5-dihydro-4,4-dimethyl-2-oxazolyl)-1,2-dihydroisoquinoline;
N,N-diethyl-2-[2-(N,N-dimethylcarbamate)benzyl]-1,2-dihydroisoquinoline-4-sulfonamide;
1-[2-(N,N-dimethylcarbamate)benzyl]-3-(trifluoromethyl)-1,2-dihydroisoquinoline;
1-[2-(N,N-dimethylcarbamate)phenyl]-2-methyl-1,2-dihydroisoquinoline;
2-Methyl-4-[2-(N,N-dimethylcarbamate)phenyl]-1,2-dihydroisoquinoline;
2-Methyl-5-(N,N-dimethylcarbamate)-1,2-dihydroisoquinoline;
2-Methyl-7-(N,N-dimethylcarbamate)-1,2-dihydroisoquinoline;
2-Methyl-5-(N,N-dimethylthiocarbamate)-O-1,2-dihydroisoquinoline.

In a preferred embodiment of the invention, the compounds are selected from those of formula G3a or G3b:

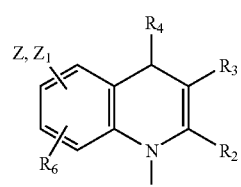

G3a

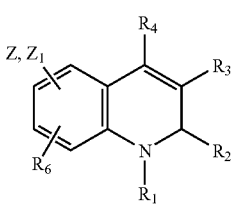

G3b wherein $R_1$ $R_2$ $R_3$ $R_4$ $R_6$ Z or $Z_1$ have the same meaning as defined above. In a specific embodiment, the compound of formula G3 comprises one electron withdrawing groups in beta position from the nitrogen atom namely in $R_3$ position.

Among the compounds of formula G3a a quite particular subject of the invention is the compounds the names of which follow:
Ethyl 1-methyl-7-(N,N-dimethylcarbamate)-1,4-dihydroquinoline-3-carboxylate;
Ethyl 1-methyl-5-(N,N-dimethylcarbamate)-1,4-dihydroquinoline-3-carboxylate;
Ethyl 1-methyl-5,7-di(N,N-dimethylcarbamate)-1,4-dihydroquinoline-3-carboxylate;
Ethyl 1-methyl-5,8-di(N,N-dimethylcarbamate)-1,4-dihydroquinoline-3-carboxylate;
Ethyl 1-methyl-1,4-dihydro-5-O-quinoline-N,N-dimethylthiocarbamate-3-carboxylate;
Ethyl 1-methyl-1,4-dihydro-5-S-quinoline-N,N-dimethylthiocarbamate-3-carboxylate;
1-Methyl-5-(N,N-dimethylcarbamate)-3-(N,N-diethylcarboxamido)-1,4-dihydroquinoline;
1-Methyl-7-(N,N-dimethylcarbamate)-3-(4,5-dihydro-4,4-dimethyl-2-oxazolyl)-1,4-dihydroquinoline;
1-Methyl-5-(N,N-dimethylcarbamate)-3-trifluoromethyl-1,4-dihydroquinoline;
(+/−)-1-Methyl-3-(4-methylphenylsulfinyl)-5-(N,N-dimethylcarbamate)-1,4-dihydroquinoline;
1-Methyl-3-(4-methylphenylsulfonyl)-5-(N,N-dimethylcarbamate)-1,4-dihydroquinoline;
1-Methyl-5-(N,N-dimethylcarbamate)-3-(N-phenylsulfomanide)-1,4-dihydroquinoline;
1-Methyl-6,7-di(N,N-dimethylcarbamate)-3-nitro-1,4-dihydroquinoline;
Ethyl 1-methyl-2-phenyl-6,7-di(N,N-dimethylcarbamate)-1,4-dihydroquinoline-3-carboxylate;
Ethyl 1,2,4-trimethyl-7-(N,N-dimethylcarbamate)-1,4-dihydroquinoline-3-carboxylate;
Ethyl 1-[2-(N,N-dimethylcarbamate)benzyl]-1,4-dihydroquinoline-3-carboxylate;
1-[2-(N,N-dimethylcarbamate)benzyl]-3-(dimethylcarbamoyl)-1,4-dihydroquinoline;
1-[2-(N,N-dimethylcarbamate)benzyl]-3-(4,5-dihydro-4,4-dimethyl-2-oxazolyl)-1,4-dihydroquinoline;
N,N-dimethyl-1-[2-(N,N-dimethylcarbamate)benzyl]-1,4-dihydroquinoline-3-sulfonamide;
1-[2-(N,N-dimethylcarbamate)benzyl]-3-(trifluoromethyl)-1,4-dihydroquinoline;
Ethyl 1-methyl-2-[2-(N,N-dimethylcarbamate)phenyl]-1,4-dihydroquinoline-3-carboxylate;
Ethyl 1-methyl-8-[2-(N,N-dimethylcarbamate)phenyl]-1,4-dihydroquinoline-3-carboxylate;
Methyl 1-methyl-5-(N,N-dimethylcarbamate)-1,4-dihydroquinoline-3-carboxylate;
1-Methyl-3-(N-methylcarboxamido)-5-(N,N-dimethylcarbamate)-1,4-dihydroquinoline;
Morpholine 4-[1-methyl-5-(N,N-dimethylcarbamate)-1,4-dihydroquinolyl-3-carbonyl];
Methyl 1-methyl-5-(N-ethylcarbamate)-1,4-dihydroquinoline-3-carboxylate:
1-Methyl-3-(N-propylcarboxamido)-7-(N,N-dimethylcarbamate)-1,4-dihydroquinoline;
3-(N,N-methylcarboxamido)-5-(N,N-dimethylcarbamate)-1,4-dihydroquinoline;
Methyl 1-methyl-5,7-bis(N,N-dimethylcarbamate)-1,4-dihydroquinoline-3-carboxylate;
Methyl 1-methyl-8-(N,N-dimethylcarbamate)-1,4-dihydroquinoline-3-carboxylate;
Ethyl 1-methyl-8-(N,N-dimethylcarbamate)-1,4-dihydroquinoline-3-carboxylate;

Among the compounds of formula G3b a quite particular subject of the invention is the compounds the names of which follow
Ethyl 1-methyl-7-(N,N-dimethylcarbamate)-1,2-dihydroquinoline-3-carboxylate;
Ethyl 1-methyl-(N,N-dimethylthiocarbamate)-1,2-dihydro-5-S-quinoline-3-carboxylate;
1-Methyl-5-(N,N-dimethylcarbamate)-3-(4,5-dihydro-4,4-dimethyl-2-oxazolyl)-1,2-dihydroquinoline;
3-(N,N-methylcarboxamido)-5-(N,N-dimethylcarbamate)-1,2-dihydroquinoline;
Methyl 1-methyl-5,7-bis(N,N-dimethylcarbamate)-1,2-dihydroquinoline-3-carboxylate;
Methyl 1-methyl-8-(N,N-dimethylcarbamate)-1,2-dihydroquinoline-3-carboxylate;
Ethyl 1-methyl-8-(N,N-dimethylcarbamate)-1,2-dihydroquinoline-3-carboxylate;

Another object of the invention is the compound of formula G+ or G+1, G+2, G+3 wherein all the specific compounds cited above are in their corresponding positively charged form such as pyridinium or quinolinium or isoquinolinium form.

G+ G1+

G2+

G3+ wherein $R_1$ $R_2$ $R_6$ $R_3$ $R_5$ $R_6$ Z or $Z_1$ have the same meaning as defined above.

These compounds are either the starting product for obtaining the compound of respectively formula G, G1a, G1b, G2, G3a, G3b by a step of reduction, or the active drug which is liberated in vivo in the CNS.

As starting product they are under a salt form G+W− wherein W is the leaving group of the alkylating agent R1-W which is involved in the quaternization reaction step as explain below.

As an active drug in the CNS, they are in an ammonium non salted form.

As intermediate compounds for the preparation of compounds of formula G+, G+1, G+2, G+3 as described above, another object of the invention is the compounds of formula G' or G'1, G'2, G'3:

G' G'1

G'2

G'3

These compounds are starting products for obtaining, by a step of quaternarization with an alkylating agent $R_1$—W, the compounds of formula G+, G+1, G+2, G+3 according to the process explained below.

Another object of the invention is a process allowing the preparation of the compounds of formula general G and the sub family of compound of formula G1a G1b, G2, G3a, G3b as defined above.

This process comprises a stage of reduction of a compound of formula $G_i^+$ W− i is 1, 2 or 3 as defined above in the presence of a reducing agent.

Regioselective 1,4-reduction is carried out with sodium dithionite in the presence of sodium carbonate, but other reducing agents may be used in this step, for example NaBH$_3$CN and BNAH, providing the 1,4-dihydropyridine of formula G1a or 1,4-dihydroquinolines of formula G3a. The use of sodium borohydride give rise to the formation of a pure 1,2-dihydroisoquinoline of formula G2 or a mixture of 1,2- and 1,4-dihydroquinolines or 1,2- and 1,4-dihydropyridines. Chemical separation give rise to the formation of pure 1,2-dihydropyridine of formula G1b or 1,2-dihydroquinolines of formula G3b Another object of the invention is a process allowing the preparation of the compounds of formula $G_i^+$ W−, i being 1, 2 or 3 as defined above which comprises a first step of carbamoylation of a compound of formula E1 or E2 or E3:

E1

E2

E3

Carbamoylation is carried out in the presence of potassium carbonate or metal hydride such as sodium hydride with an agent of formula W'—Z or W'—Z'$_1$ wherein Z'1 is

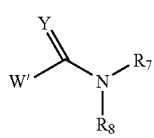

and W' is a leaving group, preferably selected from halogen, O-triflate, sulfate, tosylate, mesylate, Z'1 being for example a dialkylcarbamoyl halide, in a solvent. Also thiocarbamoylation is achieved in the presence of dialkylthiocarbamoyl halide.

In this step the reaction of carbamoylation is carried out on starting compounds wherein either $R_5$ or $R_6$ or P are a hydroxy group.

The process comprises a following step of quaternization of the nitrogen atom by treatment of the resulting carbamate with all type of alkylating agents $R_1$—W in a solvent which provides the desired pyridinium, quinolinium or isoquinolinium salt.

The synthesis of the starting product of formula E1, E2, E3 is described below. When the reaction sequence carbamoylation, quaternization and reduction steps is carried out on compounds of formula E1, E2, E3, the respective compound of formula G1a, G1b, G2, G3a, G3b are obtained.

The synthesis of the following pyridine derivatives of formula E1 is reported in the literature.

3-Methoxy-5-(methylsulfinyl)pyridine (Phosphorus, Sulfur and Silicon and the Related Elements, 1992, 66, 127-137);
3-Methoxy-5-(methylsulfonyl)pyridine (Tetrahedron, 1985, 173-1384)
Ethyl 5-methoxypyridine-3-carboxylate (Journal of medicinal chemistry, 2000, 43, 3168-3185);
3-Cyano-5-methoxypyridine (Journal of Medicinal Chemistry, 2000, 43, 3168-3185);

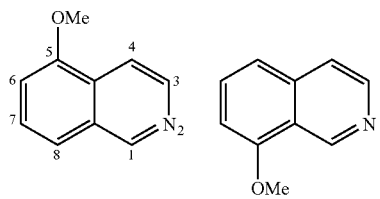

From these available pyridines, the desired carbamates, O-isoquinoline thiocarbamates and S-thiocarbamates of formula G1a or G1b substituted on the 3-position by an ester, a ketone, a trifluoromethyl, an amide, a sulfoxide, a sulfone, a sulfonamide, an oxazoline are prepared following the same reaction sequence carbamoylation, quaternarization and reduction steps as that reported previously.

The synthesis of the isoquinolines derivatives of formula E2 are prepared as following:

The preparation of the following methoxy isoquinolines is reported in the literature by Pommeranz-Fritsch cyclisation.
5-Methoxyisoquinoline (Bioorganic and Medicinal Chemistry, 1999, 2647-2666);
6-Methoxyisoquinoline (Bioorganic and Medicinal Chemistry Letters, 2003, 1345-1348);
7-Methoxyisoquinoline (Bioorganic and Medicinal Chemistry, 1999, 2647-2666);
8-Methoxyisoquinoline (Bioorganic and Medicinal Chemistry, 1999, 2647-2666);
5,7-Methoxyisoquinoline ((Tetrahedron, 37, 1981, 3977-3980);
5,8-Methoxyisoquinoline (Journal of Chemical Society, Perkin Transactions 1: Organic and Bio-organic Chemistry, 1974, 2185-2190);
6,8-Methoxyisoquinoline (Journal of Organic Chemistry, 32, 1967, 2689-2692);
6,7-Methoxyisoquinoline (Tetrahedron, 37, 1981, 3977-3980);
7,8-Methoxyisoquinoline (Tetrahedron Letters, 38, 3159-3162);

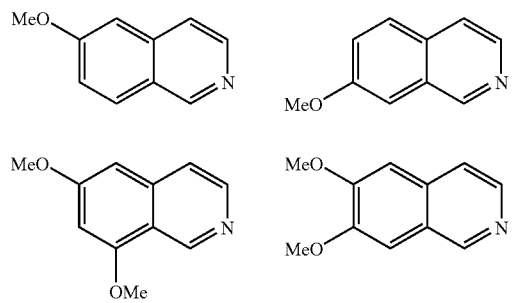

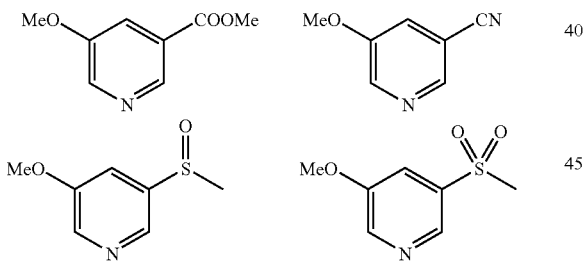

The previous methoxy isoquinolines are transformed into the desired isoquinoline carbamates, O-isoquinoline thiocarbamates and S-isoquinoline thiocarbamates of formula G2 according to the previous reaction sequence above, O-demethylation, carbamoylation, thiocarbamoylation, quaternization and reductions steps.

The desired 1-substituted isoquinolines are prepared by addition of an alkyllithium, a Grignard reagent or a cuprate on the corresponding isoquinolinium salts, affording the 1,2-dihydroisoquinolines.

The following 4-cyano isoquinolines and methyl isoquinoline-4-carboxylate derivatives are reported in the literature:
4-Cyano-6,7-dimethoxyisoquinolines (Canadian Journal of Chemistry, 1968, 46, 1160-1163);
3-Methyl 4-cyano-6,8-dimethoxyisoquinolines (Tetrahedron Letters, 1968, 44, 4631-4634);
Methyl 6-methoxyisoquinoline-4-carboxylate (EP1466604);

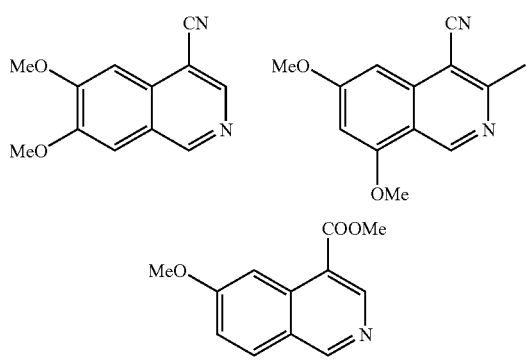

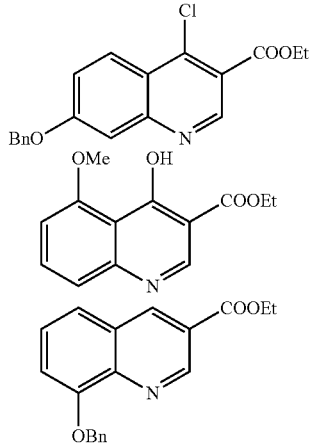

From these 4-cyanoisoquinolines and methyl isoquinoline-4-carboxylate, the desired carbamates, O-isoquinolinethiocarbamate and S-thiocarbamates of formula G2 substituted on the 4-position by an ester, a trifluoromethyl an amide, a sulfoxide, a sulfone, a sulfonamide, an oxazoline are prepared following the same reaction sequence as that reported previously.

The quinolines derivative of formula E3 are prepared as following:

The synthesis of the following cyanoquinolines is reported in the literature (Tetrahedron Letters, 39, (1998) 4013-4016).

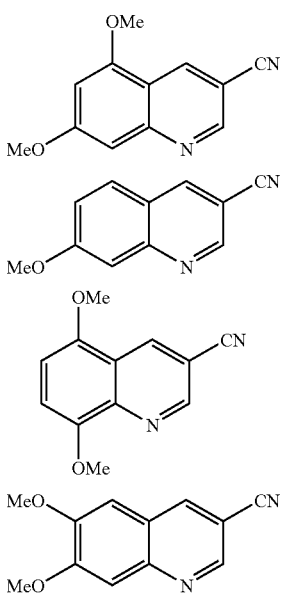

The preparation of the following ethyl quinoline-3-carboxylates is reported in the literature (Journal of Medicinal Chemistry 1995, 38, 950-957).

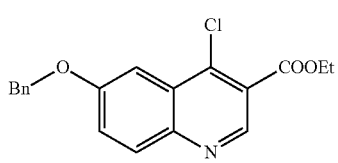

The cyanoquinolines cited above are treated with 48% HBr in aqueous solution to promote deprotection of the methoxy group and hydrolysis of the 3-cyano group. The corresponding carboxylic acids are then converted into esters with thionyl chloride in refluxing ethanol.

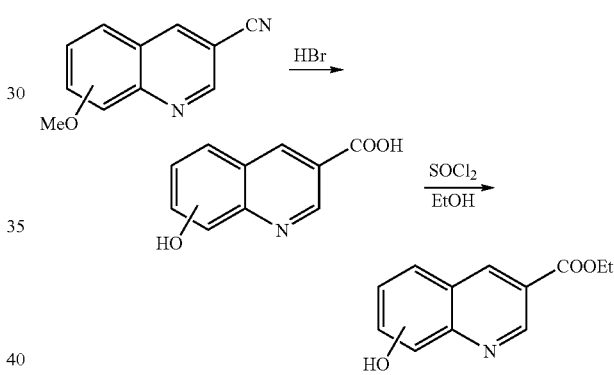

Carbamoylation is accomplished in the presence of sodium hydride with dimethylcarbamoyl chloride in THF. Treatment of the resulting carbamate with methyl triflate in dichloromethane provides the desired quinolinium salt. All type of alkylating agents can be used in the quaternization step ($CH_3I$, $PhCH_2X$, $XCH_2COOR$). Regioselective 1,4-reduction is carried out with sodium dithionite in the presence of sodium carbonate ($NaBH_3CN$ and BNAH may be used in this step) providing the 1,4-dihydroqunolines. The use of sodium borohydride gives rise to the formation of a mixture of 1,2- and 1,4-dihydroquinolines.

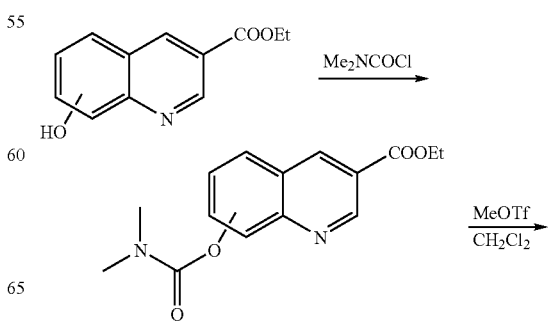

-continued

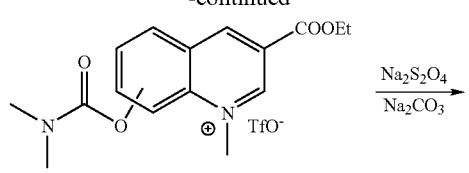
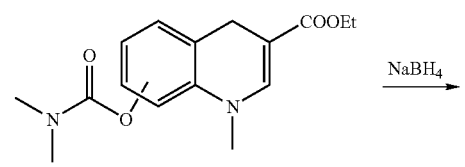
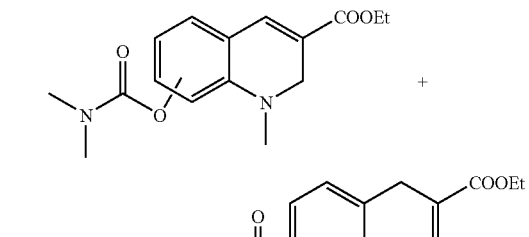
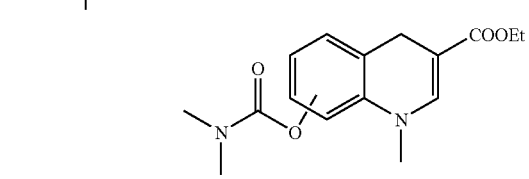

Thiocarbamoylation is achieved in the presence of dimethylthiocarbamoyl chloride. Quaternization and reduction of the corresponding O-quinoline thiocarbamates is accomplished as described above.

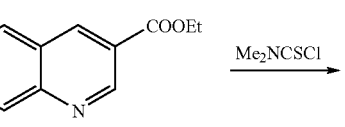
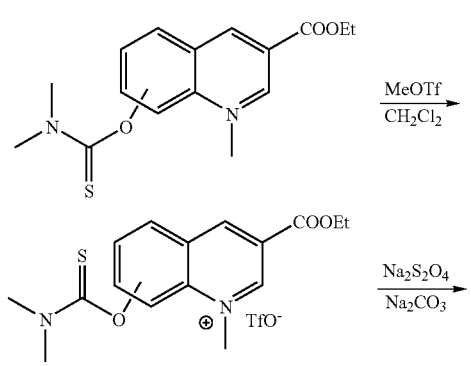
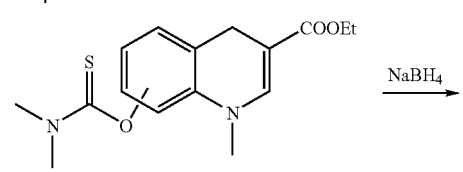
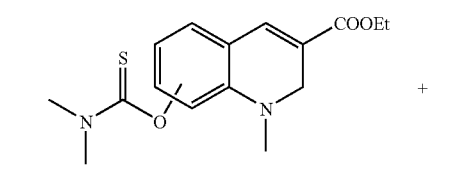

-continued

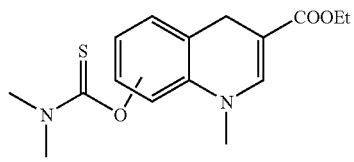

The O-quinolinethiocarbamate derivatives underwent thermal rearrangement to give rise to the corresponding S-quinolinethiocarbamates. Quaternization and reduction of the corresponding S-quinolinethiocarbamates is accomplished as described above.

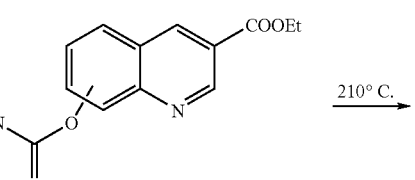
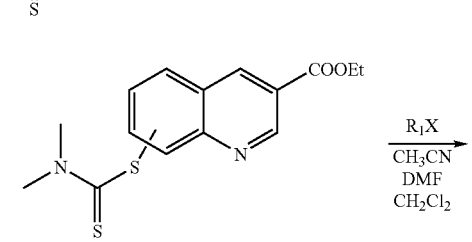
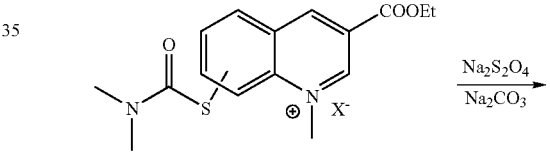
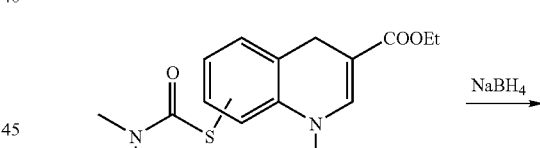
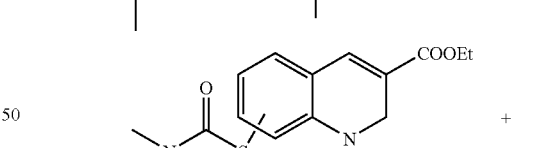
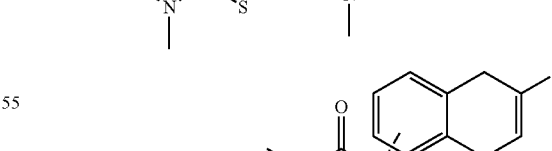
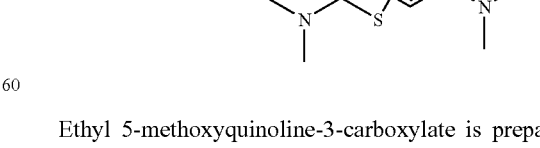

Ethyl 5-methoxyquinoline-3-carboxylate is prepared by chlorination of ethyl 4-hydroxy-5-methoxyquinoline-3-carboxylate with phosphorus oxychloride. Dechlorination was performed by hydrogenolysis. The O-demethylation, carbamoylation, thiocarbamoylation, quaternization and reduction steps are performed as described above.

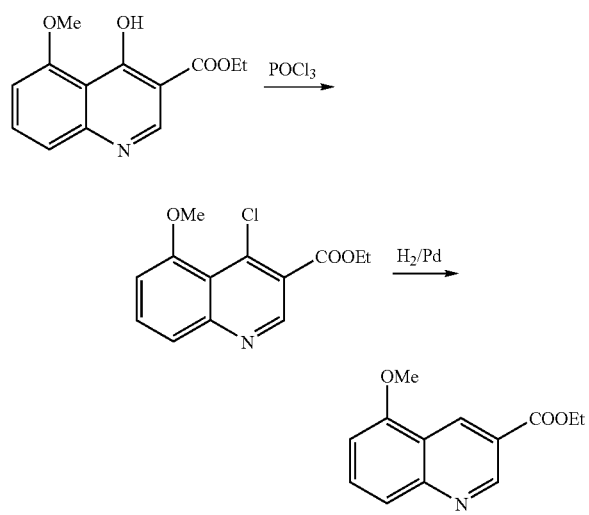

Ethyl 5-methoxyquinoline-3-carboxylate is prepared from tert-butyl N-(2-formyl-3-methoxyphenyl)carbamate (*Adv. Synth. Catal.* 2003, 345, 743-765) by condensation with methyle 3-methoxyacrylate.

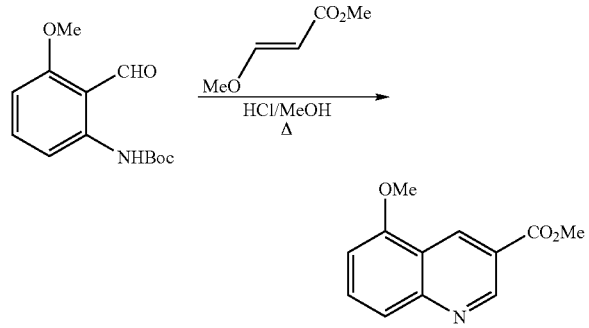

Otherwise, 5-methoxy isomers can be prepared from 2-amino-6-methoxybenzoic acid following the general procedure reported in the Journal of Medicinal Chemistry, (2001), 44, 822-833. Dechlorination of 4-chloro-5-methoxy quinoline-3-carbonitrile affords the desired 5-methoxyquinoline-3-carbonitrile. The O-demethylation, carbamoylation, thiocarbamoylation, quaternization and reduction steps are performed as described above.

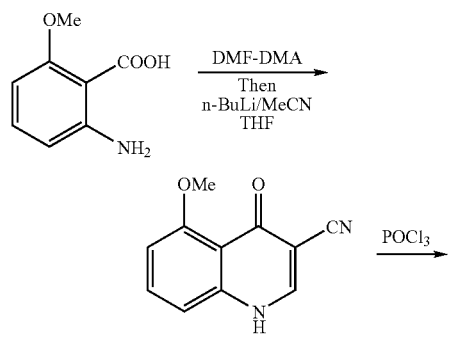

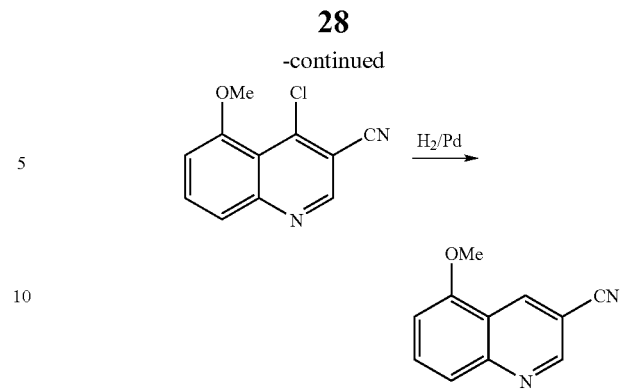

The 3-carboxamidoquinolines are prepared by amidification of 3-quinolinecarboxylic acid derivatives, followed by O-debenzylation. The carbamoylation, thiocarbamoylation, quaternization and reduction steps are performed as described above.

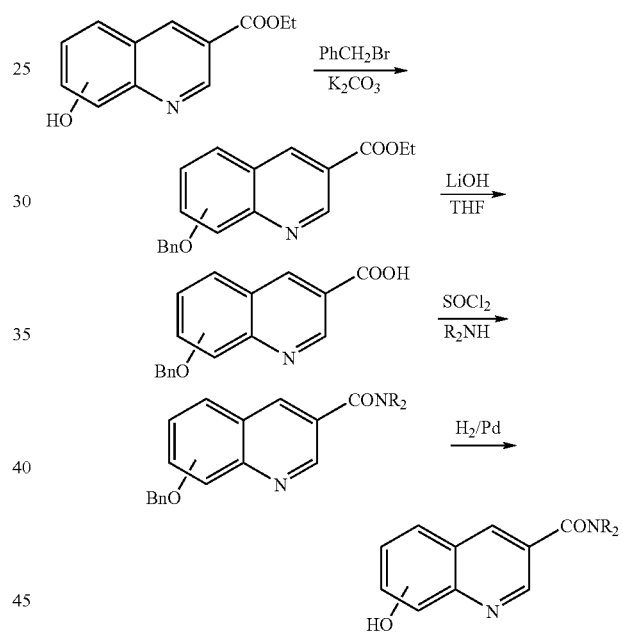

Alternatively, 3-carboxamidoquinolines are prepared from 3-cyano quinolines by partial hydrolysis using $H_2O_2$ in the presence of NaOH at 0° C. The deprotection of the methoxy group is achieved under mild conditions with $BBr_3$ in $CH_2Cl_2$. The carbamoylation, thiocarbamoylation, quaternization and reduction steps are performed as described above.

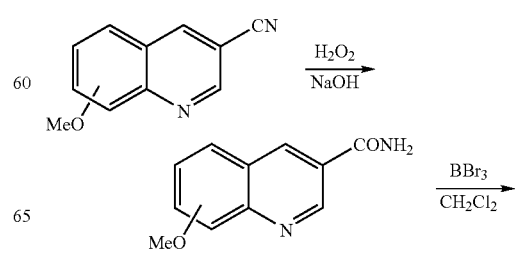

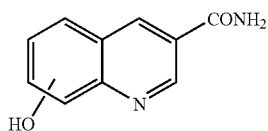

On the other hand, 3-carboxamidoquinolines are prepared from 3-cyano quinolines by hydrolysis under basic conditions to furnish 3-quinolinecarboxylic acid derivatives which are treated with SOCl$_2$ followed by addition of various amines (aromatic and aliphatic amines, aminoalcohols, aminoesters) to give rise to the desired 3-carboxamidoquinolines. The deprotection of the methoxy group is achieved under mild conditions with BBr$_3$ in CH$_2$Cl$_2$. The carbamoylation, thiocarbamoylation, quaternization and reduction steps are performed as described above.

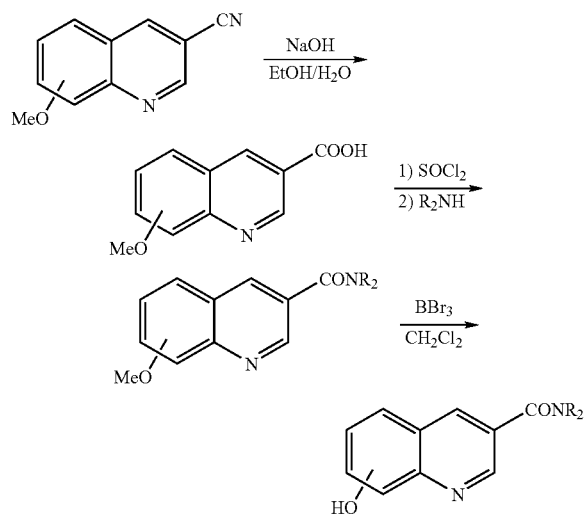

The 3-oxazolylquinolines are obtained in a one step by reaction of the cyano derivatives and an appropriate aminoalcohol. The reaction is carried out in refluxing chlorobenzene in the presence of ZnCl$_2$. Deprotection of the methoxy group is performed in the presence of BBr$_3$ in dichloromethane. The carbamoylation, thiocarbamoylation quaternisation and reductions steps are conducted as reported above.

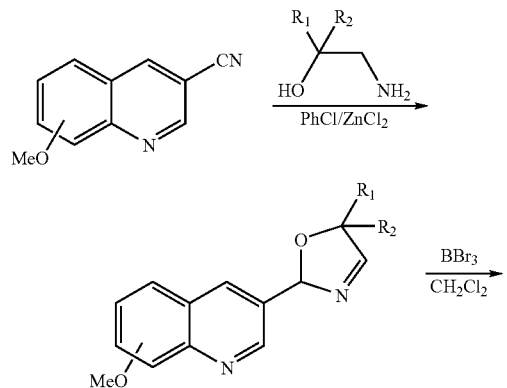

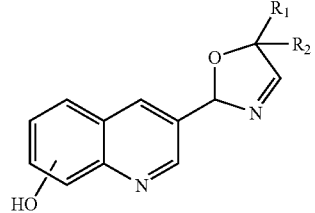

The 3-trifluoromethylquinoline derivatives are prepared in a one step by treatment of the carboxylic acids with Deoxo-Fluor. The O-demethylation, carbamoylation, thiocarbamoylation, quaternisation and reduction steps are conducted by the methods reported above.

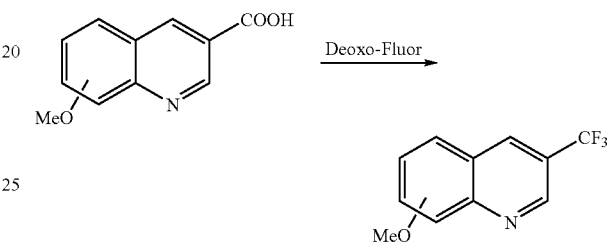

The 3-sulfinyl-substituted quinolines are prepared from the corresponding 3-bromoquinolines by metal-bromine exchange using n-butyllithium or Grignard reagents followed by treatment of the resulting metalated species with a suitable sulfinic ester or thiosulfinic ester. The 3-bromoquinolines were prepared via a Curtius rearrangement of the 3-carboxylic acids in the presence of diphenylphosphorazide (DPPA) in refluxing t-butanol. The resultant N-carbamates are diazotated with HBr—NaNO$_2$ followed by addition of molecular bromine. The O-demethylation, carbamoylation, thiocarbamoylation, quaternization and reduction steps are conducted as reported above.

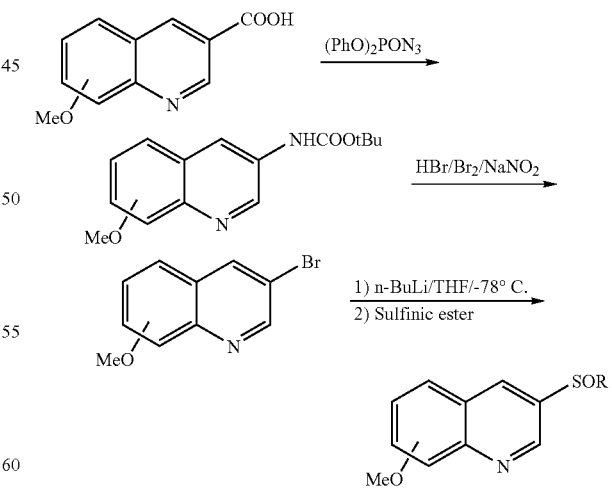

The synthesis of 3-alkylsulfonylquinolines is achieved by oxidation of the 3-sulfinylquinolines previously prepared using M-CPBA in dichloromethane. The O-demethylation, carbamoylation, thiocarbamoylation, quaternization and reduction steps are conducted as reported above.

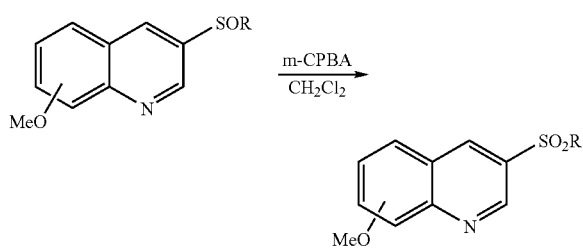

The preparation of 3-sulfonamidoquinolines is performed from the 3-(alkylsulfinyl)quinolines by Pummerer rearrangement with TFAA providing the corresponding thiol after treatment with $NEt_3$ in MeOH. The resultant thiols derivatives are treated with chlorine in AcOH to give the sulfonyl chloride derivatives which are subsequently reacted with different amines to obtain the required 3-sulfonamides -substituted quinolines. The O-demethylation, carbamoylation, thiocarbamoylation, quaternization and reduction steps are conducted as reported above.

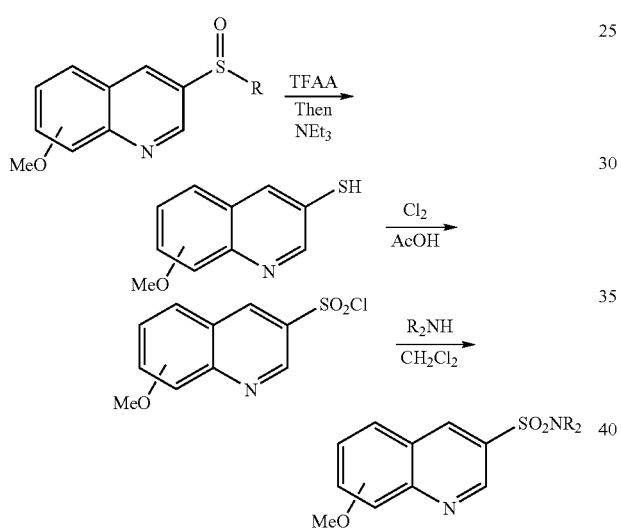

The synthesis of 3-nitroquinolines is achieved from the sodium salt of nitromalonaldehyde and various anilines as described in Journal of Medicinal Chemistry, 1994, 37, 2129-2137. The O-demethylation, carbamoylation, thiocarbamoylation, quaternization and reduction steps are conducted as reported above.

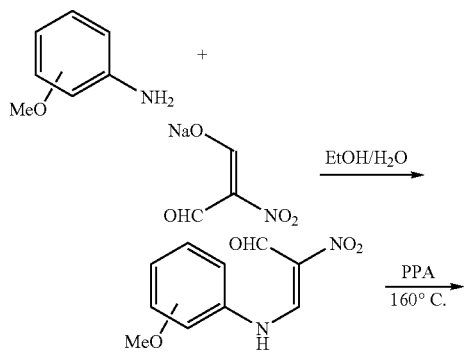

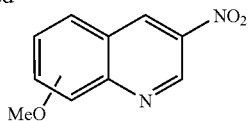

The desired 2- and/or 4-substituted quinolines are prepared by Friedländer or related methods (Organic Reaction, vol 28, 1982, page 37-201) by reaction of methoxy ortho-aminoacetophenones or methoxy ortho-aminobenzaldehydes with appropriate ketones. The reaction is conducted in various solvent (THF, EtOH, $H_2O$) under basic (KOH, NaOH, $K_2CO_3$, piperidine) or acidic condition (AcOH, p-TSA, HCl). The O-demethylation, carbamoylation, thiocarbamoylation, quaternization and reduction steps are conducted as reported above.

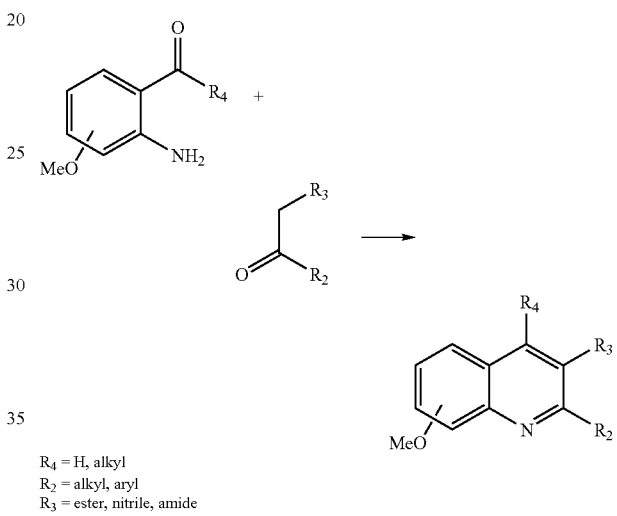

$R_4$ = H, alkyl
$R_2$ = alkyl, aryl
$R_3$ = ester, nitrile, amide

The required acetophenones and benzaldehydes used in this Friedländer approach are described in the following references. This list does not limit the scope of these acetophenones and benzaldehydes which can be used.

2-Amino-6-methoxyacetophenone (Eur. J. Org. Chem. (2001), 3247-3253);
2-Amino-5-methoxyacetophenone (Journal of Medicinal Chemistry (1987), 30(8), 1421-6);
2-Amino-4-methoxyacetophenone (Journal of Medicinal Chemistry (1989), 32(4), 807-26);
2-Amino-3-methoxyacetophenone (Journal of the Chemical Society, Abstracts (1945), 646-57);
2-Amino-4,6-dimethoxyacetophenone (Heterocycles, 2002, 57(1), 123-128);
2-Amino-4,5-dimethoxyacetophenone (Journal of Organic Chemistry (1954), 19 1117-23);
2-Amino-3,6-dimethoxyacetophenone (Journal of Medicinal Chemistry (1987), 30(8), 1421-6);
2-Amino-6-methoxybenzaldehyde (Journal of Medicinal Chemistry, 1993, 2689-22700);
2-Amino-4,5-dimethoxybenzaldehyde Tetrahedron 2001, 57, 3087-3098);
2-Amino-5-methoxybenzaldehyde (Tetrahedron Letters 2001, 42, 6589-6592);

Alternatively, the 4-substituted quinolines can be prepared from the 3-carboxamide or 3-oxazolyl or 3-cyanoquinolines previously mentioned by regioselective addition of an alkyllithium, a Grignard reagent or a cuprate affording the 1,4-dihydroquinolines. Oxidation of these intermediates by chloranil furnishes the desired 4-substituted quinolines. The O-demethylation, carbamoylation, thiocarbamoylation, quaternization and reductions steps are conducted as reported above.

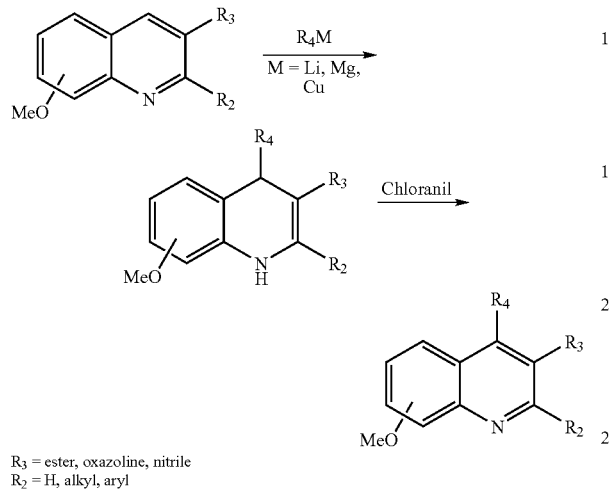

R₃ = ester, oxazoline, nitrile
R₂ = H, alkyl, aryl

In another embodiment of the compound of formula G or G⁺ of the present invention, $R_1$ is an aromatic ring bearing a carbamate function linked to the nitrogen atom.

The process for the preparation of these compounds comprises a step of quaternarization of a compound of the formula E1, E2 or E3, with an alkylating agent bearing a carbamate function.

The synthesis of an alkylating agent bearing a carbamate function, such as the following carbamates wherein an aromatic ring bearing a carbamate function is described in the literature (Chemical papers, 1985, 39, 413-427): 2-(chloromethyl)phenyl 3-(chloromethyl) phenyl and 4-(chloromethyl) phenyl N,N-dimethylcarbamate.

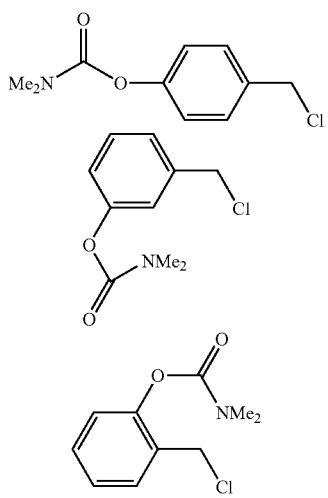

Alternatively, 4-(chloromethyl)phenyl, 3-(chloromethyl)phenyl and 2-(chloromethyl)phenyl N,N-dimethylcarbamate were prepared from 4-(hydroxymethyl)phenyl dimethyl, 3-(hydroxymethyl)phenyl and 2-(hydroxymethyl)phenyl N,N-dimethylcarbamate by reaction of cyanuric chloride in the presence of dimethylformamide in methylene chloride.

Other carbamates are prepared by reaction of 2-, 3- and 4-(chloromethyl)phenyl chloroformate with various amines.

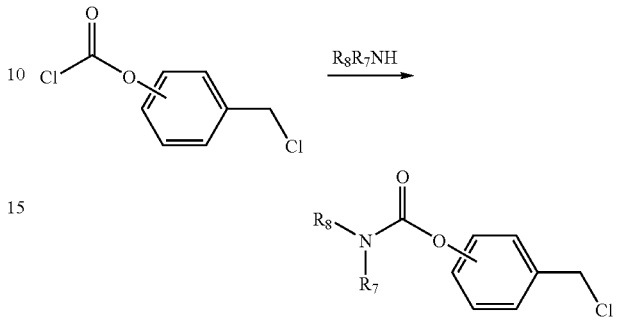

The quaternization of pyridines E1, isoquinolines E2 and quinolines E3 with the previous carbamates affords respectively the desired pyridinium G1+, isoquinolinium G2+ and quinolinium G3+ salts. The desired dihydropyridines, dihydroquinolines and dihydroisoquinolines corresponding respectively to the formula G1a, G1b, G2, G3a, G3b are obtained by reduction as previously mentioned.

In another embodiment of the compound of the present invention, an aromatic ring bearing a carbamate function as described above is connected to the aromatic ring of formula G.

The preparation of this class of compounds makes use of a cross-coupling reaction between a heterocyclic aryl halide substrate (pyridine, quinoline, isoquinoline) and an aryl boronic acid substituted by an alkoxy group. The cross-coupling reaction takes place in the presence of palladium catalyst and a base ($Na_2CO_3$, $K_2CO_3$, $Cs_2CO_3$...) in DMF/$H_2O$. The reaction mixture is refluxed at 50-80° C. for 12 hours.

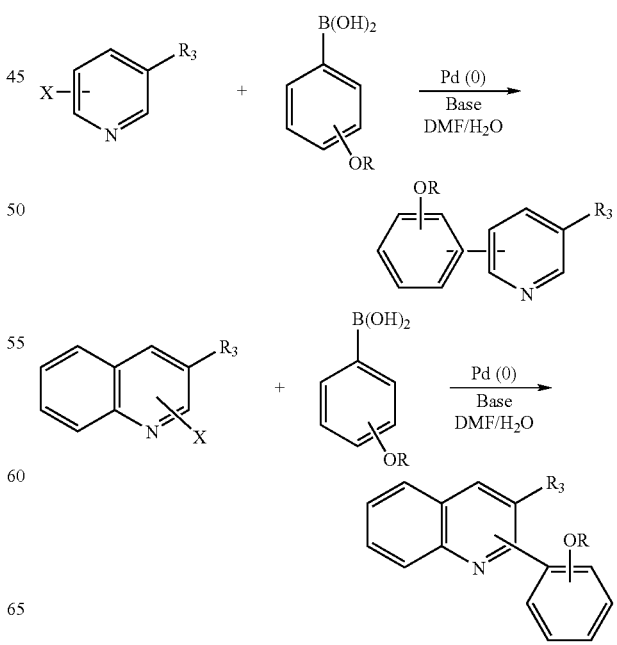

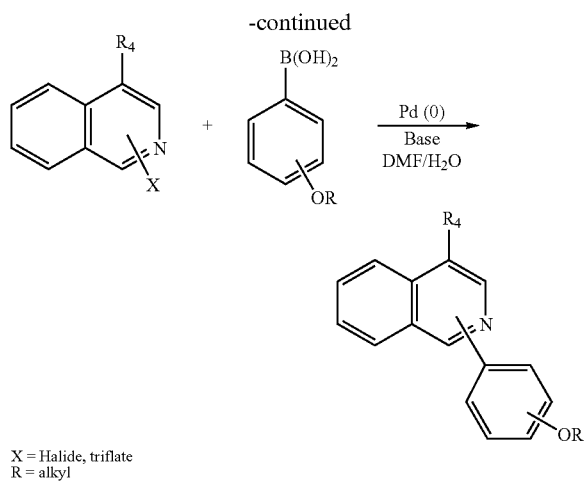

X = Halide, triflate
R = alkyl

The O-demethylation, carbamoylation, thiocarbamoylation, quaternization and reduction steps are conducted as reported above.

The preparation of the following heterocyclic aryl halide is reported in the literature.

2-Iodo-3-pyridinecarbonitrile (Journal of Organic Chemistry (2002), 67(26), 9276-9287);
4-Iodo-3-pyridinecarbonitrile (Journal of Organic Chemistry (2002), 67(26), 9276-9287);
5-Chloro-3-pyridinecarbonitrile (Journal of Organic Chemistry (1974), 39(13), 1802-7);
6-Bromo-3-pyridinecarbonitrile (Journal of Organic Chemistry, 2001, 66, 1500-1502);
2-Chloro-3-quinolinecarbonitrile (Tetrahedron 2001, 57, 3087-3098);
Ethyl 5-chloroquinoline-3-carboxylate (Tetrahedron Letters 2001, 42, 3737-3740);
Ethyl 6-bromoquinoline-3-carboxylate (Tetrahedron Letters 2002, 43, 6209-6211);
Ethyl 7-chloroquinoline-3-carboxylate (Tetrahedron Letters 2002, 43, 6209-6211);
Ethyl 8-bromoquinoline-3-carboxylate (NO Patent WO 2001047891);
1-Bromoisoquinoline (Journal of Medicinal Chemistry 2002, 45, 740-743);
Methyl 1-chloroisoquinoline-4-carboxylate (Indian Journal of Chemistry (1972), 10(4), 341-3);
3-Bromoisoquinoline (Synthesis, 1987, 8, 693-6);
4-Bromoisoquinoline (Chemical & Pharmaceutical Bulletin (1997), 45(5), 928-931;
5-Bromoisoquinoline (Journal of Medicinal Chemistry (2002), 45(17), 3660-3668);
6-Bromoisoquinoline (Bioorganic & Medicinal Chemistry Letters (2002), 12(5), 827-832);
7-Bromoisoquinoline (Bioorganic & Medicinal Chemistry Letters (2002), 12(15), 2043-2046;
8-Bromoisoquinoline (ARKIVOC [online computer file] (2000), 1(5), 823-842);

The preparation of the following arylboronic acids is reported in the literature;
2-Methoxyphenylboronic acid (New Journal of Chemistry (2002), 26(4), 373-375);
3-Methoxyphenylboronic acid (Organic Letters (2004), 6(21), 3711-3714);
4-Methoxyphenylboronic acid (Bioorganic & Medicinal Chemistry (2004), 12(10), 2553-2570);
4-Methoxy-1-naphthenyl boronate (Journal of the American Chemical Society (2000), 122(48), 12051-12052);
3-Methoxy-1-naphthylboronic acid (Journal of Organic Chemistry (1999), 64(26), 9430-9443);
2-(Methoxyphenyl)-1-naphthylboronic acid (Journal of Organic Chemistry (1999), 64(26), 9430-9443);
2-Methoxy-1-naphthylboronic acid (Organic Process Research & Development (2003), 7(3), 379-384);
1-Methoxy-2-naphthylboronic acid (Tetrahedron Letters (1999), 40(43), 9005-9007);
3-Methoxy-2-naphthylboronic acid (Tetrahedron Letters (1999), 40(43), 7599-7603);
6-Methoxy-2-naphthylboronic acid (Journal of Organic Chemistry (2004), 69(6), 2024-2032);

The biological activities of the products of general formula G and G+ have been evaluated.

Acetylcholinesterase (AChE) activity of both prodrugs of formula G and inhibitors of formula G+ was determined by a modified Ellman method.

The ability of prodrugs of formula G and/or inhibitors of formula G+ to nonselectively bind muscarinic receptors was evaluated with conventional radioligand binding method.

The results are showed in table 2 and demonstrate that the bioprecusor of formula G has no activity against human acetylcholinesterase while the compounds of formula G+ are very potent inhibitors with a very good in vitro activity as selective inhibitor of acetylcholinesterase.

Furthermore the compounds of formula G+ are very selective towards acetylcholinesterase compared to muscarinic receptors as demonstrated by the very low values for displacement of [$^3$H] N-methylscopolamine.

Moreover, prodrugs of formula G show no affinity with muscarinic receptors as proved by the very low values for displacement of [$^3$H] N-methylscopolamine from muscarinic receptors.

The Acute toxicity studies were carried out using female and male Swiss albinos mice (25-35 g). Most of the compounds show a very low toxicity, namely with a DL50 higher than 10 mg/kg. For example, compound 67 tested under its inclusion form as compound 82 shows an acute toxicity of 25 mg/kg. The pharmacokinetic study was carried out using female and male Swiss albinos mice for the determination of half-life and distribution volume of a compound of the invention.

The results show a very short plasmatic half-life time ($T_{1/2}$ less than 15 min) and a high apparent volume of distribution ($V_d$ no less than 42 L/kg with an intraperitoneal injection of 10 mg/kg of compound 67 under its inclusion form, example 82). Thus these values demonstrate that the compound of the invention has very rapidly diffused towards a lipophilic type organ (such as the brain).

These properties make said products as well as their salts with pharmaceutically acceptable acids and bases suitable for use as drugs in the treatment of diseases related to neurodegenerative diseases such as Alzheimer's disease, myasteny disease, light and early dementia.

Therefore one object of the present invention is, as prodrugs and in particular as anti-Alzheimer prodrugs, the products of formula G as defined above as well as their salts with pharmaceutically acceptable acids and bases. Another object of the invention is the drug of formula G+ which has been oxidised in the CNS and which acts in vivo in the CNS as a cholinesterase inhibitor.

An object of the invention is also the pharmaceutical compositions containing as active ingredient in a safe an effective amount, at least one of the compounds according to the invention as defined above. Due to their specific structural design, the compounds of the invention and specially those of formula G are stable enough to be formulated and stored before being administered to human.

These compositions can be administered by buccal, rectal, parenteral (in particular intramuscular route) or by local route as a topical application on the skin and the mucous membranes.

The compositions according to the invention can be solids or liquids and be presented in the pharmaceutical forms commonly used in human medicine, such as for example, plain or sugar-coated tablets, gelatin capsules, granules, suppositories, injectable preparations, ointments, creams, gels, transdermal patchess; they are prepared according to the usual methods. The active ingredient(s) can be incorporated with the excipients usually used in these pharmaceutical compositions, such as talc, arabic gum, lactose, starch, magnesium stearate, cocoa butter, aqueous or non aqueous vehicles, fatty substances of animal or vegetable origin, paraffin derivatives, glycols, various wetting, dispersing or emulsifying agents, preservatives.

These compositions can in particular be presented in the form of a powder intended to be dissolved extemporaneously in an appropriate vehicle, for example apyrogenic sterile water.

The dose administered is variable according to the condition treated, the patient in question, the administration route and the product considered. A safe an effective amount can be, for example, comprised between 0.01 mg and 300 mg, preferably between 0.1 mg and 100 mg per day by oral, intramuscular or intravenous route in adults or also comprised between 0.01 mg and 1 mg per hour by percutaneous route.

Another object of the invention is a pharmaceutical composition comprising a compound of formula G+, G1+, G2+ or G3+ as described above for its use as a acetylcholinesterase inhibitor in the PNS.

Such a pharmaceutical composition is unable to cross the BBB but can reach the PNS through the blood stream. The lack of undesirable central effects (confusion, hypothermia . . . ), make such a pharmaceutical composition a good candidate for the treatment of myasteny disease in a human or other animal subject.

Another object of the invention is an inclusion complex of the compound of formula G, G1a, G1b, G2, G3a, G3b in a beta-cyclodextrine.

This complex is prepared by dissolving the compound of the invention with a beta-cyclodextrine preferably a hydroxypropyl-betacyclodextrine, in a mixture of at least two organic solvents selected from the group comprising alcohol such as ethanol, methanol, a chlorinated solvent such as dichloromethane, at room temperature, preferentially between 15 and 55 degrees Celsius. Then the solvent is removed by evaporation or freeze drying.

After formation of this complex, solubility of a compound of formula G, G1a, G1b, G2, G3a, and G3b in water is increased and thus the inclusion complex can be formulated as a pharmaceutically acceptable aqueous solution for parenteral administration or intraperitoneal administration.

An another surprising advantage of the inclusion step of a compound of formula G, G1a, G1b, G2, G3a, G3b with a beta-cyclodextrine is its property of purification, namely, the impurities which are present in the starting compound of formula G, G1a, G1b, G2, G3a, G3b are removed after the inclusion step.

The compounds of the present invention have been prepared according to the procedures described below in the examples section.

The d distance in the compounds of the invention has been calculated by semiempirical methods (PM3) and are reported in table I a&b below.

TABLE 1a

| Example n° | d (nm) | Example n° | d nm |
|---|---|---|---|
| 1 | 0.59 | 34 | 0.46 |
| 2 | 0.61 | 35 | 0.46 |
| 3 | 0.59 (C5)-0.62 (C7) | 36 | 0.41 |
| 4 | 0.61-0.41 | 37 | 0.41 |
| 5 | 0.61 | 38 | 0.41 |
| 6 | 0.61 | 39 | 0.41 |
| 7 | 0.61 | 40 | 0.41 |
| 8 | 0.58 | 41 | 0.41 |
| 9 | 0.61 | 42 | 0.41 |
| 10 | 0.61 | 43 | 0.41 |
| 11 | 0.61 | 44 | 0.41 |
| 12 | 0.61 | 45 | 0.41 |
| 13 | 0.66 (C6)-0.54 (C7) | 46 | 0.41 |
| 14 | 0.66 (C6)-0.54 (C7) | 47 | 0.41 |
| 15 | 0.56 | 48 | 0.41 |
| 16 | 0.71 | 49 | 0.41 |
| 17 | 0.71 | 50 | 0.41 |
| 18 | 0.71 | 51 | 0.38 |
| 19 | 0.71 | 52 | 0.38 |
| 20 | 0.71 (C6)-0.46 (C8) | 53 | 0.3.8 |
| 21 | 0.71 (C6)-0.46 (C8) | 54 | 0.38 |
| 22 | 0.71 (C6)-0.46 (C8) | 55 | 0.38 |
| 23 | 0.71 (C6)-0.46 (C8) | 56 | 0.56 |
| 24 | 0.71 (C6)-0.46 (C8) | 57 | 0.39 |
| 25 | 0.71 (C6)-0.46 (C8) | 58 | 0.61 |
| 26 | 0.71 (C6)-0.46 (C8) | 59 | 0.43 |
| 27 | 0.46 | 60 | 0.56 |
| 28 | 0.46 | 61 | 0.52 |
| 29 | 0.46 | 62 | 0.64 |
| 30 | 0.46 | 63 | 0.52 |
| 31 | 0.46 | 64 | 0.47 |
| 32 | 0.46 | 65 | 0.47 |
| 33 | 0.46 | 66 | 0.47 |

TABLE 1b

| Example n° | d nm | Example n° | d nm |
|---|---|---|---|
| 67 | 0.61 | 74 | 0.39 |
| 68 | 0.60 | 75 | 0.59 |
| 69 | 0.60 | 76 | 0.60 |
| 70 | 0.60 | 77 | 0.39 |
| 71 | 0.56 | 78 | 0.59 |
| 72 | 0.66 | 79 | 0.43 |
| 73 | 0.60 (C5)-0.60 (C7) | 80 | 0.70 |

EXAMPLE 1

Preparation of ethyl 1-methyl-7-(N,N-dimethylcarbamate)-1,4-dihydroquinoline-3-carboxylate

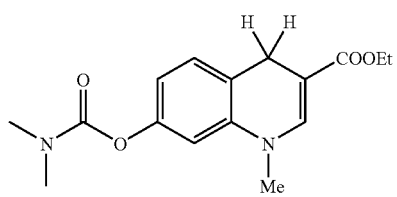

Stage A: 7-hydroxy 3-quinolinecarboxylic acid.

A solution of 3-cyano-7-methoxyquinoline (20 g, 110 mmol) [described in *Tetrahedron Lett.* 1998, 39 (23), 40134016] in 48% aqueous solution bromhydric acid (300 ml) is stirred and heated under reflux for 12 hours. The reaction mixture was then cooled to room temperature and neutralised by adding 20% aqueous KOH. The resulting precipitate was filtered and dried under vacuum. In this way 15.2 g (yield: 73%) of the product of molecular formula $C_{10}H_7NO_3$ was recovered. Aspect: brown powder.

Melting point: >260° C.

NMR Spectrum of the Proton

In DMSO-$d_6$ at 300 MHz, chemical shifts (ppm) and multiplicity: 13.28 (s, 1 H), 10.68 (s, 1 H), 9.20 (d, J=2 Hz, 1 H), 8.84 (d, J=2 Hz, 1 H), 8.06 (d, J=9 Hz, 1 H), 7.34 (s, 1 H), 7.29 (d, J=9 Hz, 1 H).

Stage B: ethyl 7-hydroxyquinoline-3-carboxylate

To a solution of the compound obtained in stage A (15 g, 79 mmol) in EtOH (500 ml) was added dropwise $SOCl_2$ (40 mL). The resulting mixture was stirred under reflux during 12 hours. After adding water (200 mL), the pH was adjusted to 7.0 with 20% aqueous $Na_2CO_3$. The aqueous solution was extracted with $CH_2Cl_2$ (3×200 mL). The combined organic layers were dried over $MgSO_4$, filtered and evaporated to afford 11 g (yield: 64%) of the product of molecular formula $C_{12}H_{11}NO_3$. Aspect: pale brown powder.

Melting point: 182° C.

NMR Spectrum of the Proton

In $CDCl_3$, at 300 MHz, chemicals shifts (ppm) and multiplicity: 9.24 (d, J=2 Hz, 1 H), 8.70 (d, J=2 Hz, 1 H), 7.66 (d, 9 Hz, 1 H), 7.36 (s, 1 H), 7.02 (dd, J=9 and 2 Hz, 1 H), 4.48 (q, J=7.1 Hz, 2 H), 1.48 (t, J=7.1 Hz, 3 H).

Stage C: ethyl 7-(N,N-dimethylcarbamate)quinoline-3-carboxylate

To a solution of compound obtained in stage B (300 mg, 1.38 mmol) in dry THF (20 mL) was added 72 mg (1.5 mmol) of NaH (50% dispersion in mineral oil). The mixture was stirred at room temperature for 1 hour after which time dimethylcarbamoyl chloride (140 L, 1.5 mmol) was added. The resulting mixture was refluxed for 12 hours. After addition of water (10 mL) and extraction with $CH_2Cl_2$ (3×15 mL), the resulting combined organic layers were dried over $MgSO_4$, filtered and evaporated under vacuum to give 360 mg (yield: 90%) of compound of molecular formula $C_{15}H_{16}N_2O_4$. Aspect: pale yellow powder.

Melting point: 98° C.

NMR Spectrum of the Proton

In $CDCl_3$, at 300 MHz, chemicals shifts (ppm) and multiplicity: 9.42 (d, J=2 Hz, 1 H), 8.80 (d, J=2 Hz, 1 H), 7.90 (d, J=9 Hz, 1 H), 7.85 (d, J=2 Hz, 1 H), 7.45 (dd, J=9 and 2 Hz, 1 H), 4.47 (q, J=7.1 Hz, 2 H), 3.15 (s, 3 H), 3.04 (s, 3 H), 1.44 (t, J=7.1 Hz, 1 H).

Stage D: ethyl 1-methyl-7-(N,N-dimethylcarbamate)quinolinium-3-carboxylate triflate To a solution of compound obtained in stage C (300 mg, 1.0 mmol) in dry $CH_2Cl_2$ (25 mL) was added methyl triflate (130 L, 1.1 mmol). The resulting solution was stirred at room temperature for 2 hours. Addition of $Et_2O$ (10 mL) furnished a white precipitate which was filtered to give the desired quinolinium salt of molecular formula $C_{17}H_{19}F_3N_2O_7S$ in a quantitative yield. Aspect: white powder.

Melting point: 193° C.

NMR Spectrum of the Proton

In $CDCl_3$, at 300 MHz, chemical shifts (ppm) and multiplicity: 9.78 (s, 1H, $H_4$), 9.44 (s, 1H, $H_2$), 8.35 (d, J=9 Hz, 1H, $H_6$), 8.28 (s, 1H, $H_8$), 7.87 (d, J=9 Hz, 1H, $H_5$), 4.74 (s, 3H, N-Me), 4.54 (q, J=7.1 Hz, 2H, $CH_2$-$CH_3$), 3.19 (s, 3H, N-methyl carbamate), 3.07 (s, 3H, $\overline{\text{N-methyl}}$ carbamate), 1.47 (t, J=7.1 Hz, 3H, $CH_2$—$CH_3$.

Stage E: ethyl N-methyl-7-(N,N-dimethylcarbamate-1,4-dihydroquinoline-3-carboxylate To a solution of the compound prepared in stage D (100 mg, 0.22 mmol) in water (6 ml) and $CH_2Cl_2$ (6 mL), were added in one portion sodium dithionite (190 mg, 1.1 mmol) and sodium carbonate (70 mg, 0.66 mmol). After stirring for 1 hour under a nitrogen atmosphere, $Na_2S_2O_4$ (190 mg, 1.1 mmol) and $Na_2CO_3$ (70 mg, 0.66 mmol) were added. After stirring for 1 hour, $Na_2S_2O_4$ (190 mg, 1.1 mmol) and $Na_2CO_3$ (70 mg, 0.66 mmol) were added and stirring was continued for an additional 1 hour. The aqueous layer was extracted with $CH_2Cl_2$ (3×15 ml), the combined organic layers were dried over $MgSO_4$, filtered and evaporated under vacuum to give 31 mg (yield: 47%) of the compound of molecular formula $C_{16}H_{20}N_2O_4$. Aspect: yellow oil.

NMR Spectrum of the Proton

In $CDCl_3$, at 300 MHz, chemicals shifts (ppm) and multiplicity: 7.19 (s, 1H, $H_2$), 7.00 (d, J=8.5 Hz, 1H, $H_5$), 6.67 (dd, J=9 Hz and 3 Hz, 1H, $H_6$), 6.49 (d, J=3 HZ, 1H, $H_8$), 4.17 (q, J=7.1 Hz, 2H, $CH_2$—$CH_3$), 3.73 (s, 2H, $H_4$), 3.18 (s, 3H, N-Me), 3.08 (s, $\overline{3H}$, N-methylcarbamate), 3.00 (s, 3H, N-methylcarbamate), 1.28 (t, J=7.1 Hz, 3H, $CH_2$—$CH_3$.

EXAMPLE 2

Preparation of ethyl 1-methyl-5-(N,N-dimethylcarbamate)-1,4-dihydroquinoline-3-carboxylate

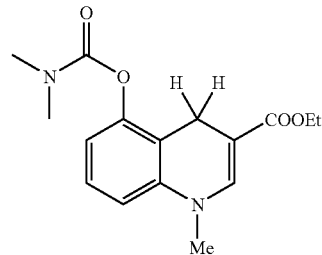

Stage A: 5-(benzyloxy)quinoline-3-carboxylic acid.

To a solution of 0.1 g (0.53 mmol) of compound prepared in stage B of example 67 in 5 mL of dry DMF was added 132 μL (1.11 mmol) of benzyl bromide and finely powdered $K_2CO_3$ (183 mg, 1.3 mmol). This mixture was stirred at 65° C. under $N_2$ for 36 hours. The reaction was worked up by pouring the solution into water (10 mL) and ethyl acetate (10 mL). The product was extracted with ethyl acetate (3×10 mL). The organic layers were combined, washed with water and brine, and dried over $MgSO_4$. Filtration and evaporation under vacuum gave 0.14 g of a viscous brown oil. This ester was treated with KOH (150 mg, 2.66 mmol) dissolved in 10 mL of ethanol and heated under reflux for 3 hours. After evaporation of ethanol, the product was dissolved in 5 mL of water and washed with diethyl ether (2×10 mL). The aqueous layer was neutralized with an aqueous solution of HCL 3M. The acid was filtered and dried under vacuum. 93 mg (yield: 63%) of compound of molecular formula $C_{17}H_{13}NO_3$ was obtained. Aspect: brown powder.

NMR Spectrum of the Proton

In DMSO-$d_6$ at 300 MHz, chemical shifts (ppm) and multiplicity: 9.30 (s, 1H), 9.04 (s, 1H), 7.83 (dd, J=8.5 and 7.9 Hz, 1H), 7.68 (d, J=8.5 Hz, 1H), 7.56 (d, J=7.0 Hz, 2H), 7.43 (m, 3H), 7.27 (d, J=7.7 Hz, 1H), 5.37 (s, 2H).

Stage B: Ethyl 5-(benzyloxy)quinoline-3-carboxylate.

1 g (3.58 mmol) of compound prepared in stage A was heated under reflux in 30 mL of thionyle chloride for 1 hour. After evaporation of thionyl chloride, the residue was dissolved in 50 mL of ethanol and 1.5 mL of dry triethylamine. The reaction mixture was then heated under reflux overnight and then evaporated. A purification by column chromatography on silica gel with dichloromethane/ethyl acetate (9/1) and 1% of triethylamine as eluent gave 210 mg (yield: 19%) of compound of molecular formula $C_{19}H_{17}NO_3$. Aspect: yellow powder.

NMR Spectrum of the Proton

In $CDCl_3$ at 300 MHz, chemical shifts (ppm) and multiplicity: 9.44 (s, 1H), 9.29 (s, 1H), 7.72 (m, 2H), 7.43 (m, 5H), 6.97 (dd, J=2.0 and 6.9 Hz, 1H), 5.29 (s, 2H), 4.46 (q, J=7.3 Hz, 2H), 1.45 (t, J=7.1 Hz, 3H).

Stage C: Ethyl 5-hydroxyquinoline-3-carboxylate.

210 mg (0.68 mmol) of compound prepared in stage B dissolved in 25 mL of ethanol was stirred in presence of Pd/$C_5$% (75 mg, 0.034 mmol) under an atmosphere of hydrogen for 3 hours. The palladium was then removed by filtration and ethanol was evaporated under reduced pressure. The $^1H$ NMR of the crude product showed a part of a reduced by-product at the pyridine ring (dihydroquinoline derivatives). The mixture was dissolved in ethanol and treated with air gas until complete re-oxidation of the product. Evaporation of the solvent gave 135 mg (yield: 91%) of compound of molecular formula $C_{12}H_{11}NO_3$. Aspect: yellow powder.

Melting point: 240° C. (degrad.)

NMR Spectrum of the Proton

In DMSO-$d_6$ at 300 MHz, chemical shifts (ppm) and multiplicity: 11.01 (s, 1H), 9.26 (d, J=2.3 Hz, 1H), 9.06 (d, J=1.9 Hz, 1H), 7.73 (dd, J=8.1 and 8.1 Hz, 1H), 7.54 (d, J=8.5 Hz, 1H), 7.04 (d, J=7.7 Hz, 1H), 4.40 (q, J=7.0 Hz, 2H), 1.38 (t, J=7.2 Hz, 3H).

Infrared Spectrum

IR spectrum was obtained as potassium bromide pellets. Absorption bands are given in $cm^{-1}$: 1713 (C=O), 1377, 1258, 1111.

Elemental Analyse

Anal. calcd for $C_{12}H_{11}NO_3$: C, 66.35; H, 5.10; N, 6.45. Found: C, 65.93; H, 5.46; N, 6.46%.

Stage D: Ethyl 5-(N,N-dimethylcarbamate)quinoline-3-carboxylate.

To a solution of 0.4 g (1.84 mmol) of compound prepared in stage C in 100 mL of acetone was added finely powdered $K_2CO_3$ (1.27 g, 9.22 mmol) and 203 µL (2.21 mmol) of N,N-dimethylcarbamoyl chloride. This mixture was heated under reflux overnight and then filtered. After evaporation of the solvent, a purification by column chromatography on silica gel with diethyl ether as eluent gave 415 mg (yield: 78%) of compound of molecular formula $C_{15}H_{16}N_2O_4$. Aspect: pale yellow powder.

Melting point: 99° C.

NMR Spectrum of the Proton

In $CDCl_3$ at 300 MHz, chemical shifts (ppm) and multiplicity: 9.40 (d, J=1.9 Hz, 1H), 8.89 (d, J=2.1 Hz, 1H), 7.98 (d, J=8.5 Hz, 1H), 7.76 (dd, J=7.7 and 8.5 Hz, 1H), 7.38 (d, J=7.7 Hz, 1H), 4.43 (q, J=7.0 Hz, 2H), 3.24 (s, 3H), 3.04 (s, 3H), 1.41, (t, J=7.2 Hz, 3H).

NMR Spectrum of the Carbon

In $CDCl_3$ at 75 MHz, chemical shifts (ppm) and nature of the carbon: 165.2 (C), 154.3 (C), 150.2 (CH), 147.8 (C), 133.0 (CH), 131.4 (CH), 126.6 (CH), 123.3 (C), 121.6 (C), 119.5 (CH), 61.6 ($CH_2$), 37.0 ($CH_3$), 36.7 ($CH_3$), 14.3 ($CH_3$).

Elemental Analyse

Anal. calcd for $C_{15}H_{16}N_2O_4$: C, 62.49; H, 5.59; N, 9.72. Found: C, 62.63; H, 5.45; N, 9.79%.

Infrared Spectrum

IR spectrum was obtained as potassium bromide pellets. Absorption bands are given in $cm^{-1}$: 1754, 1720, 1281, 1157.

Stage E: Ethyl 5-(N,N-dimethylcarbamate)-1-methylquinolinium-3-carboxylate triflate.

To 116 mg (0.40 mmol) of compound prepared in stage D dissolved in 10 mL of anhydrous dichloromethane was added, under $N_2$, 50 µL (0.44 mmol) of methyl trifluoromethanesulfonate. The reaction mixture was stirred overnight at room temperature. Evaporation of the solvent gave 174 mg (yield: 100%) of compound of molecular formula $C_{17}H_{19}F_3N_2O_7S$. Aspect: pale yellow powder.

Melting point: 170° C.

NMR Spectrum of the Proton

In $CDCl_3$ at 300 MHz, chemical shifts (ppm) and multiplicity: 9.89 (s, 1H), 9.58 (s, 1H), 8.31 (m, 2H), 7.87 (dd, J=2.5 and 6.2 Hz, 1H), 4.83 (s, 3H), 4.55 (q, J=7.2 Hz, 2H), 3.30 (s, 3H), 3.10 (s, 3H), 1.48 (t, J=7.2 Hz).

NMR Spectrum of the Carbon

In $CDCl_3$ at 75 MHz, chemical shifts (ppm) and nature of the carbon: 161.5 (C), 152.9 (C), 150.9 (CH), 149.8 (C), 142.5 (CH), 140.1 (C), 138.6 (CH), 124.6 (C), 124.0 (C), 123.3 (CH), 115.8 (CH), 63.8 ($CH_2$), 47.4 ($CH_3$), 37.4 ($CH_3$), 37.1 ($CH_3$), 14.2 ($CH_3$).

NMR Spectrum of the Fluor

In $CDCl_3$ at 282.5 MHz, chemical shifts (ppm): −78.9.

High Resolution Mass Spectrometry

HRMS (DCI+, isobutene): calcd for (M$^+$) $C_{16}H_{19}N_2O_4^+$: m/z 303.1345. Found: 303.1366.

Infrared Spectrum

IR spectrum was obtained as potassium bromide pellets. Absorption bands are given in $cm^{-1}$: 1751, 1732, 1259, 1155.

Stage F: Ethyl 5-(N,N-dimethylcarbamate)-1-methyl-1,4-dihydroquinoline-3-carboxylate.

0.1 g (0.23 mmol) of compound prepared in stage E and 49 mg (0.23 mmol) of N-benzyl-1,4-dihydronicotinamide (BNAH) were stirred at room temperature in 10 mL of dichloromethane for 12 hour. The reaction mixture was then washed with water (3×10 mL). The organic layer was separated, dried over $MgSO_4$, filtered and evaporated under reduced pressure at room temperature. 56 mg (yield: 80%) of compound of molecular formula $C_{16}H_{20}N_2O_4$ was obtained. Aspect: yellow powder.

NMR Spectrum of the Proton

In $CDCl_3$ at 300 MHz, chemical shifts (ppm) and multiplicity: 7.19 (s, 1H), 7.12 (dd, J=8.1 and 8.3 Hz, 1H), 6.75 (d, J=8.1 Hz, 1H), 6.57 (d, J=8.3 Hz, 1H), 4.18 (q, J=7.1 Hz, 2H), 3.63 (s, 2H), 3.11 (s, 3H), 3.00 (s, 3H), 1.29 (t, J=7.1 Hz, 3H).

EXAMPLE 3

Preparation of ethyl 1-methyl-5,7-di(N,N-dimethyl-carbamate)-1,4-dihydroquinoline-3-carboxylate

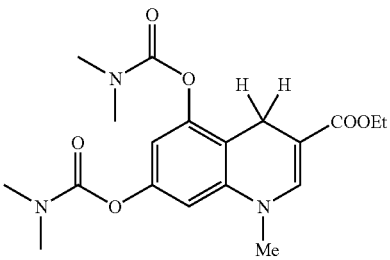

Stage A: 5,7-dihydroxy-3-quinolinecarboxylic acid

A solution of 3-cyano-5,7-methoxyquinoline (20 g, 110 mmol) [described in Tetrahedron Letters, 39 (23), 4013-4016, 1998] was treated as reported in stage A of Example 1. The compound of the molecular formula $C_{10}H_7NO_4$ (MW=205.17) is obtained in 80% yield.

Stage B: ethyl 5,7-dihydroxyquinoline-3-carboxylate.

The title compound is prepared as described in Stage B of Example 1

Stage C: ethyl 5,7-di(N,N-dimethylcarbamate)quinoline-3-carboxylate. The title compound is prepared as described in Stage C of Example 1.

Stage D: ethyl 1-methyl-5,7-di(N,N-dimethylcarbamate) quinolinium-3-carboxylate triflate The title compound is prepared as described in Stage D of Example 1.

Stage E: ethyl 1-methyl-5,7-di(N,N-dimethylcarbamate-1,4-dihydroquinoline-3-carboxylate.

The title compound is synthesized as described in Stage E of Example 1.

EXAMPLE 4

Preparation of ethyl 1-methyl-5,8-di(N,N-dimethyl-carbamate)-1,4-dihydroquinoline-3-carboxylate

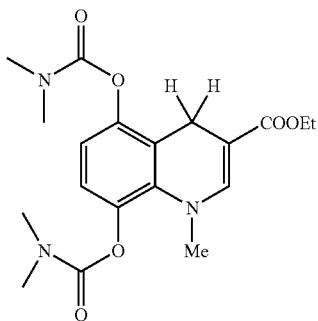

Stage A: 5,8-dihydroxy-3-quinolinecarboxylic acid

A solution of 3-cyano-5,8-methoxyquinoline (20 g, 110 mmol) [described in Tetrahedron Letters, 39 (23), 4013-4016, 1998] was treated as reported in stage A of Example 1. The compound of the molecular formula $C_{10}H_7NO_4$ (MW=205.17) is obtained in 80% yield.

Stage B: ethyl 5,8-dihydroxyquinoline-3-carboxylate.

The title compound is synthesized as described in Stage B of Example 1

Stage C: ethyl 5,8-di(N,N-dimethylcarbamate)quinoline-3-carboxylate.

The title compound is prepared as described in Stage C of Example 1.

Stage D: ethyl 1-methyl-5,8-di(N,N-dimethylcarbamate) quinolinium-3-carboxylate triflate The title compound is prepared as described in Stage D of Example 1.

Stage E: preparation of ethyl 1-methyl-5,8-di(N,N-dimethyl-carbamate-1,4-dihydroquinoline-3-carboxylate.

The title compound is synthesized as described in Stage E of Example 1.

EXAMPLE 5

Preparation of ethyl 1-methyl-1,4-dihydro-5-O-quinoline-N,N-dimethylthiocarbamate-3-carboxylate

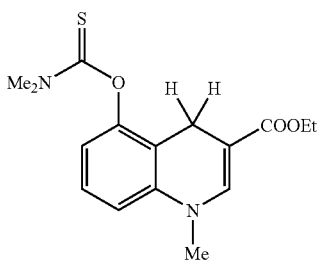

Stage A: ethyl N,N-(dimethylthiocarbamate)-5-O-quinoline-3-carboxylate

A solution of ethyl 5-hydroxyquinoline-3-carboxylate prepared in stage D of example 2 (21.7 g, 10 mmol) in DMF (40 ml) was cooled to 0°-5° C. and treated with 60% sodium hydride (300 mg, 12.5 mmol) and stirred 15 min. Dimethylthiocarbamoyl chloride (1.23 g, 10 mmol) was then added and the solution was stirred for 10 min at 5° C. and 30 min at room temperature then at 60° C. for 1 hour. The solution was cooled, diluted with 1N-sodium hydroxide solution and extracted with AcOEt (3×25 mL). The combined organic layers were washed with 1N-sodium hydroxide, brine, water, then brine, and dried over Magnesium sulfate and evaporated under reduced pressure. The obtained residue was chromatographed over silica-gel.

Stage B: ethyl 1-methyl-5-O-quinoliniumdimethylthiocarbamate-3-carboxylate triflate.

The title compound is synthesized as described in stage D of Example 1.

Stage C: ethyl 1-methyl-1,4-dihydro-5-O-quinolinedimethylthiocarbamate-3-carboxylate The title compound is prepared as described in stage E of Example 1.

EXAMPLE 6

Preparation of ethyl 1-methyl-1,4-dihydro-5-S-quinoline-N,N-dimethylthiocarbamate-3-carboxylate

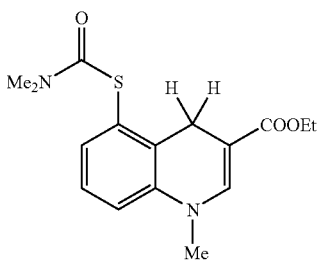

Stage A: ethyl (N,N-dimethylthiocarbamate)-5-S-quinoline-3-carboxylate ethyl (N,N-dimethylthiocarbamate)-5-O-quinoline-3-carboxylate prepared in stage A of example 5 was placed on a preheated oil bath at 210° C. and heated for 5 hours and cooled to room temperature. The solid residue was chromatographed on silica-gel.

Stage B: ethyl 1-methyl-(N,N-dimethylthiocarbamate)-5-S-quinolinium-3-carboxylate triflate.

The title compound is prepared as described in stage D of Example 1.

Stage C: ethyl 1-methyl-(N,N-dimethylthiocarbamate)-1,4-dihydro-5-S-quinoline-3-carboxylate The title compound is synthesized as described in stage E of Example 1.

EXAMPLE 7

Preparation of 1-methyl-5-(N,N-dimethylcarbamate)-3-(N, N-diethylcarboxamido)-1,4-dihydroquinoline

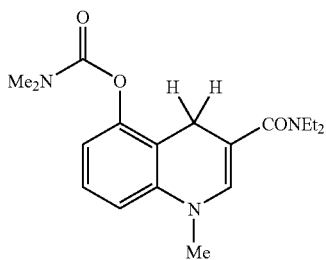

Stage A: ethyl 5-benzyloxyquinoline-3-carboxylate

A solution of ethyl 5-hydroxyquinoline-3-carboxylate (2.17 g, 10 mmol) prepared in stage D of example 2, Na$_2$CO$_3$ (2.12 g, 20 mmol) and benzylbromide (1.71 g, 10 mmol) in DMF (20 mL) was stirred for 12 hours at room temperature. The reaction mixture was diluted with water (50 mL) and then extracted with AcOEt (3×25 mL). The combined organic layers were washed water, and dried over Magnesium sulfate and evaporated under reduced pressure. The obtained residue was chromatographed over silica-gel.

Stage B: 5-benzyloxy-3-quinolinecarboxylic acid.

A solution of ethyl 5-benzyloxyquinoline-3-carboxylate (3.07 g, 10 mmol) prepared in stage A and LiOH (0.4 g, 20 mmol) in THF (20 mL) and water (0.5 mL) was refluxed for 2 hours. After cooling, the solvents were evaporated under vacuum. The solid residue was used in the next step without further purification.

Stage C: 5-benzyloxy-3-(N,N-diethylcarboxamido)quinoline

A solution of 5-benzyloxy-3-quinolinecarboxylic acid (2.80 g, 10 mmol) prepared in stage B, oxalyl chloride (1.2 g, 10 mmol) in dichloromethane (50 mL) was added 2 drops of DMF. The resultant mixture was stirred for 2 hours at room temperature after which time diethylamine (2.19 g, 30 mmol) was added. The resulting solution was stirred for a further 3 hours. The reaction mixture was diluted with water (50 mL) and then extracted with AcOEt (3×25 mL). The combined organic layers were washed water, and dried over Magnesium sulfate and evaporated under reduced pressure. The obtained residue was chromatographed over silica-gel.

Stage D: 5-hydroxy-3-(N,N-diethylcarboxamido)quinoline.

A solution of 5-benzyloxy-3-(N,N-diethylcarboxamido)quinoline (3.34 g, 10 mmol) prepared in stage C in methanol (50 mL) was added 10% Pd/C (400 mg). The solution was stirred for 24 hours at room temperature under a hydrogen atmosphere. The catalyst was filtered through a plug of cotton and washed with methanol. Evaporation of methanol afforded the desired compound.

Stage E: 5-(N,N-dimethylcarbamate)-3-(N,N-diethylcarboxamido)quinoline.

The title compound is prepared according to the procedure described in stage C of example 1.

Stage F: 1-methyl-5-(N,N-dimethylcarbamate)-3-(N, N-ethylcarboxamido)quinolium triflate.

The title compound is synthesized as described in stage D of example 1

Stage G: 1-methyl-5-(N,N-dimethylcarbamate)-3-(N,N-diethylcarboxamido)-1,4-dihydroquinoline.

The title compound is prepared as described in stage E of example 1.

EXAMPLE 8

Preparation of 1-methyl-7-(N,N-dimethylcarbamate)-3-(4,5-dihydro-4,4-dimethyl-2-oxazolyl)-1,4-dihydroquinoline

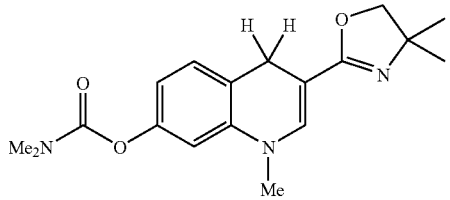

Stage A: 7-methoxy-3-(4,5-dihydro-4,4-dimethyl-2-oxazolyl)quinoline

A solution of 7-methoxy-3-cyanoquinoline reported in Tetrahedron Letters 39, 1998, 4013-4016 (1.84 g, 10 mmol) and 2-amino-2-methyl-1-propanol (0.90 g, 10 mmol) in chlorobenzene under nitrogen atmosphere is refluxed for 2 days.

The solvent is evaporated under vacuum to afford the desired compound

Stage B: 7-hydroxy-3-(4,5-dihydro-4,4-dimethyl-2-oxazolyl)quinoline

A solution of 7-methoxy-3-(4,5-dihydro-4,4-dimethyl-2-oxazolyl)quinoline (2.56 g, 10 mmol) prepared in stage A and BBr$_3$ (7.41 g, 30 mmol) in dichloromethane (40 mL) are stirred for 12 hours at room temperature. The mixture was quenched with saturated sodium hydrogen carbonate. Extraction with dichloromethane, drying (MgSO$_4$) and evaporation furnished the desired compound.

Stage C: 7-(N,N-dimethylcarbamate)-3-(4,5-dihydro-4,4-dimethyl-2-oxazolyl)quinoline The title compound is synthesized according to the procedure reported in stage C of example 1 from 7-hydroxy-3-(4,5-dihydro-4,4-dimethyl-2-oxazolyl)quinoline prepared in stage B.

Stage D: 1-methyl-7-(N,N-dimethylcarbamate)-3-(4,5-dihydro-4,4-dimethyl-2-oxazolyl)quinolinium triflate The title compound is prepared according to the procedure reported in stage D of example 1 from 7-(N,N-dimethylcarbamate)-3-(4,5-dihydro-4,4-dimethyl-2-oxazolyl)quinoline prepared in stage C.

Stage E 1-methyl-7-(N,N-dimethylcarbamate)-3-(4,5-dihydro-4,4-dimethyl-2-oxazolyl)-1,4-dihydroquinoline The title compound is prepared according to the procedure reported in stage E of example 1 from 1-methyl-7-(N,N-dimethylcarbamate)-3-(4,5-dihydro-4,4-dimethyl-2-oxazolyl)quinolinium triflate prepared in stage D.

EXAMPLE 9

Preparation of 1-methyl-5-(N,N-dimethylcarbamate)-3-trifluoromethyl-1,4-dihydroquinoline

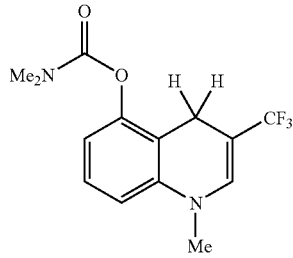

stage A: 5-methoxy-3-quinolinecarboxylic acid

A solution of ethyl 5-methoxyquinoline-3-carboxylate (2.31 g, 10 mmol) prepared in stage B of example 2 and LiOH (0.4 g, 20 mmol) in THF (20 mL) and water (0.5 mL) was refluxed for 2 hours. After cooling, the solvents were evaporated under vacuum. The solid residue was used in the next step without further purification.

stage B: 5-methoxy-3-trifluoromethylquinoline according to a procedure reported in the Journal of Organic chemistry, 1999, 64, 7053.

To a solution of 5-methoxy-3-quinolinecarboxylic acid (2 g, 10 mmol) prepared in stage A in dichloromethane was added bis(2-methoxyethyl)aminosulfur trifluoride (2.43 g, 11 mmol) under nitrogen and stirred for 16 hours at room temperature. The solution was poured into saturated NaHCO$_3$ and after CO$_2$ evolution ceased it was extracted with dichloromethane, dried, filtered and evaporated in vacuo. The resulting acyl fluoride intermediate (10 mmol) was added bis(2-methoxyethyl)aminosulfur trifluoride (4.42 g, 20 mmol)contained in a Teflon bottle equipped with a nitrogen inlet tube, and the mixture was heated at 85° C. On completion, the solution was poured into saturated NaHCO$_3$ and after CO$_2$ evolution ceased it was extracted with dichloromethane, dried, filtered and evaporated in vacuo to give 5-methoxy-3-trifluoromethyl quinoline Stage C: 5-hydroxy-3-trifluoromethylquinoline The title compound is prepared according to the procedure reported in stage B of example 8 from 5-methoxy-3-trifluoromethylquinoline prepared in stage B.

Stage D: 5-(N,N-dimethylcarbamate)-3-trifluoromethylquinoline

The title compound is prepared according to the procedure reported in stage C of example 1 from 5-hydroxy-3-trifluoromethylquinoline synthesized in stage C.

Stage E: 1-methyl 5-(N,N-dimethylcarbamate)-3-trifluoromethylquinolinium triflate The title compound is prepared according to the procedure reported in stage D of example 1 from 5-(N,N-dimethylcarbamate)-3-trifluoromethyl quinoline prepared in stage D.

Stage F: 1-methyl 5-(N,N-dimethylcarbamate)-3-trifluoromethyl-1,4-dihydroquinoline The title compound is prepared according to the procedure reported in stage E of example 1 from 1-methyl-5-(N,N-dimethylcarbamate)-3-trifluoromethylquinolinium triflate prepared in stage E

EXAMPLE 10

Preparation of (+/−)-1-methyl-3-(4-methylphenylsulfinyl)-5-(N,N-dimethylcarbamate)-1,4-dihydroquinoline

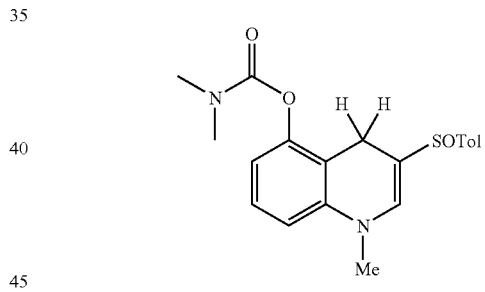

Stage A: 3-(tert-butoxycarbonylamino)-5-methoxyquinoline

To a solution of 5-methoxy-3-quinolinecarboxylic acid (2 g, 10 mmol) prepared in stage A of example 9 in tert-BuOH (15 mL) was added NEt$_3$ (1.2 g, 12 mmol) and diphenyl azidophosphonate (DPPA) (2.1 mL, 10 mmol). The reaction mixture is refluxed for 24 hours. The solvent is evaporated under vacuum and the residue is dissolved in AcOEt (50 mL) and washed with a saturated NaHCO$_3$ solution. After drying, the solvent is evaporated under vacuum affording the title compound.

Stage B: 3-bromo-5-methoxyquinoline

To a solution of 3-(tert-butoxycarbonylamino)-5-methoxyquinoline (2.74 g, 10 mmol) in aqueous 48% HBr (40 mL), NaNO$_2$ (2.1 g, 30 mmol) in water (20 mL) is added at 0° C. The reaction mixture is stirred 1 hour. The reaction mixture is extrated with CH$_2$Cl$_2$ (3×30 mL). After drying over MgSO$_4$, dichloromethane is evaporated affording the title compound.

Stage C: (+/−)-3-(4-methylphenylsulfinyl)-5-methoxyquinoline

To a solution 3-bromo-5-methoxyquinoline (2.37, 10 mmol) prepared in stage B in dried THF (35 mL) is added a solution of isopropylmagnesium chloride (16.6 mL, 30 mmol) at −78° C. The solution is stirred at −78° C. under nitrogen atmosphere for 3 hours. Menthyl sulfinate (8.8 g, 30 mmol) is added and the resulting solution is stirred for a further 24 hours. The reaction mixture is then hydrolysed with saturated aqueous NH$_4$Cl solution. After extraction of the aqueous phase, the combined organic layers are dried (MgSO4), evaporated giving the title compound.

Stage D: (+/−)-3-(4-methylphenylsulfinyl)-5-hydroxyquinoline

The title compound is synthesized according to the procedure reported in stage B of Example 8 from (+/−)-3-(4-methylphenylsulfinyl)-5-methoxyquinoline prepared in stage C.

Stage E: (+/−)-3-(4-methylphenylsulfinyl-5-(N,N-dimethylcarbamate) quinoline

The title compound is prepared according to the procedure reported in stage C of example 1 from (+/−)-3-(4-methylphenylsulfinyl-5-hydroxyquinoline prepared in stage D Stage F: (+/−)-1-methyl-3-(4-methylphenylsulfinyl)-5-(N,N-dimethylcarbamate)quinolinium triflate The title compound is synthesized according to the procedure reported in stage D of example 1 from (+/−)-3-(4-methylphenyl)sulfinyl)-5-(N,N-dimethylcarbamate) quinoline prepared in stage E.

Stage G: (+/−)-1-methyl-3-(4-methylphenylsulfinyl)-5-(N, N-dimethylcarbamate) 1,4-quinoline The title compound is prepared according to the procedure reported in stage E of example 1 from (+/−)-3-(4-methylphenylsulfinyl)-5-(N, N-dimethylcarbamate)quinolinium triflate prepared in stage F

EXAMPLE 11

Preparation of 1-methyl-3-(4-methylphenylsulfonyl)-5-(N, N-dimethylcarbamate)-1,4-dihydroquinoline

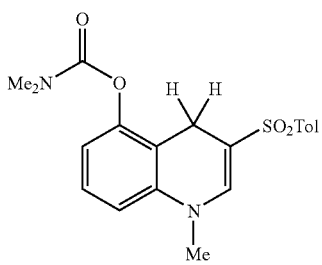

Stage A: 3-(4-methylphenylsulfonyl)-5-methoxyquinoline

To a solution of (+/−)-3-(4-methylphenylsulfinyl)-5-methoxyquinoline (2.97 g, 10 mmol) prepared in stage B of example 10 in CH$_2$Cl$_2$ is added m-CPBA (2.13 g, 80%, 10 mmol). The solution is stirred at room temperature for 12 hours. A solution of 1M NaOH is added. After extraction of the aqueous phase with CH$_2$Cl$_2$, the combined organic layers are dried (MgSO$_4$) and the solvent evaporated giving the title compound.

Stage B: 3-(4-methylphenylsulfonyl)-5-hydroxyquinoline

The title compound is synthesized according to the procedure reported in stage B of Example 9 from 3-(4-methylphenylsulfonyl)-5-methoxyquinoline prepared in stage A.

Stage C: 3-(4-methylphenylsulfonyl)-5-(N,N-dimethylcarbamate)quinoline

The title compound is prepared according to the procedure reported in stage C of Example 1 from 3-(4-methylphenylsulfonyl)-5-hydroxyquinoline prepared in stage Stage D: 1-methyl-3-(4-methylphenylsulfonyl)-5-(N, N-dimethylcarbamate)quinolinium triflate The title compound is prepared according to the procedure reported in stage D of example 1 from 3-(4-methylphenylsulfonyl)-5-(N,N-dimethylcarbamate)quinoline prepared in stage C Stage E: 1-methyl-3-(4-methylphenylsulfonyl)-5-(N, N-dimethylcarbamate)-1,4-dihydroquinoline.

The title compound is prepared according to the procedure reported in stage E of example 1 from 1-methyl-3-(4-methylphenylsulfonyl)$_5$-(N, N-dimethylcarbamate)quinolinium triflate prepared in stage D.

EXAMPLE 12

Preparation of 1-methyl-5-(N,N-dimethylcarbamate)-3-(N-phenylsulfomanide)-1,4-dihydroquinoline

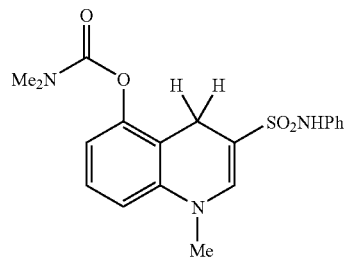

Stage A: 5-methoxy-3-methylthioquinoline

To a solution of 3-bromo-5-methoxy quinoline (2.37 g, 10 mmol) prepared in stage B of example 10 in THF (25 mL) was added 2.5M n-buLi (4 mL, 10 mmol) at −78° C. The solution is stirred at −78° C. for 45 min and dimethyl disulfide (1.8 g, 20 mmol) is added. The resultant solution is stirred for 3 hours and then quenched with saturated NH$_4$Cl (30 mL). Extraction with dichloromethane, drying, filtering and evaporation in vacuo afford the title compound Stage B: 3-(methylsulfinyl)-5-methoxyquinoline.

The title compound is prepared from 5-methoxy-3-methylthioquinoline (2.05 g, 10 mmol) prepared in stage A according the procedure reported in stage A of example 11.

Stage C: 5-methoxy-3-quinolinethiol.

To a solution of 3-(methylsulfinyl)-5-methoxyquinoline (2.21 g, 10 mmol) in CH$_2$Cl$_2$ (50 mL) is added TFAA. The resulting solution is stirred at 20-50° C. for 1 hour. The solution is then treated with NEt$_3$ affording the title compound.

Stage D: N-phenyl-5-methoxy-3-quinolinesulfomanide

A solution of 5-methoxy-3-quinolinethiol (1.91, 10 mmol) in AcOH is treated with chlorine for a few minutes. The solution is then treated with aniline (0.93 g, 10 mmol) to afford the title compound.

Stage E: N-phenyl-5-hydroxy-3-quinolinesulfomanide

The title compound is synthesized according to the procedure reported in stage B of Example 8 from N-phenyl-5-methoxy-3-quinolinesulfomanide prepared in stage D.

Stage F: 3-(N-phenylsulfomanide)-5-(N,N-dimethyl carbamate)quinoline

The title compound is prepared according to the procedure reported in stage C of Example 1 from N-phenyl-5-hydroxy-3-quinolinesulfonamide prepared in stage E.

Stage G: 1-methyl-3-(N-phenylsulfomanide)-5-(N,N-dimethylcarbamate)quinolinium triflate The title compound is prepared according to the procedure reported in stage D of Example 1 prepared from 3-(N-phenylsulfomanide)-5-(N,N-dimethyl carbamate)quinoline in stage F Stage H: 1-methyl-5-(N,N-dimethylcarbamate)-3-(N-phenylsulfomanide)-1,4-dihydroquinoline The title compound is prepared according to the procedure reported in stage E of Example 1 prepared from 1-methyl-3-(N-phenylsulfomanide)-5-(N,N-dimethyl carbamate)quinolinium triflate in stage G.

EXAMPLE 13

Preparation of 1-methyl-6,7-di(N,N-dimethylcarbamate)-3-nitro-1,4-dihydroquinoline

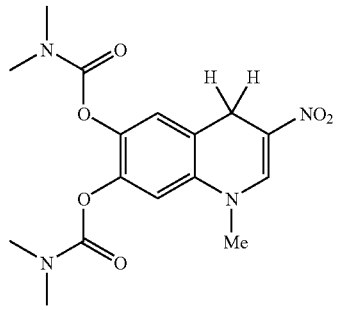

Stage A: 6,7-dihydroxy-3-nitroquinolin

The title compound is prepared according to the procedure reported in stage B of example 8 from 6,7-dimethoxy-3-nitroquinolin prepared according to a procedure described in the Journal of Medicinal Chemistry, 1994, 37, 2129.

Stage B: 1-methyl 6,7-di(N,N-dimethyl carbamate)-3-nitro-1,4-dihydroquinoline

The title compound is prepared from 6,7-dihydroxy-3-nitroquinolin prepared in stage A following the procedures in stage C, D and E of example 1.

EXAMPLE 14

Preparation of ethyl 1-methyl-2-phenyl-6,7-di(N,N-dimethylcarbamate)-1,4-dihydroquinoline-3-carboxylate

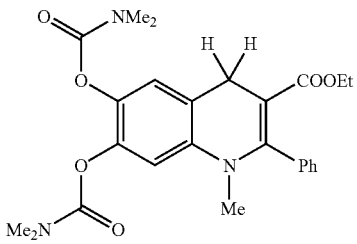

Stage A: 2-phenyl-6,7-hydroxy-3-quinolinecarboxylic acid

The title compound is prepared according the procedure reported in stage A of example 1 from ethyl 2-phenyl-6,7-methoxyquinoline-3-carboxylate prepared as reported in Organic Letters, 2003, 5, 3061-3063.

Stage B: ethyl 1-methyl-2-phenyl-6,7-di(N,N-dimethylcarbamate)-1,4-dihydroquinoline-3-carboxylate The title compound is prepared from 6,7-hydroxy-3-quinolinecarboxylic acid synthesized in stage A following the procedures in stage B, C, D and E of example 1.

EXAMPLE 15

Preparation of ethyl 1,2,4-trimethyl-7-(N,N-dimethylcarbamate)-1,4-dihydro-3-quinolinecarboxylate

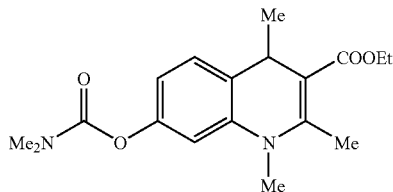

Stage A: ethyl 2,4-dimethyl-7-methoxy-3-quinolinecarboxylate

To a solution of 2-amino-6-methoxyacetophenone (1.65 g, 10 mmol) prepared as reported in the Journal of Medicinal Chemistry (1989), 32, 807-26 in ethanol (75 mL) is added ethyl 2-acetoacetate (1.3 g, 10 mmol) and a catalytic amount of $H_2SO_4$. The resultant solution is refluxed for 12 hours. The title compound is obtained after evaporation of the solvent.

Stage B: ethyl 1,2,4-trimethyl-7-(N,N-dimethylcarbamate)-1,4-dihydroquinoline-3-carboxylate The title compound is synthesized from ethyl 2,4-dimethyl-7-methoxyquinoline-3-carboxylate prepared in stage A following the procedures in stage A, B, C, D and E of example 1.

EXAMPLE 16

Preparation of 2-methyl-7-(N,N-dimethylcarbamate)-1,2-dihydroisoquinoline

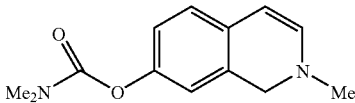

Stage A: 7-hydroxyisoquinoline

The title compound is prepared according to the procedure reported in stage A of Example 1 starting from 7-methoxyisoquinoline (1.6 g, 10 mmol) reported in Bioorganic and Medicinal Chemistry, 1999, 2647-2666.

Stage B: 2-methyl-7-(N,N-dimethylcarbamate)-1,2-dihydroisoquinoline

The title compound is prepared from 7-hydroxyisoquinoline prepared in stage A following the C, D and E of example 1.

EXAMPLE 17

Preparation of 2-methyl-7-(N,N-dimethylthiocarbamate)-1,2-dihydro-7-O-isoquinoline

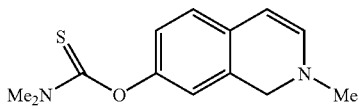

Stage A: 7-(N N-dimethylthiocarbamate)-7-O-isoquinoline

Starting from 7-hydroxyisoquinoline (1.45 g, 10 mmol) prepared in stage A of example 16, the title compound is prepared as described in stage A of example 5.
Stage B: 2-methyl-7-(N,N-dimethylthiocarbamate)-1,2-dihydro-7-O-isoquinoline The title compound is synthesized from 7-(N,N-dimethylthiocarbamate)-7-O-isoquinoline described in stage A following the procedure of stages D and E of example E.

EXAMPLE 18

Preparation of 2-methyl-7-(N,N-dimethylthiocarbamate)-1,2-dihydro-7-S-isoquinoline

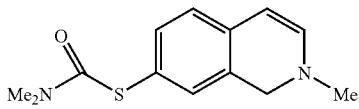

Stage A: 7-(N,N-dimethylthiocarbamate)-7-O-isoquinoline

The title compound is prepared according to the procedure reported in stage A of example 6, from 7-(N,N-dimethylthiocarbamate)-7-O-isoquinoline (2.23 g, 10 mmol) described in stage A of example 17.
Stage B: 2-methyl-7-(N,N-dimethylthiocarbamate)-1,2-dihydro-7-S-isoquinoline The title compound is prepared following the procedures reported in stages D and E of example 1 from 7-(N,N-dimethylthiocarbamate)-O-isoquinoline reported in stage A.

EXAMPLE 19

Preparation of 1,2-dimethyl-7-(N,N-dimethylthiocarbamate)-1,2-dihydro-7-O-isoquinoline

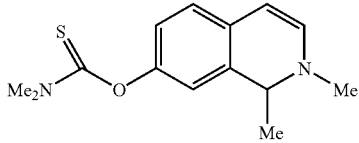

To a solution of 2-methyl-7-(N,N-dimethylthiocarbamate)-7-O-isoquinolinium triflate (3.8 g, 10 mmol), prepared in example 18, in THF (25 mL) is added a 2M solution of methylmagnesium bromide (5 mL, 10 mmol) at −78° C. under nitrogen atmosphere. The solution is stirred for 1 hour at this temperature. The solution is stirred a further 2 hours at 20° C. The reaction mixture is quenched with a saturated $NH_4Cl$ solution. After extraction with $CH_2Cl_2$, the combined organic layers are dried ($MgSO_4$), the organic solvents are evaporated under vacuum affording the title compound.

EXAMPLE 20

Preparation of ethyl 2,3-dimethyl-6,8-di(N,N-dimethylcarbamate)-1,2-dihydro-4-isoquinolinecarboxylate

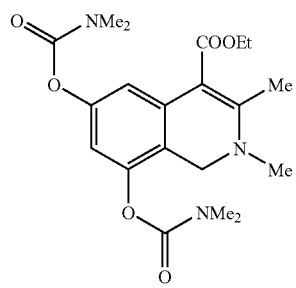

Stage A: 3-methyl 6,8-dihydroxy-3-isoquinolinecarboxylic acid

The title compound is prepared according the procedure reported in stage A of example 1 from 3-methyl-4-cyano-6,8-dimethoxyisoquinoline reported in Tetrahedron Letters, 1968, 44, 1160-1163.
Stage B: ethyl 2,3-dimethyl-6,8-di(N,N-dimethylcarbamate)-1,2-dihydro-4-isoquinolinecarboxylate The title compound is prepared from 3-methyl-6,8-dihydroxy-3-isoquinolinecarboxylic acid prepared in stage A following the stages B, C, D and E of example 1.

EXAMPLE 21

Preparation of 2,3-dimethyl-6,8-di(N,N-dimethylcarbamate)-1,2-dihydro-4-isoquinolinecarboxamide

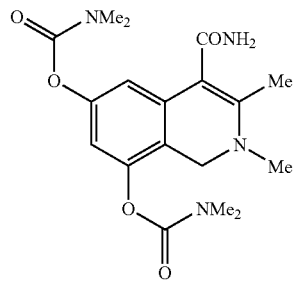

Stage A: 3-methyl-6,8-dimethoxy-4-isoquinolinecarboxamide 3-methyl-4-cyano-6,8-dimethoxyisoquinoline (2.28 g, 20 mmol) reported in Tetrahedron Letters, 1968, 44, 1160-1163 is added to a finely powdered urea-hydrogen peroxide adduct (1.88 g, 20 mmol) in a glass tube, and the reaction mixture is placed in an oil bath at 85° C. for 2 hours. After completion of the reaction, the reaction mixture is extracted with ethyl acetate and the combined extracts are washed with water and dried over anhydrous sodium sulfate. The solvent was removed under reduced pressure to afford the title compound.
Stage B: 2,3-dimethyl-6,8-di(N,N-dimethylcarbamate)-1,2-dihydro-4-isoquinolinecarboxamide The title compound is prepared from 3-methyl-6,8-dimethoxy-4-isoquinolinecarboxamide prepared in stage A following the procedures reported in stages B of example 8 and stages C, D and E of Example 1.

EXAMPLE 22

Preparation of 2,3-dimethyl-4-(4,5-dihydro-4,4-dimethyl-2-oxazolyl)-6,8-di(N,N-dimethylcarbamate)-1,2-dihydroisoquinoline

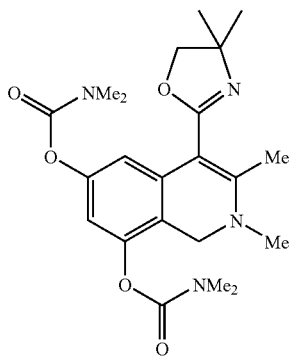

The title compound is prepared from 3-methyl-4-cyano-6,8-dimethoxyisoquinoline (2.28 g, 20 mmol) reported in Tetrahedron Letters, 1968, 44, 1160-1163 following the procedures reported in stages A and B of example 8, and in stages C, D, E of example 1.

EXAMPLE 23

Preparation of (+/−)-2,3-dimethyl-4-(4-methylphenylsulfinyl)-6,8-di(N,N-dimethylcarbamate)-1,2-dihydroisoquinoline

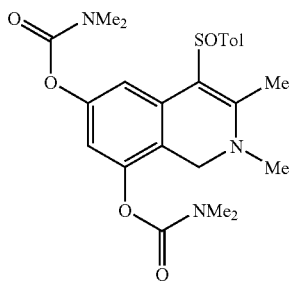

Stage A: 3-methyl-6,8-dimethoxy-4-isoquinolinecarboxylic acid

The title compound is prepared from 3-methyl-4-cyano-6,8-dimethoxy isoquinoline (2.28 g, 20 mmol) reported in Tetrahedron Letters, 1968, 44, 1160-1163, following the procedure reported in stage A of example 9

Stage B: (+/−)-3-methyl-(4-methylphenylsulfinyl)-6,8-dimethoxy-4-isoquinoline

The title compound is prepared from 3-methyl-6,8-dimethoxy-4-isoquinolinecarboxylic acid prepared in stage A following the procedures reported in stages A, B and C of example 10
Stage C: (+/−)-2,3-dimethyl-4-(4-methylphenylsulfinyl)-6,8-di(N,N-dimethylcarbamate)-1,2-dihydroisoquinoline The title compound is prepared from (+/−)-3-methyl-(4-methylphenylsulfinyl)-6,8-dimethoxy-4-isoquinoline prepared in stage B, following the procedures reported in stage B of example 8 and stage C, D and E of Example 1.

EXAMPLE 24

Preparation of 2,3-dimethyl-4-[4-(methyl)phenylsulfonyl]-6,8-di(N,N-dimethylcarbamate)-1,2-dihydroisoquinoline

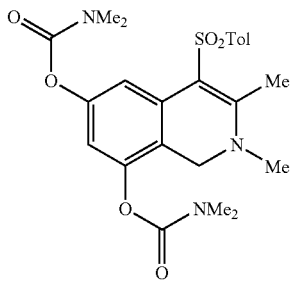

Stage A: (+/−)-3-methyl-(4-methylphenylsulfonyl)-6,8-dimethoxy-4-isoquinoline.

The title compound is prepared from (+/−)-3-methyl-(4-methylphenylsulfinyl)-6,8-dimethoxy-4-isoquinoline prepared in stage B of example 23 following the procedure reported in stage A of example 11.
Stage B: (+/−)-2,3-dimethyl-4-(4-methylphenylsulfonyl)-6,8-di(N,N-dimethylcarbamate)-1,2-dihydroisoquinoline.

The title compound is prepared from (+/−)-3-methyl-4-(4-methylphenylsulfonyl)-6,8-dimethoxyisoquinoline prepared in stage A, following the procedures reported in stages B of example 9, stages C, D, E of example 1.

EXAMPLE 25

Preparation of 2,3-dimethyl-4-(N-phenylsulfonamide)-6,8-di(N, N-dimethylcarbamate)-1,2-dihydroisoquinoline

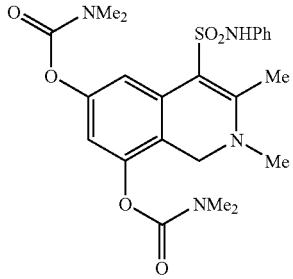

Stage A: 3-methyl-4-bromo-6,8-dimethoxy isoquinoline

The title compound is prepared according the procedure reported in stage A of example 9 from 3-methyl-6,8-dimethoxy-4-isoquinolinecarboxylic acid prepared in stage A of example 23.

Stage B: 3-methyl-4-(methylthio)-6,8-dimethoxy isoquinoline

The title compound is prepared according the procedure reported in stage A of example 12 from 3-methyl-4-bromo-6,8-dimethoxy isoquinoline prepared in stage A Stage C: 3-methyl-4-(methylsulfinyl)-6,8-dimethoxy isoquinoline The title compound is prepared according the procedure reported in stage B of example 12 from 3-methyl-4-(methylthio)-6,8-dimethoxy isoquinoline prepared in stage B Stage D: 3-methyl-6,8-dimethoxy-4-isoquinolinethiol The title compound is prepared according the procedure reported in stage C of example 12 from 3-methyl-4-(methylsulfinyl)-6,8-dimethoxy isoquinoline prepared in stage C Stage E: N-phenyl-3-methyl-6,8-dimethoxy-4-isoquinolinesulfonamide The title compound is prepared from 3-methyl-6,8-dimethoxy-4-isoquinolinethiol of stage D according the procedure reported in stage D of example 12

Stage F N-phenyl-3-methyl-6,8-hydroxy-4-isoquinolinesulfonamide

The title compound is prepared from N-phenyl-3-methyl-6,8-dimethoxy-4-isoquinolinesulfonamide of stage E according the procedure reported in stage B of example 8

Stage G 2,3-dimethyl-4-(N-phenylsulfonamide)-6,8-di(N,N-dimethylcarbamate)-1,2-dihydroisoquinoline.

The title compound is prepared according to the procedures reported in stages C, D and E of example 1.

EXAMPLE 26

Preparation of 2,3-dimethyl-4-(trifluoromethyl)-6,8-di(N, N-dimethylcarbamate)-1,2-dihydroisoquinoline

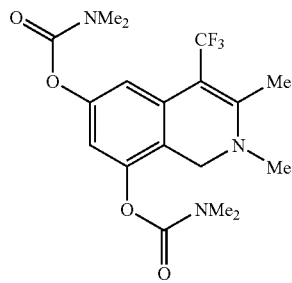

Stage A: 3-methyl-4(trifluoromethyl)-6,8-dimethoxy isoquinoline

The title compound is prepared from 3-methyl-6,8-dimethoxy-4-isoquinolinecarboxylic acid obtained in Stage A of example 23, according to the procedure reported in stage B of example 9.

Stage B: 3-methyl-4(trifluoromethyl)-6,8-dihydroxy isoquinoline

The title compound is synthesized according the procedure reported in stages B of example 8 from 3-methyl-4(trifluoromethyl)-6,8-dimethoxy isoquinoline obtained in stage A.

Stage C: 2,3-dimethyl-4-(trifluoromethyl)-6,8-di(N,N-dimethylcarbamate)-1,2-dihydroisoquinoline The title compound is synthesized according the procedure reported in stages stage C, D and E of example 1 from 3-methyl-4(trifluoromethyl)-6,8-dihydroxy isoquinoline obtained in stage B.

EXAMPLE 27

Preparation of ethyl 1-methyl-5-(N,N-dimethylcarbamate)-1,4-dihydropyridine-3-carboxylate

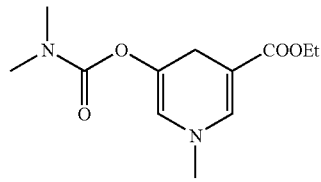

Stage A: ethyl 5-hydroxypyridine-3-carboxylate

The title compound is synthesized according to the procedure reported in stage B of example 8 from 5-methoxypyridine-3-carboxylate described in the Journal of Medicinal Chemistry, 2000, 43, 3168-3185.

Stage B ethyl 5-(N,N-dimethylcarbamate) pyridine-3-carboxylate

The title compound is synthesized following the procedure reported in stage C of example 1 from ethyl 5-hydroxy pyridine-3-carboxylate obtained in stage A.

Stage C: ethyl 1-methyl-5-(N,N-dimethylcarbamate)pyridinium-3-carboxylate triflate The title compound is prepared according to the procedure described in stage D of example 1 from ethyl 5-(N,N-dimethylcarbamate)pyridine-3-carboxylate obtained in stage B.

Stage D: ethyl 1-methyl-5-(N,N-dimethylcarbamate)-1,4-dihydropyridine-3-carboxylate The title compound is prepared according to the procedure described in stage E of example 1 from Ethyl 1-methyl-5-(N,N-dimethylcarbamate)pyridinium-3-carboxylate triflate obtained in stage C.

EXAMPLE 28

Preparation of ethyl 1-methyl-5-(N,N-dimethylthiocarbamate)-1,4-dihydro-5-O-pyridine-3-carboxylate

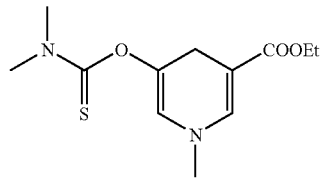

Stage A: ethyl 5-(N N-dimethylthiocarbamate)-5-O-pyridine-3-carboxylate

The title compound is prepared according to the procedure reported in stage A of example 5 from ethyl 5-hydroxypyridine-3-carboxylate obtained in stage A of example 27.

Stage B: ethyl 1-methyl-5-(N,N-dimethylthiocarbamate)-1,4-dihydro-5-O-pyridine-3-carboxylate The title compound is synthesized according to the procedures reported in stage D and E of example 1 from ethyl 5-(N,N-dimethylthiocarbamate)-5-O-pyridine-3-carboxylate obtained in stage A.

EXAMPLE 29

Preparation of ethyl 1-methyl-5-(N,N-dimethylthiocarbamate)-1,4-dihydro-5-S-pyridine-3-carboxylate

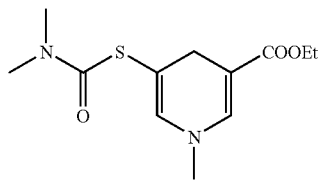

Stage A: ethyl 5-(N,N-dimethylthiocarbamate)-5-S-pyridine-3-carboxylate

The title compound is synthesized according the procedure described in A of example 6 from ethyl 5-(N,N-dimethylthiocarbamate)-5-O-pyridine-3-carboxylate prepared in example 28.

Stage B: Ethyl 1-methyl-5-(N,N-dimethylthiocarbamate)-5-S-pyridinium-3-carboxylate triflate The title compound is prepared following the procedure reported in stage D of example 1 from ethyl 1-methyl 5-(N,N-dimethylthiocarbamate)-5-S-pyridinium-3-carboxylate prepared in stage A Stage C: preparation of ethyl 1-methyl-5-(N,N-dimethylthiocarbamate)-1,4-dihydro-5-S-pyridine-3-carboxylate The title compound is prepared according the procedure reported in the stage E of example 1 from ethyl 1-methyl-5-(N,N-dimethylthiocarbamate)-5-S-pyridinium-3-carboxylate triflate prepared in stage B

EXAMPLE 30

Preparation of 1-methyl-3-(methylsulfonyl)-5-(N,N-dimethylcarbamate)-1,4-dihydropyridine

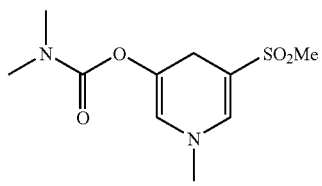

Stage A: 1-methyl-3-(methylsulfonyl)-5-(N,N-dimethylcarbamate)pyridinium triflate The title compound is synthesized according the procedures described in stages A, C and D of example 1 from 3-methoxy-5-(methylsulfonyl)pyridine reported in Tetrahedron, 1985, pages 173-1384.

Stage B: preparation of 1-methyl-3-(methylsulfonyl)-5-(N,N-dimethylcarbamate)-1,4-dihydropyridine The title compound is synthesized according the procedure reported in stage E of example 1 from 1-methyl-3-(methylsulfonyl)-5-(N N-dimethylcarbamate)pyridinium triflate prepared in stage 1.

EXAMPLE 31

Preparation of 1-methyl-3-(N N-diethylcarboxamido)-5-(N, N-dimethylcarbamate)-1,4-dihydropyridine

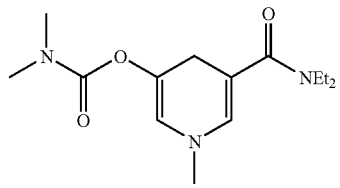

Stage A: 3-(N,N-diethylcarboxamido)-5-methoxy pyridine

The title compound is synthesized according the procedure reported in stages B and C of example 7 from ethyl 5-methoxypyridine-3-carboxylate described in the Journal of medicinal chemistry, 2000, 43, 3168-3185.

Stage B: 1-methyl-3-(N,N-diethylcarboxamido)-5-(N,N-dimethylcarbamate) pyridinium triflate The title compound is synthesized according the procedure described in stage B of example 8 and in stage C and D of example 1 from 3-(N,N-diethylcarboxamido)-5-methoxypyridine obtained in stage A.

Stage C: 1-methyl-3-(N,N-diethylcarboxamido)-5-(N; N-dimethylcarbamate)-1,4-dihydropyridine The title compound is prepared following the procedure reported in stage E of example 1 from 1-methyl-3-(N,N-diethylcarboxamido)-5-(N,N-dimethylcarbamate)pyridinium triflate prepared in stage B

EXAMPLE 32

Preparation of (+/−)-1-methyl-3-(methylsulfinyl)-5-(N, N-dimethylcarbamate)-1,4-dihydropyridine

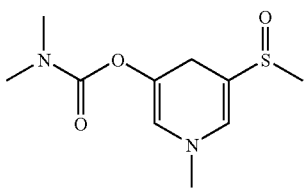

Stage A: (+/−)-1-methyl-3-(methylsulfinyl)-5-(N,N-dimethylcarbamate) pyridinium triflate The title compound is synthesized according the procedure reported in stage A, C and D of example 1 from (+/−)-3-methoxy-5-(methylsulfinyl)pyridine described in Phosphorus, Sulfur and Silicon and the Related Elements, 1992, 66, 127-137.

Stage B: (+/−)-1-methyl-3-(methylsulfinyl)-5-(N,N-dimethylcarbamate)-1,4-dihydropyridine The title compound is prepared according the procedure reported in stage E of example 1 from (+/−)-1-methyl-3-(methylsulfinyl)-5-(N,N-dimethylcarbamate)pyridinium triflate obtained in stage A.

EXAMPLE 33

Preparation of 1-methyl-3-(trifluoromethyl)-5-(N,N-dimethylcarbamate)-1,4-dihydropyridine

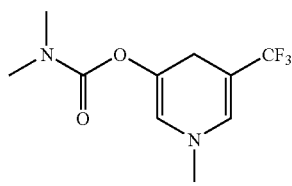

Stage A: 3-methoxy-5-trifluoromethylpyridin

To a solution of 3-bromo-5-trifluoromethylpyridin (2.25 g 10 mmol, prepared as described in Eur. J. Org. Chem. 2002, 327-330, in DMF was added sodium methoxide (0.8 g, 15 mmol). The resultant solution is stirred for 20 hours at 40° C. The title compound is obtained after evaporation of the solvent under vacuum.

Stage B: 1-methyl-3-(trifluoromethyl)-5-(N,N-dimethylcarbamate)pyridinium triflate The title compound is synthesized following the procedures reported in stage B of example 8 and in stages C and D of example 1 from 3-methoxy-5-trifluoromethylpyridin prepared in stage A Stage C: 1-methyl-3-(trifluoromethyl)-5-(N N-dimethylcarbamate)-1,4-dihydropyridine The title compound is synthesized following the procedure in stage E of example 1 from 1-methyl-3-(trifluoromethyl)-5-(N,N-dimethylcarbamate)pyridinium triflate prepared in stage B.

EXAMPLE 34

Preparation of 1-methyl-3-(4,5-dihydro-4,4-dimethyl-2-oxazolyl)-5-(N,N-dimethylcarbamate)-1,4-dihydropyridine

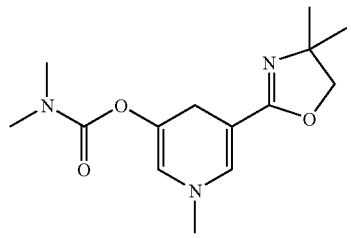

Stage A. 3-(4,5-dihydro-4,4-dimethyl-2-oxazolyl)-5-methoxypyridine

The title compound is prepared according to the procedure reported in stage A of example 8 from 3-cyano-5-methoxypyridine prepared as reported in the Journal of Medicinal Chemistry, 2000, 43, 3168-3185.

Stage B: 1-methyl-3-(4,5-dihydro-4,4-dimethyl-2-oxazolyl)-5-(N,N-dimethylcarbamate)pyridinium triflate.

The title compound is synthesized as reported in stage B of example 8 from 3-(4,5-dihydro-4,4-dimethyl-2-oxazolyl)-5-methoxypyridine affording 3-(4,5-dihydro-4,4-dimethyl-2-oxazolyl)-5-hydroxypyridine as an intermediate which is subsequently treated as described in stage C and D of example 1 to furnish 1-methyl-3-(4,5-dihydro-4,4-dimethyl-2-oxazolyl)-5-(N,N-dimethylcarbamate)pyridinium triflate.

Stage C: 1-methyl-3-(4,5-dihydro-4,4-dimethyl-2-oxazolyl)-5-(N,N-dimethylcarbamate)-1,4-dihydropyridine The title compound is obtained according to the procedure reported in stage E of example 1 from 1-methyl-3-(4,5-dihydro-4,4-dimethyl-2-oxazolyl)-5-(N, N-dimethylcarbamate) pyridinium triflate obtained in stage B.

EXAMPLE 35

Preparation of N,N-diethyl-1-methyl-5-(N,N-dimethylcarbamate)-1,4-dihydro-3-pyridinesulfonamide

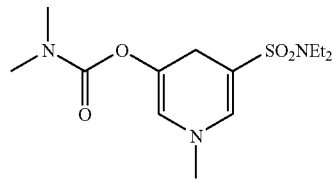

Stage A: N,N-diethyl-5-methoxy-3-pyridinesulfonamide

The title compound is synthesized according to the procedures in stage C and D of example 12 from (+/−)-3-(methylsulfinyl)-5-methoxypyridine described in Phosphorus, Sulfur and Silicon and the Related Elements, 1992, 66, 127-137 and diethylamine.

Stage B: N,N-diethyl-1-methyl-5-(N,N-dimethylcarbamate)-3-pyridiniumsulfonamide triflate The title compound is prepared following the procedures in stage B, C and D of example 1 from N,N-diethyl-5-methoxy-3-pyridinesulfonamide prepared in stage A.

Stage C: N,N-diethyl-1-methyl-5-(N,N-dimethylcarbamate)-1,4-dihydro-3-pyridinesulfonamide The title compound is synthesized following the procedure in stage E of example 1 from N,N-diethyl-1-methyl-5-(N,N-dimethylcarbamate)-3-pyridiniumsulfonamide triflate obtained in stage B.

EXAMPLE 36

Preparation of ethyl 1-[2-(N,N-dimethylcarbamate)benzyl]-1,4-dihydro-3-pyridinecarboxylate

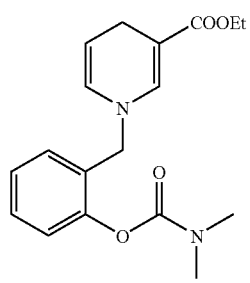

Stage A: ethyl 1-[2-(N,N-dimethylcarbamate)benzyl]-3-pyridiniumcarboxylate chloride To a solution of ethyl nicotinate (1.51 g, 10 mmol) in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: ethyl 1-[2-(N,N-dimethylcarbamate)benzyl]-1,4-dihydro-3-pyridinecarboxylate The title compound is synthesized according to the procedure reported in stage E of example 1 from ethyl 1-[2-(N,N-dimethylcarbamate)benzyl]-3-pyridiniumcarboxylate chloride prepared in stage A.

EXAMPLE 37

Preparation of 1-[2-(N,N-dimethylcarbamate)benzyl]-3-(methylcarbamoyl)-1,4-dihydropyridine

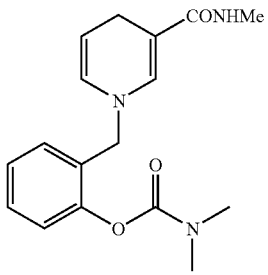

Stage A: 1-[2-(N,N-dimethylcarbamate)benzyl]-3-(methylcarbamoyl)pyridinium chloride To a solution of 3-(methylcarbamoyl)pyridine (1.36 g, 10 mmol) described in Synthetic Communication, 1982, 12, 989-993 in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-3-(methylcarbamoyl)-1,4-dihydropyridine The title compound is synthesized according to the procedure reported in stage E of example 1 from 1-[2-(N,N-dimethylcarbamate)benzyl]-3-(methylcarbamoyl)-pyridinium chloride prepared in stage A.

EXAMPLE 38

Preparation of 1-[2-(N,N-dimethylcarbamate)benzyl]-3-(4,5-dihydro-4,4-dimethyl-2-oxazolyl)-1,4-dihydropyridine

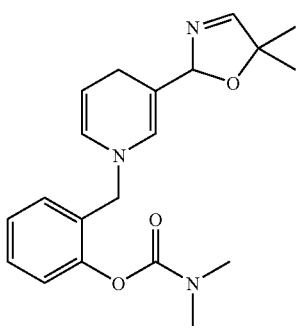

Stage A: 1-[2-(N,N-dimethylcarbamate)benzyl]-3-(4,5-dihydro-4,4-dimethyl-2-oxazolyl)pyridinium chloride To a solution of 3-(4,5-dihydro-4,4-dimethyl-2-oxazolyl)pyridine (1.76 g, 10 mmol) described in Tetrahedron Letters, 1998, 39, 459-462 in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: preparation of 1-[2-(N,N-dimethylcarbamate)benzyl]-3-(4,5-dihydro-4,4-dimethyl-2-oxazolyl)-1,4-dihydropyridine.

The title compound is synthesized according to the procedure reported in stage E of example 1 from 1-[2-(N,N-dimethylcarbamate)benzyl]-3-(4,5-dihydro-4,4-dimethyl-2-oxazolyl)-pyridinium chloride prepared in stage A.

EXAMPLE 39

Preparation of N,N-diethyl-1-[2-(N,N-dimethylcarbamate)benzyl]-1,4-dihydro-3-pyridinesulfonamide

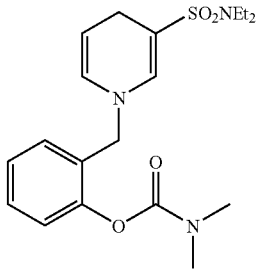

Stage A: N,N-diethyl-1-[2-(N,N-dimethylcarbamate)benzyl]-3-pyridiniumsulfonamide chloride To a solution of N,N-diethyl-3-pyridinesulfonamide (2.14 g, 10 mmol) described in the Journal of Organic Chemistry 2003, 68, 8274-8276 in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: N,N-diethyl-1-[2-(N,N-dimethylcarbamate)benzyl]-1,4-dihydro-3-pyridinesulfonamide The title compound is synthesized according to the procedure reported in stage E of example 1 from N,N-diethyl-1-[2-(N,N-dimethylcarbamate)benzyl]-3-pyridiniumsulfonamide chloride prepared in stage A.

EXAMPLE 40

Preparation of ethyl 1-[2-(N,N-dimethylcarbamate)benzyl]-1,4-dihydro-3-quinolinecarboxylate

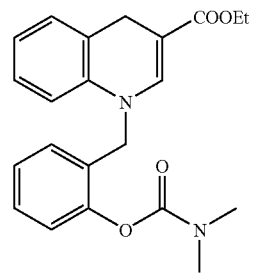

Stage A: ethyl 1-[2-(N,N-dimethylcarbamate)benzyl]-3-quinoliniumcarboxylate chloride To a solution of ethyl 3-quinolinecarboxylate (2.01 g, 10 mmol) in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: ethyl 1-[2-(N,N-dimethylcarbamate)benzyl]-1,4-dihydro-3-quinolinecarboxylate The title compound is synthesized according to the procedure reported in stage E of example 1 from ethyl 1-[2-(N,N-dimethylcarbamate)benzyl]-3-quinoliniumcarboxylate chloride prepared in stage A.

EXAMPLE 41

Preparation of 1-[2-(N,N-dimethylcarbamate)benzyl]-1,4-dihydro-3-(dimethylcarbamoyl)-quinoline

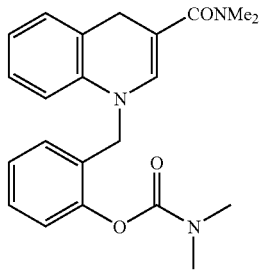

Stage A: 1-[2-(N,N-dimethylcarbamate)benzyl]-3-(dimethylcarbamoyl)quinolinium chloride To a solution of 3-(dimethylcarbamoyl)quinoline (2.0 g, 10 mmol) in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-1,4-dihydro-3-(methylcarbamoyl)quinoline The title compound is synthesized according to the procedure reported in stage E of example 1 from 1-[2-(N,N-dimethylcarbamate)benzyl]-3-(dimethylcarbamoyl)quinolinium chloride prepared in stage A.

EXAMPLE 42

Preparation of 1-[2-(N,N-dimethylcarbamate)benzyl]-1,4-dihydro-3-(4,5-dihydro-4,4-dimethyl-2-oxazolyl)quinoline

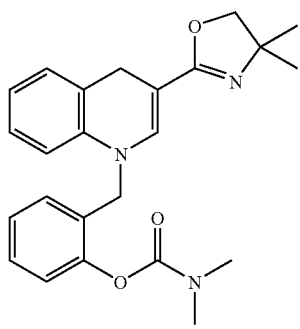

Stage A: 1-[2-(N,N-dimethylcarbamate)benzyl]-3-(4,5-dihydro-4,4-dimethyl-2-oxazolyl)quinolinium chloride.

To a solution of 3-(4,5-dihydro-4,4-dimethyl-2-oxazolyl)quinoline described in Synthesis, 1987, 693-696 (2.26 g, 10 mmol) in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-1,4-dihydro-3-(4,5-dihydro-4,4-dimethyl-2-oxazolyl)quinoline The title compound is synthesized according to the procedure reported in stage E of example 1 from 1-[2-(N,N-dimethylcarbamate)benzyl]-3-(4,5-dihydro-4,4-dimethyl-2-oxazolyl)quinolinium chloride prepared in stage A.

EXAMPLE 43

Preparation of N,N-dimethyl-1-[2-(N,N-dimethylcarbamate)benzyl]-1,4-dihydro-3-quinolinesulfonamide

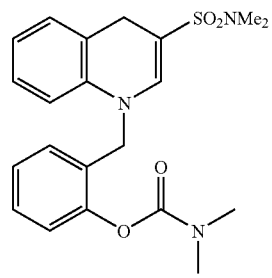

Stage A: N,N-dimethyl-3-quinolinesulfonamide

The title compound is synthesized according to the procedure reported in stage A of example 2 from N,N-dimethyl-4-chloro-3-quinolinesulfonamide reported in Heterocycle, 1997, 45, 2015-2021.

Stage B: N,N-dimethyl-1-[2-(N,N-dimethylcarbamate)benzyl]-3-quinolininiumsulfonamide chloride.

To a solution of N,N-dimethyl-3-quinolinesulfonamide, obtained in stage A, in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage C: N,N-dimethyl-1-[2-(N,N-dimethylcarbamate)benzyl]-1,4-dihydro-3-quinolinesulfonamide The title compound is synthesized according to the procedure reported in stage E of example 1 from N,N-dimethyl-1-[2-(N,N-dimethylcarbamate)benzyl]-3-quinolininiumsulfonamide chloride prepared in stage B.

EXAMPLE 44

Preparation of ethyl 2-[2-(N,N-dimethylcarbamate)benzyl]-1,2-dihydro-4-isoquinolinecarboxylate

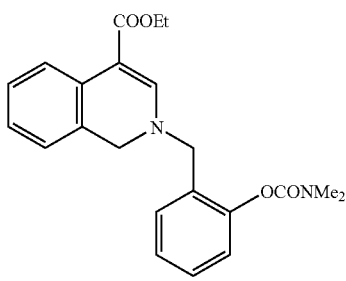

Stage A: ethyl 2-[2-(N,N-dimethylcarbamate)benzyl]-4-isoquinoliniumcarboxylate chloride To a solution of ethyl 3-isoquinolinecarboxylate described in Tetrahedron: Asymmetry, 2003, 14, 3469-3477 (2.01 g, 10 mmol) in a proper solvent (acetonitrile, DMF, EtOH, acetone) is to added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: ethyl 2-[2-(N,N-dimethylcarbamate)benzyl]-1,2-dihydro-4-isoquinolinecarboxylate The title compound is synthesized according to the procedure reported in stage E of example 1 from ethyl 2-[2-(N,N-dimethylcarbamate)benzyl]-4-isoquinoliniumcarboxylate chloride prepared in stage A.

EXAMPLE 45

Preparation of 2-[2-(N,N-dimethylcarbamate)benzyl]-4-(N—-phenethylcarbamoyl)-1,2-dihydroisoquinoline

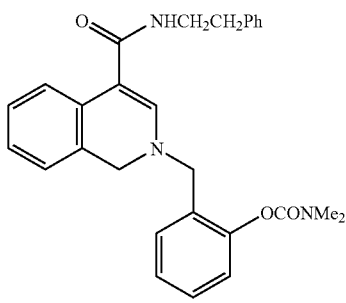

Stage A: 2-[2-(N,N-dimethylcarbamate)benzyl]-4-(N-phenethylcarbamoyl)isoquinolinium chloride.

To a solution of 4-(N—-phenethylcarbamoyl)isoquinoline described in Arch. Pharm. Pharm. Med. Chem., 2003, 336, 258-263 in a proper solvent (acetonitrile, DMF, EtOH, acetone) is added carbamic acid, dimethyl-, 2-(chloromethyl) phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 2-[2-(N N-dimethylcarbamate)benzyl]-4-(N—-phenethylcarbamoyl)-1,2-dihydroisoquinoline The title compound is synthesized according to the procedure reported in stage E of example 1 from 2-[2-(N,N-dimethylcarbamate)benzyl]-4-(N-phenethylcarbamoyl)isoquinolinium chloride prepared in stage A.

EXAMPLE 46

2-[2-(N,N-dimethylcarbamate)benzyl]-4-(4,5-dihydro-4,4-dimethyl-2-oxazolyl)-1,2-dihydroisquinoline

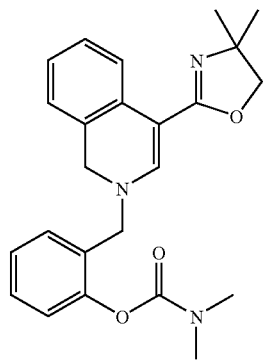

Stage A: 2-[2-(N,N-dimethylcarbamate)benzyl]-4-(4,5-dihydro-4,4-dimethyl-2-oxazolyl)isoquinolinium chloride To a solution of 4-(4,5-dihydro-4,4-dimethyl-2-oxazolyl)isoquinoline described in Tetrahedron Letters, 1986, 27, 5269-5270 (2.26 g, 10 mmol) in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 2-[2-(N,N-dimethylcarbamate)benzyl]-4-(4,5-dihydro-4,4-dimethyl-2-oxazolyl)-1,2-dihydroisoquinoline The title compound is synthesized according to the procedure reported in stage E of example 1 from 2-[2-(N,N-dimethylcarbamate)benzyl]-4-(4,5-dihydro-4,4-dimethyl-2-oxazolyl)isoquinolinium chloride obtained in stage A.

EXAMPLE 47

Preparation of N,N-diethyl-2-[2-(N,N-dimethylcarbamate)benzyl]-1,2-dihydro-4-isoquinolinesulfonamide

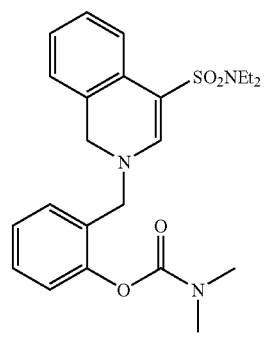

Stage A: N,N-diethyl-2-[2-(N,N-dimethylcarbamate)benzyl]-4-isoquinoliniumsulphonamide To a solution of N,N-diethyl-4-isoquinolinesulfonamide (2.64 g, 10 mmol) described in the Journal of Organic Chemistry 2003, 68, 8274-8276 in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: N,N-diethyl-2-[2-(N,N-dimethylcarbamate)benzyl]-1,2-dihydro-4-isoquinolinesulfonamide The title compound is synthesized according to the procedure reported in stage E of example 1 from N,N-diethyl-2-[2-(N,N-dimethylcarbamate)benzyl]-4-isoquinoliniumsulphonamide obtained in stage A.

EXAMPLE 48

Preparation of 1-[2-(N,N-dimethylcarbamate)benzyl]-3-(trifluoromethyl)-1,4-dihydropridine

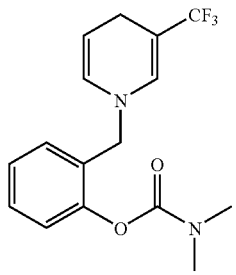

Stage A: 1-[2-(N,N-dimethylcarbamate)benzyl]-3-(trifluoromethyl)pyridinium chloride To a solution of 3-(trifluoromethyl)pyridine (1.47 g, 10 mmol) described in Eur. J. Org. Chem. 2003, 327-330 in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-3-(trifluoromethyl)-1,4-dihydropyridine.

The title compound is synthesized according to the procedure reported in stage E of example 1 from 1-[2-(N,N-dimethylcarbamate)benzyl]-3-(trifluoromethyl)pyridinium chloride obtained in stage A.

EXAMPLE 49

Preparation of 1-[2-(N,N-dimethylcarbamate)benzyl]-3-(trifluoromethyl)-1,4-dihydroquinoline

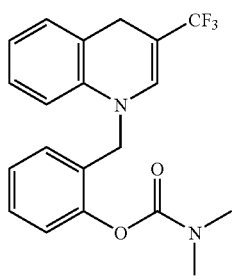

Stage A: 1-[2-(N,N-dimethylcarbamate)benzyl]-3-(trifluoromethyl)quinolininium chloride To a solution of 3-(trifluoromethyl)quinoline (1.97 g, 10 mmol) described in Journal of the Chemical Society, Chemical Communications (1992), (1), 53-54, in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-3-(trifluoromethyl)-1,4-dihydroquinoline.

The title compound is synthesized according to the procedure reported in stage E of example 1 from 1-[2-(N,N-dimethylcarbamate)benzyl]-3-(trifluoromethyl)quinolininium chloride obtained in stage A.

EXAMPLE 50

Preparation of 1-[2-(N,N-dimethylcarbamate)benzyl]-3-trifluromethyl)-1,2-dihydroisquinoline

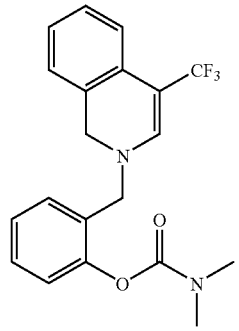

Stage A: 1-[2-(N,N-dimethylcarbamate)benzyl]-3-(trifluoromethyl)isoquinolinium chloride To a solution of 3-(trifluoromethyl)quinoline (1.97 g, 10 mmol), described in Bulletin of the Chemical Society of Japan (1988), 61(10), 3531-7, in a proper solvent (acetonitrile, DMF, EtOH, acetone) is added carbamic acid, dimethyl-, 2-(chloromethyl)phenyl ester (2.13 g, 10 mmol) reported in Chemical Papers 1985, 39, 413-27. The resultant solution is stirred for 24 hours at the correct temperature (25° C.-120° C.). The solvent is evaporated to furnish the title compound.

Stage B: 1-[2-(N,N-dimethylcarbamate)benzyl]-3-(trifluoromethyl)-1,2-dihydroisoquinoline.

The title compound is synthesized according to the procedure reported in stage E of example 1 from 1-[2-(N,N-dimethylcarbamate)benzyl]-3-(trifluoromethyl)isoquinolinium chloride prepared in stage A.

EXAMPLE 51

Preparation of ethyl 1-methyl-2-[2-(N,N-dimethyl-carbamate)phenyl]-1,4-dihydro pyridine-3-carboxylate

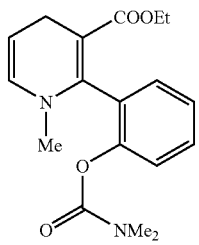

Stage A: ethyl 2-(2-methoxyphenyl)pyridine-3-carboxylate

A solution of ethyl 2-chloronicotitiate (1.85 g, 10 mmol), 2-methoxyphenylboronic acid (1.22 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.

Stage B: ethyl 1-methyl-2-[2-(N,N-dimethylcarbamate)phenyl]pyridininium-3-carboxylate triflate The title compound is prepared according to the procedures in stages A, B, C, D of example 1 from ethyl 2-(2-methoxyphenyl)pyridine carboxylate prepared in stage A.

Stage C: ethyl 1-methyl-2-[2-(N,N-dimethylcarbamate)phenyl]-1,4-dihydropyridine-3-carboxylate The title compound is prepared according to the procedure in stage E of example 1 from ethyl 1-methyl-2-[2-(N,N-dimethylcarbamate)phenyl]pyridininium-3-carboxylate triflate prepared in stage B.

EXAMPLE 52

Preparation of 1-methyl-2-[2-(N,N-dimethylcarbamate)phenyl]-1,4-dihydro-N,N-dimethylnicotinamide

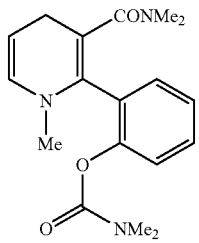

Stage A: 2-(2-methoxyphenyl)-N,N-dimethylnicotinamide

The title compound is prepared according the procedure reported in stage A of example 51 from 2-chloro-N,N-dimethylnicotinamide described in the Journal of Medicinal Chemistry (1989), 32(9), 2178-99.

Stage B: 1-methyl-2-[2-(N,N-dimethylcarbamate)phenyl]-3-(N, N-dimethylcarbamoyl)pyridinium triflate.

The title compound is synthesized following the procedure reported in stage B of example 8 from 2-(2-methoxyphenyl)-N,N-dimethylnicotinamide and stages C and D of example 1.

Stage C: 1-methyl-2-[2-(N N-dimethylcarbamate)phenyl]-1,4-dihydro-N,N-dimethylnicotinamide.

The title compound is synthesized following the procedure reported in stage E of example 1 from 1-methyl-2-[2-(N,N-dimethylcarbamate)phenyl]-3-(N, N-dimethylcarbamoyl) pyridinium triflate prepared in stage B.

EXAMPLE 53

Preparation of 1-methyl-2-[2-(N,N-dimethylcarbamate)phenyl]-3-(methylsulfonyl)-1,4-dihydropyridine

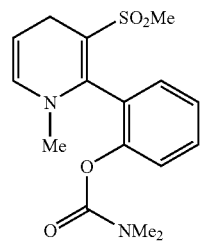

Stage A: 2-(2-methoxyphenyl)-3-(methylsulfonyl)pyridine

The title compound is synthesized following the procedure reported in stage A of example 51 from 2-chloro-3-(methylsulfonyl)pyridine described in the Journal of Organic Chemistry (1979), 44, 3080-3082.

Stage B: 1-methyl-2-[2-(N,N-dimethylcarbamate)phenyl]-3-(methylsulfonyl)pyridinium triflate The title compound is prepared according to the procedures reported in stages A, B, C, D of example 1 from 2-(2-methoxyphenyl)-3-(methylsulfonyl)pyridine obtained in stage A.

Stage C: 1-methyl-2-[2-(N,N-dimethylcarbamate)phenyl]-3-(methylsulfonyl)-1,4-dihydropyridine The title compound is prepared according to the procedure reported in stage E of example 1 from 1-methyl-2-[2-(N,N-dimethylcarbamate)phenyl]-3-(methylsulfonyl)pyridinium triflate obtained in stage A.

EXAMPLE 54

Preparation of N-methyl-1-methyl-2-[2-(N,N-dimethylcarbamate)phenyl]-1,4-dihydro-3-pyridinesulfonamide

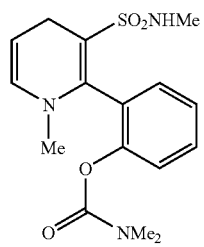

Stage A: N-methyl-2-(2-methoxyphenyl)-3-pyridinesulfonamide

The title compound is synthesized according the procedure described in stage A of example 51 from N-methyl-2-chloro-3-pyridinesulfonamide (1.72 g, 10 mmol) reported in Memoires de l'Academie Royale de Medecine de Belgique (1974), 47(3), 131-210.

Stage B: N-methyl-1-methyl-2-[2-(N,N-dimethylcarbamate) phenyl]-3-pyridiniumsulfonamide triflate The title compound is prepared according to the procedures in stages A, B, C, D of example 1 from N-methyl-2-(2-methoxyphenyl)-3-pyridinesulfonamide prepared in stage A
Stage C: N-methyl-1-methyl-2-[2-(N,N-dimethylcarbamate) phenyl]-1,4-dihydro-3-pyridinesulfonamide The title compound is synthesized according the procedure described in stage E of example 1 from N-methyl-1-methyl-2-[2-(N,N-dimethylcarbamate)phenyl]-3-pyridiniumsulfonamide triflate prepared in stage B.

EXAMPLE 55

Preparation of ethyl 1-methyl-6-[2-(N,N-dimethylcarbamate)phenyl]-1,4-dihydropyridine-3-carboxylate

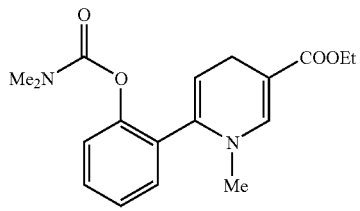

Stage A: 6-(2-methoxyphenyl)nicotinonitrile

A solution of ethyl 6-bromonicotinonitrile (1.81 g, 10 mmol) described in the Journal of Organic Chemistry 2001, 66, 1500-1502, 2-methoxyphenylboronic acid (1.22 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.
Stage B: ethyl 1-methyl-6-[2-(N,N-dimethylcarbamate)phenyl]pyridininium-3-carboxylate triflate The title compound is prepared according to the procedures in stages A, B, C, D of example 1 from 6-(2-methoxyphenyl)nicotinonitrile prepared in stage A.
Stage C: ethyl 1-methyl-6-[2-(N,N-dimethylcarbamate)phenyl]-1,4-dihydropyridine-3-carboxylate The title compound is prepared according to the procedure reported in stage E of example 1 from ethyl 1-methyl-6-[2-(N,N-dimethylcarbamate)phenyl]pyridininium-3-carboxylate triflate prepared in stage B.

EXAMPLE 56

Preparation of ethyl 1-methyl-5-[2-(N,N-dimethylcarbamate)phenyl]-1,4-dihydro pyridine-3-carboxylate

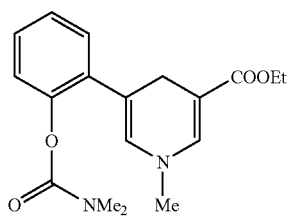

Stage A: ethyl 5-(2-methoxyphenyl)pyridine-3-carboxylate

A solution of ethyl 5-bromonicotinate (2.29 g, 10 mmol), prepared as reported in the Journal of Medicinal Chemistry 1995, 38, 1608-28, 2-methoxy phenyl boronic acid (1.22 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.
Stage B: ethyl 1-methyl-5-[2-(N,N-dimethylcarbamate)phenyl]pyridininium-3-carboxylate triflate.

The title compound is prepared according to the procedures reported in stages A, B, C, D of example 1 from ethyl 5-(2-methoxyphenyl)pyridine carboxylate prepared in stage A.
Stage C: preparation of ethyl 1-methyl-5-[2-(N, N-dimethylcarbamate)phenyl]-1,4-dihydropyridine-3-carboxylate.

The title compound is prepared according to the procedure described in stage E of example 1 from ethyl 1-methyl-5-[2-(N,N-dimethylcarbamate)phenyl]pyridininium-3-carboxylate triflate prepared in stage B.

EXAMPLE 57

Preparation of ethyl 1-methyl-2-[2-(N,N-dimethylcarbamate)phenyl]-1,4-dihydroquinoline-3-carboxylate

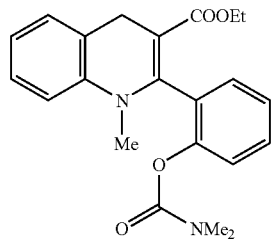

Stage A: ethyl 2-(2-methoxyphenyl)quinoline-3-carboxylate

A solution of ethyl 2-chloroquinoline-3-carboxylate (2.01 g, 10 mmol), prepared as described in the Journal of Organic Chemistry 2003, 68, 9517-9520, 2-methoxyphenylboronic acid (1.22 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.
Stage B: ethyl 1-methyl-2-[2-(N,N-dimethylcarbamate)phenyl]quinolinium-3-carboxylate triflate.

The title compound is prepared according to the procedures reported in stages A, B, C, D of example 1 from ethyl 2-(2-methoxyphenyl)quinoline-3-carboxylate prepared in stage A.
Stage C: preparation of ethyl 1-methyl-2-[2-(N,N-dimethylcarbamate)phenyl]-1,4-dihydroquinoline-3-carboxylate.

The title compound is prepared according to the procedure described in stage E of example 1 from ethyl 1-methyl-2-[2-

(N,N-dimethylcarbamate)phenyl]quinolinium-3-carboxylate triflate prepared in stage B.

EXAMPLE 58

Preparation of ethyl 1-methyl-8-[2-(N,N-dimethylcarbamate)phenyl]-1,4-dihydroquinoline-3-carboxylate

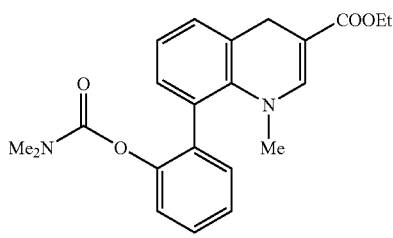

Stage A: ethyl 8-(2-methoxyphenyl)quinoline-3-carboxylate.

A solution of ethyl 8-bromoquinoline-3-carboxylate (2.01 g, 10 mmol), prepared as described in Patent WO 2001047891, 2-methoxyphenylboronic acid (2.79 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.

Stage B: ethyl 1-methyl-8-[2-(N,N-dimethylcarbamate)phenyl]quinolinium-3-carboxylate triflate.

The title compound is prepared according to the procedures reported in stages A, B, C, D of example 1 from ethyl 8-(2-methoxyphenyl)quinoline-3-carboxylate prepared in stage A.

Stage C: ethyl 1-methyl-8-[2-(N,N-dimethylcarbamate)phenyl]-1,4-dihydroquinoline-3-carboxylate.

The title compound is prepared according to the procedure reported in stage E of example 1 from ethyl 1-methyl-8-[2-(N,N-dimethylcarbamate)phenyl]quinolinium-3-carboxylate triflate prepared in stage B.

EXAMPLE 59

Preparation of 1-[2-(N,N-dimethylcarbamate)phenyl]-2-methyl-1,2-dihydroisoquinoline

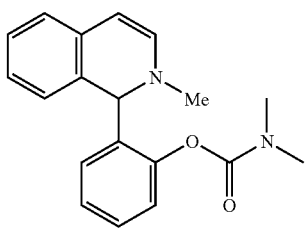

Stage A: 1-(2-methoxyphenyl)isoquinoline.

A solution of 1-bromoisoquinoline (2.06 g, 10 mmol), prepared as described in European Journal of Organic Chemistry 2002, 4181-4184, 2-methoxyphenylboronic acid (2.79 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.

Stage B: 1-[2-(N,N-dimethylcarbamate)phenyl]-2-methylisoquinolinium triflate.

The title compound is prepared according to the procedures reported in stages A, B, C, D of example 1 from 1-(2-methoxyphenyl)isoquinoline prepared in stage A.

Stage C: 1-[2-(N,N-dimethylcarbamate)phenyl]-2-methyl-1,2-dihydroisoquinoline.

The title compound is prepared according to the procedure reported in stage E of example 1 from 1-[2-(N,N-dimethylcarbamate)phenyl]-2-methylisoquinolinium triflate prepared in stage B.

EXAMPLE 60

Preparation of 2-methyl-4-[2-(N,N-dimethylcarbamate)phenyl]-1,2-dihydroisoquinoline

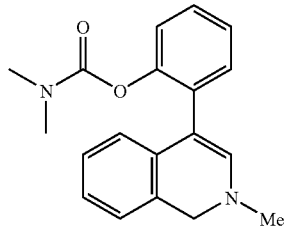

Stage A: 4-(2-methoxyphenyl) isoquinoline.

A solution of 4-bromoisoquinoline (2.06 g, 10 mmol), prepared as described in the Journal of Organic Chemistry 2003, 68, 9412-9415, 2-methoxyphenylboronic acid (2.79 g, 10 mmol), Pd(PPh$_3$)$_4$ (5% mol), K$_2$CO$_3$ (5 g) in DMF/water (3/1) is stirred at 50° C. for 12 hours. The reaction mixture is then pored on water (150 mL). The aqueous phase is extracted with ethyl acetate (3×100 mL). The combined organic layers are washed with water (3×200 mL). The organic phase is dried over magnesium sulfate and evaporated under vacuum to afford the title compound.

Stage B: 4-[2-(N,N-dimethylcarbamate)phenyl]-2-methylisoquinolinium triflate.

The title compound is prepared according to the procedures reported in stages A, B, C, D of example 1 from 4-(2-methoxyphenyl) isoquinoline prepared in stage A.

Stage C: 4-[2-(N,N-dimethylcarbamate)phenyl]-2-methyl-1,2-dihydroisoquinoline.

The title compound is prepared according to the procedure reported in stage E of example 1 from 4-[2-(N,N-dimethylcarbamate)phenyl]-2-methylisoquinolinium triflate obtained in stage B.

EXAMPLE 61

Preparation of ethyl 1-methyl-7-(N,N-dimethylcarbamate)-1,2-dihydroquinoline-3-carboxylate

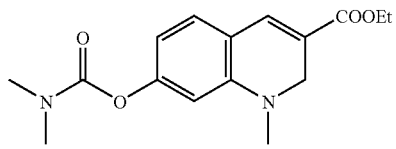

To a solution of ethyl N-methyl-7-(N,N-dimethylcarbamate)quinolinium-3-carboxylate triflate (100 mg, 0.22 mmol) prepared in stage D of example 1 in EtOH (10 mL) was added NaBH$_4$ (38 mg, 1 mmol). The resultant mixture was stirred for 3 hours at room temperature. After addition of water (2 mL) and evaporation of EtOH, the resulting aqueous phase was extracted twice with CH$_2$Cl$_2$ (2×10 mL). After drying (MgSO$_4$) and evaporation, flash chromatography on silica gel afforded the title compound in 20-60% yield.

EXAMPLE 62

Preparation of ethyl 1-methyl-5-(N,N-dimethylthiocarbamate)-1,2-dihydro-5-S-quinoline-3-carboxylate

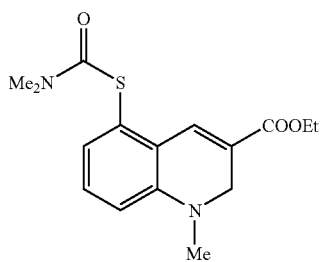

The title compound is prepared as reported in stage A of example 61 from a solution of ethyl 1-methyl-5-(N,N-dimethylthiocarbamate)-5-O-quinolinium-3-carboxylate triflate prepared in stage B of example 5.

EXAMPLE 63

Preparation of 1-methyl-5-(N,N-dimethylcarbamate)-3-(4,5-dihydro-4,4-dimethyl-2-oxazolyl)-1,2-dihydroquinoline

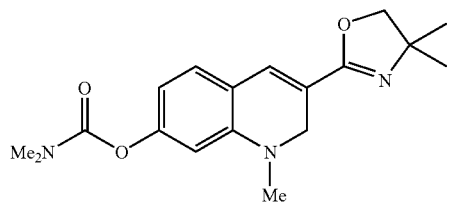

The title compound is prepared as reported in stage A of example 61 from 1-methyl-5-(N,N-dimethylcarbamate)-3-(4,5-dihydro-4,4-dimethyl-2-oxazolyl)quinolinium triflate prepared in stage D of example 8.

EXAMPLE 64

Preparation of ethyl 1-methyl-5-(N,N-dimethylcarbamate)-1,2-dihydropyridine-3-carboxylate

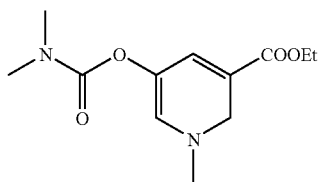

The title compound is prepared as reported in stage A of example 61 from ethyl 1-methyl-5-(N,N-dimethylcarbamate)pyridinium-3-carboxylate triflate prepared in stage C of example 27.

EXAMPLE 65

Preparation of ethyl-1-methyl-5-(N,N-dimethylthiocarbamate)-1,2-dihydro-5-S-pyridine-3-carboxylate

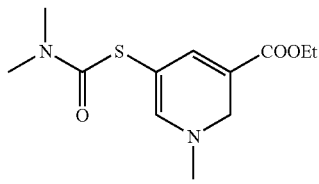

The title compound is prepared as reported in stage A of example 61 from ethyl 1-methyl 5-(N,N-dimethylthiocarbamate)-5-O-pyridinium-3-carboxylate prepared in stage B of example 29.

EXAMPLE 66

Preparation of 1-methyl-3-(N,N-diethylcarboxamido)-5-(N,N-dimethylcarbamate)-1,2-dihydropyridine

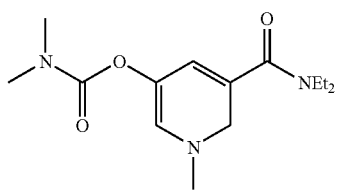

The title compound is prepared as reported in stage A of example 61 from 1-methyl-3-(N,N-diethylcarboxamido)-5-(N,N-dimethylcarbamate)pyridinium triflate prepared in stage B of example 31.

EXAMPLE 67

Preparation of methyl 5-(N,N-dimethylcarbamate)-1-methyl-1,4-dihydroquinoline-3-carboxylate

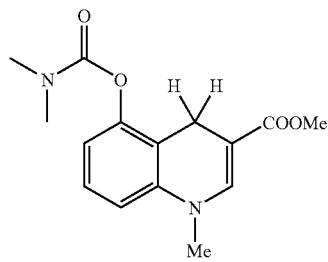

Stage A: methyl 5-methoxyquinoline-3-carboxylate.

To a solution of tert-butyl N-(2-formyl-3-methoxyphenyl) carbamate (7.8 g, 31 mmol) [described in *Adv. Synth. Catal.* 2003, 345, 743-765] and methyl trans-3-methoxyacrylate (7.4 mL, 68.4 mmol) dissolved in 150 ml of methanol, was added slowly 100 mL of an aqueous solution of hydrochloric acid 3M. The resulting mixture was stirred under reflux for 3 hours. The reaction mixture was then cooled to room temperature and neutralised by adding $Na_2CO_3$. The aqueous solution was extracted with $CH_2Cl_2$ (4×150 mL). The combined organic layers were dried over $MgSO_4$, filtered and evaporated under vacuum. The crude product was then filtered on silica gel (AcOEt:cyclohexane/1:1) to afford 5.6 g of compound of molecular formula $C_{12}H_{11}NO_3$. Aspect: yellow powder.

Melting point: 102° C.

NMR Spectrum of the Proton

In $CDCl_3$ at 300 MHz, chemical shifts (ppm) and multiplicity: 9.38 (s, 1H), 9.18 (s, 1H), 7.68 (m, 2H), 6.85 (m, 1H), 3.99 (s, 3H), 3.98 (s, 3H).

NMR Spectrum of the Carbon

In $CDCl_3$ at 75 MHz, chemical shifts (ppm) and nature of the carbon: 166.1 (C), 156.1 (C), 150.6 (C), 150.5 (CH), 133.9 (CH), 132.3 (CH), 122.0 (C), 121.4 (CH), 119.5 (C), 105.1 (CH), 55.9 ($CH_3$), 52.5 ($CH_3$).

Infrared Spectrum

IR spectrum was obtained as potassium bromide pellets. Absorption bands are given in $cm^{-1}$: 1728 (C=O), 1281, 1110, 815.

Stage B: 5-Hydroxyquinoline-3-carboxylic acid.

7.3 g (33.6 mmol) of compound prepared in stage A dissolved in 150 mL of an aqueous solution of HBr (48Wt %) was heated under reflux for 24 hours. After cooling the reaction mixture to room temperature, the pH was adjusted to 2.0 with an aqueous solution of NaOH 2M. After filtration of the insoluble matter, the pH was adjusted between 5 and 6, and the precipitate was filtered off and dried at 70° C. 3.5 g (yield: 55%) of product of molecular formula $C_{10}H_7NO_3$ was obtained. Aspect: brown solid.

Melting point: >260° C.

NMR Spectrum of the Proton

In DMSO-$d_6$ at 300 MHz, chemical shifts (ppm) and multiplicity: 10.91 (s, 1H), 9.25 (s, 1H), 9.04 (s, 1H), 7.70 (dd, J=7.9 Hz and 8.3 Hz, 1H), 7.53 (d, J=8.5 Hz, 1H), 7.02 (d, J=7.5 Hz, 1H).

NMR Spectrum of the Carbon

In DMSO-$d_6$ at 75 MHz, chemical shifts (ppm) and nature of the carbon: 166.7 (C), 154.8 (C), 150.3 (C), 150.1 (CH), 133.5 (CH), 133.1 (CH), 122.4 (C), 119.3 (CH), 118.5 (C), 109.8 (CH).

Elemental Analyse

Anal. calcd for $C_{10}H_7NO_3$: C, 63.49; H, 3.73; N, 7.40. Found: C, 62.96; H, 3.85; N, 7.38%.

Stage C: Methyl 5-hydroxyquinoline-3-carboxylate.

To a suspension of 3.5 g of compound prepared in stage B in methanol (250 mL) was added 1.5 mL of concentrated $H_2SO_4$. The reaction mixture was heated under reflux for 24 hours and then evaporated to half a volume before adding 100 mL of water. After neutralization with an aqueous solution of NaOH 2M, the mixture was extracted with ethyl acetate (4×200 mL). The combined organic layers were washed with brine (100 mL), dried over $MgSO_4$, filtered and evaporated under vacuum. The solid obtained was then filtered on silica gel ($CH_2Cl_2$:ethyl acetate/1:1) to afford 1.2 g (yield: 33%) of compound of molecular formula $C_{11}H_9NO_3$.

Aspect: yellow powder.

Melting point: 200° C. (degrad.)

NMR Spectrum of the Proton

In DMSO-$d_6$ at 300 MHz, chemical shifts (ppm) and multiplicity: 11.04 (s, 1H), 9.24 (s, 1H), 9.05 (s, 1H), 7.71 (dd, J=8.1 and 8.1 Hz. 1H), 7.53 (d, J=8.3 Hz, 1H), 7.02 (d, J=7.7 Hz, 1H), 9.94 (s, 3H).

NMR Spectrum of the Carbon

In DMSO-$d_6$ at 75 MHz, chermical shifts (ppm) and nature of the carbon: 165.3 (C), 154.6 (C), 150.2 (C), 149.3 (CH), 133.1 (CH), 133.0 (CH), 121.0 (C), 119.1 (CH), 118.1 (C), 109.6 (C), 52.4 ($CH_3$).

Infrared Spectrum

IR spectrum was obtained as potassium bromide pellets. Absorption bands are given in $cm^{-1}$: 1721 (C=O), 1277, 1115.

Stage D: Methyl 5-(N,N-dimethylcarbamate)-quinoline-3-carboxylate.

To 0.7 g (3.45 mmol) of compound prepared in stage C dissolved in dry tetrahydrofuran (30 mL) was added 0.33 g (6.90 mmol) of NaH (50% dispersion in mineral oil). The reaction mixture was stirred for 1 hour and then 635 µL (6.90 mmol) of N, N-dimethylcarbamoyl chloride was introduced before heating under reflux overnight. After cooling to room temperature, 15 mL of water was added and the THF was evaporated under reduced pressure. The aqueous layer was extracted with dichloromethane (3×20 mL). The combined organic layers were dried over $MgSO_4$, filtered and evaporated under vacuum. A purification by column chromatography on silica gel with cyclohexane/ethyl acetate (1/1) as eluent gave 757 mg (yield: 85%) of compound of molecular formula $C_{14}H_{14}N_2O_4$. Aspect: pale yellow powder.

Melting point: 112° C.

NMR Spectrum of the Proton

In $CDCl_3$ at 300 MHz, chemical shifts (ppm) and multiplicity: 9.45 (d, J=2 Hz, 1H), 8.95 (d, J=2 Hz, 1H), 8.03 (d, J=8.5 Hz, 1H), 7.82 (dd, J=7.9 and 8.5 Hz, 1H), 7.42 (d, J=7.5 Hz, 1H), 4.03 (s, 3H), 3.29 (s, 3H), 3.10 (s, 3H).

NMR Spectrum of the Carbon

In $CDCl_3$ at 75 MHz, chemical shifts (ppm) and nature of the carbon: 165.8 (C), 154.3 (C), 150.3 (C), 150.3 (CH), 147.8 (C), 133.2 (CH), 131.5 (CH), 126.7 (CH), 123.1 (C), 121.7 (C), 119.6 (C), 52.7 ($CH_3$), 37.1 ($CH_3$), 36.8 ($CH_3$).

Infrared Spectrum

IR spectrum was obtained as potassium bromide pellets. Absorption bands are given in $cm^{-1}$: 1759, 1729, 1286, 1176, 1160.

Stage E: Methyl 5-(N,N-dimethylcarbamate)-1-methylquinolinium-3-carboxylate triflate.

To 565 mg (2.06 mmol) of compound prepared in stage D dissolved in 50 mL of anhydrous dichloromethane was added, under $N_2$, 256 µL (227 mmol) of methyl trifluoromethanesulfonate. The reaction mixture was stirred for 3 hours at room temperature. Evaporation of the solvent gave 903 mg (yield: 100%) of compound of molecular formula $C_{16}H_{17}F_3N_2O_7S$. Aspect: pale yellow powder.

Melting point: 170° C.

NMR Spectrum of the Proton

In $CDCl_3$ at 300 MHz, chemical shifts (ppm) and multiplicity: 9.82 (s, 1H), 9.52 (s, 1H), 8.28 (m, 2H), 7.82 (dd, J=6.9 and 1.6 Hz, 1H), 4.73 (s, $CH_3$), 4.05 (s, $CH_3$), 3.27 (s, $CH_3$), 3.06 (s, $CH_3$).

NMR Spectrum of the Carbon

In $CDCl_3$ at 75 MHz, chemical shifts (ppm) and nature of the carbon: 162.1 (C), 153.0 (C), 150.9 (CH), 149.6 (C), 142.4 (CH), 140.1 (C), 138.6 (CH), 124.2 (C), 123.9 (C), 123.3 (CH), 116.0 (CH), 54.0 ($CH_3$), 47.2 ($CH_3$), 37.3 ($CH_3$), 37.0 ($CH_3$).

NMR Spectrum of the Fluor

In $CDCl_3$ at 282.5 MHz, chemical shifts (ppm): −79.0.

Elemental Analyse

Anal. calcd for $C_{16}H_{17}F_3N_2O_7S$: C, 43.84; H, 3.91; N, 6.39; S, 7.31. Found: C, 43.25; H, 3.86; N, 6.52; S, 7.21%.

Infrared Spectrum

IR spectrum was obtained as potassium bromide pellets. Absorption bands are given in $cm^{-1}$: 1736 (C=O), 1268, 1159, 1029.

Stage F: Methyl 5-(N,N-dimethylcarbamate)-1-methyl-1,4-dihydroquinoline-3-carboxylate.

0.1 g (0.23 mmol) of compound prepared in stage E and 54 mg (0.25 mmol) of N-benzyl-1,4-dihydronicotinamide (BNAH) were stirred at room temperature in 10 mL of dichloromethane for 1 hour. The reaction mixture was then washed with water (3×10 mL). The organic layer was separated, dried over $MgSO_4$, filtered and evaporated under reduced pressure at room temperature. 45 mg (yield: 67%) of compound of molecular formula $C_{15}H_{18}N_2O_4$ was obtained. Aspect: pale yellow powder.

Melting point: 130° C. (degrad.)

NMR Spectrum of the Proton

In $CDCl_3$ at 300 MHz, chemical shifts (ppm) and multiplicity: 7.18 (s, 1H), 7.11 (dd, J=8.1 and 8.3 Hz, 1H), 6.73 (d, J=8.1 Hz, 1H), 6.55 (d, J=8.1 Hz, 1H), 3.71 (s, 3H), 3.61 (s, 2H), 3.17 (s, 3H), 3.10 (s, 3H), 2.99 (s, 3H).

NMR Spectrum of the Carbon

In $CDCl_3$ at 75 MHz, chemical shifts (ppm) and nature of the carbon: 168.3 (C), 154.4 (C), 150.3 (C), 142.9 (CH), 140.1 (C), 127.4 (CH), 117.2 (CH), 116.8 (C), 109.7 (CH), 96.8 (CH), 51.2 ($CH_3$), 39.5 ($CH_3$), 36.9 ($CH_3$), 36.6 ($CH_3$), 21.3 ($CH_2$).

Infrared Spectrum

IR spectrum was obtained as potassium bromide pellets. Absorption bands are given in $cm^{-1}$: 1725, 1679, 1390, 1270, 1168, 1146.

EXAMPLE 68

Preparation of 5-(N,N-dimethylcarbamate)-1-methyl-3-(N-methylcarboxamido)-1,4-dihydroquinoline

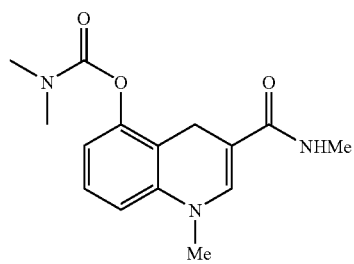

Stage A: 5-(benzyloxy)-3-(N-methylcarboxamido)quinoline.

To 1 g (3.6 mmol) of compound prepared in stage A of example 2 in suspension in 50 mL of dry dichloromethane was added 3 drops of dry DMF. The solution was stirred under $N_2$ at 0° C. and then 2.2 mL (25.2 mmol) of oxalyl chloride was added. The reaction mixture was stirred for 1 hour at room temperature and then evaporated under reduced pressure. The residue was dissolved in dry $CH_2Cl_2$ (30 mL) and the solution was added to 9 mL (18 mmol) of methylamine (2M in THF) diluted in 50 mL of dry dichloromethane at 0° C. The reaction mixture was then heated under reflux overnight. The reaction mixture was cooled to room temperature and 50 mL of water was added. The aqueous layer was extracted with dichloromethane (3×50 mL). The combined organic layers were dried over $MgSO_4$ and filtered. After evaporation of the solvent, a purification by column chromatography on silica gel with ethyl acetate as eluent gave 393 mg (yield: 37%) of compound of molecular formula $C_{18}H_{16}N_2O_2$. Aspect: orange powder.

Melting point: 60° C. (degrad.).

NMR Spectrum of the Proton

In $CDCl_3$ at 300 MHz, chemical shifts (ppm) and multiplicity: 9.22 (d, J=2.1 Hz, 1H), 8.90 (d, J=2.1 Hz, 1H), 7.58 (m, 2H), 7.36 (m, 5H), 7.16 (br, 1H), 6.85 (d, J=7.2 Hz, 1H), 5.13 (s, 2H), 2.97 (d, J=4.7 Hz, 3H).

NMR Spectrum of the Carbon

In $CDCl_3$ at 75 MHz, chemical shifts (ppm) and nature of the carbon: 166.7 (C), 154.7 (C), 149.8 (C), 149.0 (CH), 136.1 (C), 131.3 (CH), 130.1 (CH), 128.7 (CH), 128.3 (CH), 127.6 (CH), 126.3 (C), 121.3 (CH), 119.5 (C), 106.3 (CH), 70.6 ($CH_2$), 26.9 ($CH_3$).

Infrared Spectrum

IR spectrum was obtained as potassium bromide pellets. Absorption bands are given in $cm^{-1}$: 1640 (C=O), 1265, 1091, 813.

Stage B: 5-hydroxy-3-(N-methylcarboxamido)quinoline.

391 mg (1.34 mmol) of compound prepared in stage A dissolved in 50 mL of ethanol was stirred in presence of $Pd/C_5$% (276 mg, 0.13 mmol) under an atmosphere of hydrogen for 3 hours. The palladium was then removed by filtration and ethanol was evaporated under reduced pressure. The $^1H$ NMR of the crude product showed a part of a reduced by-product at the pyridine ring (dihydroquinoline derivatives). The mixture was dissolved in ethanol and treated with air gas until complete re-oxydation of the product. Evaporation of the solvent gave 270 mg (yield: 99%) of compound of molecular formula $C_{11}H_{10}N_2O_2$. Aspect: brown powder.

Melting point: 200° C. (degrad.).

NMR Spectrum of the Proton

In CDCl₃ at 300 MHz, chemical shifts (ppm) and multiplicity: 10.82 (s, 1H), 9.22 (d, J=2.3 Hz, 1H), 8.97 (d, J=2.1 Hz, 1H), 8.83 (br, 1H), 7.64 (dd, J=8.3 and 7.9 Hz, 1H), 7.50 (d, J=8.3, 1H), 6.99 (d, J=7.5 Hz, 1H), 2.84 (d, J=4.5 Hz, 3H).

Infrared Spectrum

IR spectrum was obtained as potassium bromide pellets. Absorption bands are given in cm⁻¹: 1622, 1320, 1279, 812.

Stage C: 5-(N,N-dimethylcarbamate)-3-(N-methylcarboxamido)quinoline.

To a solution of 150 mg (0.74 mmol) of compound prepared in stage B in 50 mL of acetone was added finely powdered $K_2CO_3$ (511 mg, 3.71 mmol) and 82 µL (0.89 mmol) of N,N-dimethylcarbamoyl chloride. This mixture was heated under reflux overnight and then filtered. After evaporation of the solvent, a purification by column chromatography on silica gel with dichloromethane then dichloromethane/iPrOH (9/1) as eluent gave 132 mg (yield: 65%) of compound of molecular formula $C_{14}H_{15}N_3O_3$. Aspect: pale yellow powder.

NMR Spectrum of the Proton

In CDCl₃ at 300 MHz, chemical shifts (ppm) and multiplicity: 9.18 (d, J=2.3 Hz, 1H), 8.71 (d, J=1.5 Hz, 1H), 8.00 (d, J=8.5 Hz, 1H), 7.78 (dd, J=7.7 and 8.5 Hz, 1H), 7.40 (d, J=7.7 Hz, 1H), 3.27 (s, 3H), 3.07 (m, 6H).

NMR Spectrum of the Carbon

In CDCl₃ at 75 MHz, chemical shifts (ppm) and nature of the carbon: 166.5 (C), 154.9 (C), 149.8 (C), 148.6 (CH), 147.9 (C), 130.9 (CH), 130.6 (CH), 127.7 (C), 126.9 (CH), 122.1 (C), 120.0 (CH), 37.4 (CH₃), 37.1 (CH₃), 27.3 (CH₃).

Stage D: 5-(N,N-dimethylcarbamate)-1-methyl-3-(N-methylcarboxamido)quinolinium triflate To 146 mg (0.53 mmol) of compound prepared in stage C dissolved in 10 mL of anhydrous dichloromethane was added, under N₂, 68 µL (0.60 mmol) of methyl trifluoromethanesulfonate. The reaction mixture was stirred overnight at room temperature. Evaporation of the solvent gave 216 mg (yield: 100%) of compound of molecular formula $C_{16}H_{18}F_3N_3O_6S$. Aspect: pale brown powder.

NMR Spectrum of the Proton

In CDCl₃ at 300 MHz, chemical shifts (ppm) and multiplicity: 9.86 (s, 1H), 9.69 (s, 1H), 8.58 (br, 1H), 8.25 (dd, J=8.9 and 7.9 Hz, 1H), 8.13 (d, J=9.0 Hz, 1H), 7.85 (d, J=7.7 Hz, 1H), 4.75 (s, 3H), 3.30 (s, 3H), 3.09 (s, 3H), 3.05 (d, J=4.5 Hz, 1H).

Stage E: 5-(N,N-dimethylcarbamate)-1-methyl-3-(N-methylcarboxamido)-1,4-dihydroquinoline.

70 mg (0.17 mmol) of compound prepared in stage D was dissolved in 3 mL of degassed CH₂Cl₂ (N₂) and 3 mL of degassed water (N₂) and under an atmosphere of nitrogen. 147 mg (0.85 mmol) of sodium dithionite dissolved in 1 mL of degassed water (N₂) and 54 mg (0.51 mmol) of $Na_2CO_3$ dissolved in 1 mL of degassed water (N₂) were introduced simultaneously. The reaction mixture was stirred for 1 hour and the same quantity of sodium dithionite and $Na_2CO_3$ were introduced in the same way. After stirring 1 hour the reaction mixture, 294 mg (1.70 mmol) of sodium dithionite dissolved in 2 mL of degassed water (N₂) and 108 mg (1.02 mmol) of $Na_2CO_3$ dissolved in 2 mL of degassed water (N₂) were introduced simultaneously. Stirring was pursued for 1 supplementary hour. The aqueous layer was separated and extracted with dichloromethane (2×5 mL) giving after evaporation of the solvent some impure product. The pH of the aqueous layer was adjusted to 5.0 with an aqueous solution of HCl 1M. Extraction with dichloromethane (3×5 mL), drying over MgSO₄, filtration an evaporation of the solvent under reduced pressure at room temperature gave 26 mg (yield: 53%) of compound of molecular formula $C_{15}H_{19}N_3O_3$. Aspect: pale brown powder.

NMR Spectrum of the Proton

In CDCl₃ at 300 MHz, chemical shifts (ppm) and multiplicity: 7.12 (m, 2H), 6.67 (d, J=8.1 Hz, 1H), 6.54 (d, J=8.3 Hz, 1H), 5.36 (br, 1H), 3.61 (s, 2H), 3.17 (s, 3H), 3.12 (s, 3H), 3.02 (s, 3H), 2.88 (d, J=4.9 Hz, 3H).

NMR Spectrum of the Carbon

In CDCl₃ at 75 MHz, chemical shifts (ppm) and nature of the carbon: 168.6 (C), 154.8 (C), 150.5 (C), 140.9 (C), 139.8 (CH), 128.0 (CH), 116.3 (CH), 115.7 (C), 109.8 (CH), 99.3 (CH), 53.9 (CH₂), 39.5 (CH₃), 37.2 (CH₃), 37.0 (CH₃), 26.9 (CH₃).

EXAMPLE 69

Preparation of 5-(N,N-dimethylcarbamate)-3-(N,N-dimethylcarboxamido)-1-methyl-1,4-dihydroquinoline

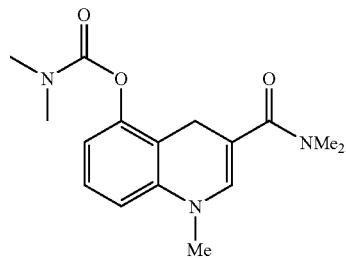

Stage A: 5-(benzyloxy)-3-(N,N-dimethylcarboxamido)quinoline.

0.5 g (1.79 mmol) of compound prepared in stage A of example 2 was heated under reflux in 15 mL of thionyl chloride for 1 hour. After evaporation of thionyl chloride, the residue was dissolved in 15 mL of dry dichloromethane under an atmosphere of N₂. Then 4.5 mL (8.96 mmol) of dimethylamine (2M in THF) was added at 0° C. The reaction mixture was then heated under reflux overnight and evaporated. A purification by column chromatography on silica gel with dichloromethane then dichloromethane/iPrOH (9/1) as eluent gave 275 mg (yield: 50%) of compound of molecular formula $C_{19}H_{18}N_2O_2$. Aspect: pale yellow powder.

NMR Spectrum of the Proton

In CDCl₃ at 300 MHz, chemical shifts (ppm) and multiplicity: 8.95 (s, 1H), 8.72 (s, 1H), 7.67 (m, 2H), 7.42 (m, 5H), 6.97 (d, J=7.5 Hz, 1H), 5.23 (s, 2H), 3.16 (s, 3H), 3.04 (s, 3H).

Stage B: 5-hydroxy-3-(N-methylcarboxamido)quinoline.

275 mg (0.90 mmol) of compound prepared in stage A dissolved in 40 mL of ethanol was stirred in presence of Pd/C 5% (191 mg, 0.09 mmol) under an atmosphere of hydrogen for 3 hours. The palladium was then removed by filtration and ethanol was evaporated under reduced pressure. The ¹H NMR of the crude product showed a part of a reduced by-product at the pyridine ring (dihydroquinoline derivatives). The mixture was dissolved in ethanol and treated with air gas until complete re-oxydation of the product. Evaporation of the solvent and a purification by column chromatography on silica gel with ethyl acetate as eluent gave 144 mg (yield: 74%) of compound of molecular formula $C_{12}H_{12}N_2O_2$. Aspect: brown powder.

NMR Spectrum of the Proton

In DMSO-$d_6$ at 300 MHz, chemical shifts (ppm) and multiplicity: 10.88 (s, 1H), 8.98 (d, J=2.0 Hz, 1H), 8.63 (d, J=2.0 Hz, 1H), 7.72 (dd, J=8.1 and 7.9 Hz, 1H), 7.57 (d, J=8.3 Hz, 1H), 7.08 (d, J=7.7 Hz, 1H), 3.10 (m, 6H).

NMR Spectrum of the Carbon

In DMSO-$d_6$ at 75 MHz, chemical shifts (ppm) and nature of the carbon: 168.2 (C), 154.3 (C), 148.7 (CH), 148.0 (C), 132.0 (CH), 130.5 (CH), 128.2 (C), 118.7 (CH), 118.6 (C), 109.8 (CH), 36.0 ($CH_3$), 39.6 ($CH_3$).

Stage C: 5-(N,N-dimethylcarbamate)-3-(N,N-dimethylcarboxamido)quinoline.

To 0.1 g (0.46 mmol) of compound prepared in stage B dissolved in dry tetrahydrofuran (5 mL) was added 33 mg (0.69 mmol) of NaH (50% dispersion in mineral oil). The reaction mixture was stirred for 1 hour and then 64 μL (0.69 mmol) of N, N-dimethylcarbamoyl chloride was introduced before heating under reflux overnight. After cooling to room temperature, 5 mL of water was added and the THF was evaporated under reduced pressure. The aqueous layer was extracted with dichloromethane (3×5 mL). The combined organic layers were dried over $MgSO_4$, filtered and evaporated under vacuum. Purification by column chromatography on neutral alumina gel with dichloromethane/ethyl acetate (1/1) as eluent gave 72 mg (yield: 55%) of compound of molecular formula $C_{15}H_{17}N_3O_3$. Aspect: pale brown powder.

NMR Spectrum of the Proton

In $CDCl_3$ at 300 MHz, chemical shifts (ppm) and multiplicity: 8.95 (d, J=1.9 Hz, 1H), 8.38 (d, J=1.7 Hz, 1H), 8.99 (d, J=8.5 Hz, 1H), 7.75 (dd, J=7.9 and 8.3 Hz, 1H), 7.39 (d, J=7.7 Hz, 1H), 3.24 (s, 3H), 3.18 (s, 3H), 3.06 (s, 6H).

NMR Spectrum of the Carbon

In $CDCl_3$ at 75 MHz, chemical shifts (ppm) and nature of the carbon: 169.1 (C), 154.4 (C), 148.9 (CH), 148.6 (C), 147.3 (CH), 130.3 (CH), 130.0 (CH), 129.3 (C), 126.8 (CH), 122.0 (C), 119.6 (CH), 39.9 ($CH_3$), 37.1 ($CH_3$), 36.8 ($CH_3$), 35.7 ($CH_3$).

Stage D: 5-(N,N-dimethylcarbamate)-3-(N,N-dimethylcarboxamido)-1-methylquinolinium triflate To 25 mg (0:09 mmol) of compound prepared in stage C dissolved in 5 mL of anhydrous dichloromethane was added, under $N_2$, 12 μL (0.11 mmol) of methyl trifluoromethanesulfonate. The reaction mixture was stirred overnight at room temperature. Evaporation of the solvent gave 40 mg (yield: 100%) of compound of molecular formula $C_{17}H_{20}F_3N_3O_6S$. Aspect: brown powder.

NMR Spectrum of the Proton

In $CDCl_3$ at 300 MHz, chemical shifts (ppm) and multiplicity: 9.44 (s, 1H), 9.07 (s, 1H), 8.19 (m, 2H), 7.77 (m, 1H), 4.69 (s, 3H), 3.25 (s, 3H), 3.13 (s, 6H), 3.05 (s, 3H).

NMR Spectrum of the Carbon

In $CDCl_3$ at 75 MHz, chemical shifts (ppm) and nature of the carbon: 152.7 (C), 149.2 (CH), 148.6 (CH), 139.3 (CH), 138.6 (C), 136.7 (CH), 129.7 (C), 123.7 (C), 122.6 (C), 115.1 (CH), 46.3 ($CH_3$), 39.5 ($CH_3$), 36.9 ($CH_3$), 36.6 ($CH_3$), 35.6 ($CH_3$).

EXAMPLE 70

Preparation of morpholine 4-[5-(N,N-dimethylcarbamate)-1-methyl-1,4-dihydroquinolyl-3-carbonyl]

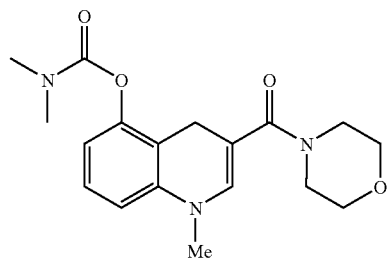

Stage A: morpholine 4-[5-(benzyloxy)quinolyl-3-carbonyl].

To 0.5 g (1.79 mmol) of compound prepared in stage A of example 2 in suspension in 20 mL of dry dichloromethane was added 3 drops of dry DMF. The solution was stirred under $N_2$ at 0° C. and then 159 μL (1.80 mmol) of oxalyl chloride was added. The reaction mixture was stirred for 1 hour at room temperature and then evaporated under reduced pressure. The residue was dissolved in dry $CH_2Cl_2$ (15 mL) and a solution of 157 μL (1.80 mmol) of morpholine with 0.5 mL of triethylamine (3.60 mmol) dissolved in 5 mL of dry dichloromethane was added at 0° C. The reaction mixture was then heated under reflux overnight. The reaction mixture was cooled to room temperature and 20 mL of water was added. The aqueous layer was extracted with dichloromethane (3×20 mL). The combined organic layers were dried over $MgSO_4$ and filtered. After evaporation of the solvent, a purification by column chromatography on silica gel with dichloromethane/acetone (7/3) with 1% of triethylamine as eluent gave 278 mg (yield: 45%) of compound of molecular formula $C_{21}H_{20}N_2O_3$. Aspect: orange powder.

Melting point: 60° C. (degrad.)

NMR Spectrum of the Proton

In $CDCl_3$ at 300 MHz, chemical shifts (ppm) and multiplicity: 8.93 (d, J=2.3 Hz, 1H), 8.71 (d, J=2.1 Hz, 1H), 7.69 (m, 2H), 7.38 (m, 5H), 6.98 (d, J=6.4 Hz, 1H), 5.24 (s, 2H), 3.70 (m, 8 H).

NMR Spectrum of the Carbon

In $CDCl_3$ at 75 MHz, chemical shifts (ppm) and nature of the carbon: 168.6 (C), 154.9 (C), 149.6 (C), 149.1 (CH), 136.5 (C), 131.4 (CH), 130.9 (CH), 129.2 (CH), 128.7 (CH), 128.0 (CH), 127.7 (C), 122.0 (C), 120.2 (C), 106.8 (CH), 71.0 ($CH_2$), 67.2 ($CH_2$).

Infrared Spectrum

IR spectrum was obtained as potassium bromide pellets. Absorption bands are given in $cm^{-1}$: 1635 (C=O), 1266, 1114.

Stage B: morpholine 4-[5-hydroxyquinolyl-3-carbonyl].

278 mg (0.80 mmol) of compound prepared in stage A dissolved in 40 mL of ethanol was stirred in presence of Pd/$C_5$% (170 mg, 0.08 mmol) under an atmosphere of hydrogen for 3 hours. The palladium was then removed by filtration and ethanol was evaporated under reduced pressure. The $^1H$ NMR of the crude product showed a part of a reduced byproduct at the pyridine ring (dihydroquinoline derivatives). The mixture was dissolved in ethanol and treated with air gas until complete re-oxydation of the product. Evaporation of the solvent and a purification by column chromatography on silica gel with dichloromethane/iPrOH (95/5) and 1% of triethylamine as eluent gave 122 mg (yield: 60%) of compound of molecular formula $C_{14}H_{14}N_2O_3$. Aspect: brown powder.

NMR Spectrum of the Proton

In $CDCl_3$ at 300 MHz, chemical shifts (ppm) and multiplicity: 8.91 (d, J=2.1 Hz, 1H), 8.76 (d, J=1.9 Hz, 1H), 7.57 (d, J=8.5 Hz, 1H), 7.48 (dd, J=7.9 and 8.3 Hz, 1H), 6.90 (d, J=7.5 Hz, 1H), 3.73 (m, 8H).

NMR Spectrum of the Carbon

In $CDCl_3$ at 75 MHz, chemical shifts (ppm) and nature of the carbon: 168.7 (C), 154.0 (C), 148.6 (C), 148.0 (CH), 132.1 (CH), 131.9 (CH), 126.2 (C), 119.3 (C), 119.2 (CH), 110.3 (CH), 66.9 ($CH_2$).

Stage C: morpholine 4-[5-(N,N-dimethylcarbamate) quinolyl-3-carbonyl].

To 444 mg (1.72 mmol) of compound prepared in stage B dissolved in dry tetrahydrofuran (20 mL) was added 166 mg (3.45 mmol) of NaH (50% dispersion in mineral oil). The reaction mixture was stirred for 1 hour and then 320 μL (3.45 mmol) of N, N-dimethylcarbamoyl chloride was introduced before heating under reflux overnight. After cooling at room temperature, 15 mL of water was added and the THF was evaporated under reduced pressure. The aqueous layer was extracted with dichloromethane (3×20 mL). The combined organic layers were dried over $MgSO_4$, filtered and evaporated under vacuum. Purification by column chromatography on silica gel with dichloromethane then dichloromethane/iPrOH (98/2) as eluent gave 102 mg (yield: 18%) of compound of molecular formula $C_{17}H_{19}N_3O_4$. Aspect: pale yellow powder.

Melting point: 130° C.

NMR Spectrum of the Proton

In $CDCl_3$ at 300 MHz, chemical shifts (ppm) and multiplicity: 8.91 (d, J=2.3 Hz, 1H), 8.35 (d, J=2.1 Hz, 1H), 7.98 (d, J=8.5 Hz, 1H), 7.74 (dd, J=8.5 and 7.9 Hz, 1H), 7.38 (d, J=7.5 Hz, 1H), 3.66 (m, 8H), 3.23 (s, 3H), 3.04 (s, 3H).

NMR Spectrum of the Carbon

In $CDCl_3$ at 75 MHz, chemical shifts (ppm) and nature of the carbon: 168.3 (C), 154.7 (C), 149.3 (C), 148.8 (CH), 147.5 (C), 130.8 (CH), 130.7 (CH), 128.4 (C), 127.1 (CH), 122.2 (C), 120.1 (CH), 67.2 ($CH_2$), 37.4 ($CH_3$), 37.1 ($CH_3$).

Elemental Analyse

Anal. calcd for $C_{17}H_{19}N_3O_4$: C, 62.00; H, 5.81; N, 12.76. Found: C, 62.25; H, 5.89; N, 12.02%.

Infrared Spectrum

IR spectrum was obtained as potassium bromide pellets. Absorption bands are given in $cm^{-1}$: 1725, 1628, 1168, 1111.

Stage D: 5-(N,N-dimethylcarbamate)-1-methyl-3-(morpholinocarboxy)quinolinium triflate To 102 mg (0.31 mmol) of compound prepared in stage C dissolved in 10 mL of anhydrous dichloromethane was added, under $N_2$, 35 μL (0.31 mmol) of methyl trifluoromethanesulfonate. The reaction mixture was stirred overnight at room temperature. Evaporation of the solvent gave 152 mg (yield: 100%) of compound of molecular formula $C_{19}H_{22}F_3N_3O_7S$. Aspect: brown powder.

Melting point: 92° C. (degrad.).

NMR Spectrum of the Proton

In $CDCl_3$ at 300 MHz, chemical shifts (ppm) and multiplicity: 9.37 (d, J=1.0 Hz, 1H), 8.98 (d, J=1.0 Hz, 1H), 8.16 (m, 2H), 7.76 (dd, J=6.6 and 2.1 Hz, 1H), 4.65 (s, 3H), 3.64 (m, 8H), 3.24 (s, 3H), 3.05 (s, 3H).

NMR Spectrum of the Carbon

In $CDCl_3$ at 75 MHz, chemical shifts (ppm) and nature of the carbon: 163.2 (C), 153.0 (C), 149.7 (CH), 149.0 (C), 139.6 (CH), 139.1 (C), 137.1 (CH), 129.3 (C), 124.0 (C), 122.9 (CH), 115.6 (CH), 66.5 ($CH_2$), 47.0 ($CH_3$), 37.3 ($CH_3$), 37.0 ($CH_3$).

NMR Spectrum of the Fluor

In $CDCl_3$ at 282.5 MHz, chemical shifts (ppm): −79.0.

Infrared Spectrum

IR spectrum was obtained as potassium bromide pellets. Absorption bands are given in $cm^{-1}$: 1731, 1638, 1260, 1155, 1031.

Stage E: morpholine 4-[5-(N,N-dimethylcarbamate)-1-methyl-1,4-dihydroquinolyl-3-carbonyl].

50 mg (0.11 mmol) of compound prepared in stage D was dissolved in 3 mL of degassed $CH_2Cl_2$ ($N_2$) and 3 mL of degassed water ($N_2$) and under an atmosphere of nitrogen. 84 mg (0.48 mmol) of sodium dithionite dissolved in 1 mL of degassed water ($N_2$) and 31 mg (0.29 mmol) of $Na_2CO_3$ dissolved in 1 mL of degassed water ($N_2$) were introduced simultaneously. The reaction mixture was vigorously stirred for 1 hour and the same quantity of sodium dithionite and $Na_2CO_3$ were introduced in the same way. After stirring 1 hour the reaction mixture, 164 mg (0.94 mmol) of sodium dithionite dissolved in 2 mL of degassed water ($N_2$) and 62 mg (0.58 mmol) of $Na_2CO_3$ dissolved in 2 mL of degassed water ($N_2$) were introduced simultaneously. Stirring was pursued for 1 supplementary hour. 100 μL of glacial acetic acid was added and the organic layer was separated. After extraction of the aqueous layer with dichloromethane (3×25 mL), the organic layers were combined, dried over $MgSO_4$, filtered and evaporated under reduced pressure at room temperature giving 16 mg (yield: 46%) of compound of molecular formula $C_{18}H_{23}N_3O_4$. Aspect: pale brown powder.

NMR Spectrum of the Proton

In $CDCl_3$ at 300 MHz, chemical shifts (ppm) and multiplicity: 7.12 (dd, J=8.3 and 8.1 Hz, 1H), 6.70 (d, J=8.1 Hz, 1H), 6.54 (d, J=8.3 Hz, 1H), 6.40 (s, 1H), 3.67 (m, 10H), 3.15 (s, 3H), 3.09 (s, 3H), 3.00 (s, 3H).

NMR Spectrum of the Carbon

In $CDCl_3$ at 75 MHz, chemical shifts (ppm) and nature of the carbon: 171.5 (C), 157.2 (C), 149.9 (C), 141.2 (C), 138.2 (CH), 127.4 (CH), 116.3 (CH), 115.5 (C), 109.1 (CH), 100.2 (C), 67.2 ($CH_2$), 46.1 ($CH_2$), 39.1 ($CH_3$), 36.9 ($CH_3$), 36.7 ($CH_3$).

EXAMPLE 71

Preparation of 5-(N,N-dimethylcarbamate)-2-methylisoquinolinium triflate

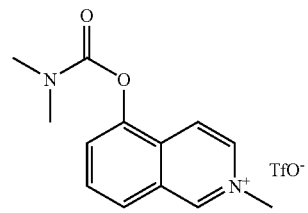

Stage A: 5-(N,N-dimethylcarbamate)isoquinoline.

To a solution of 300 mg (2.07 mmol) of 5-hydroxyisoquinoline in 50 mL of acetone was added finely powdered $K_2CO_3$ (1.43 g, 10.35 mmol) and 202 μL (2.2 mmol) of N,N-dimethylcarbamoyl chloride. This mixture was heated under reflux for 5 hours and then filtered. After evaporation of the solvent, a purification by column chromatography on silica gel with diethyl ether/ethyl acetate (1/1) as eluent gave 365 mg (yield: 82%) of compound of molecular formula $C_{12}H_{12}N_2O_2$. Aspect: white powder.

Melting point: 78° C.

NMR Spectrum of the Proton

In $CDCl_3$ at 300 MHz, chemical shifts (ppm) and multiplicity: 9.21 (s, 1H), 8.50 (d, J=5.8 Hz, 1H), 7.75 (d, J=7.7 Hz, 1H), 7.66 (d, J=5.8 Hz, 1H), 7.48 (m, 2H), 3.17 (s, 3H), 3.00 (s, 3H).

NMR Spectrum of the Carbon

In $CDCl_3$ at 75 MHz, chemical shifts (ppm) and nature of the carbon: 154.2 (C), 152.3 (CH), 146.2 (C), 143.2 (CH), 130.0 (C), 129.3 (C), 126.9 (CH), 124.7 (CH), 122.4 (CH), 114.2 (CH), 36.8 ($CH_3$), 36.5 ($CH_3$).

Elemental Analyse

Anal. calcd for $C_{12}H_{12}N_2O_2$: C, 66.65; H, 5.59; N, 12.96. Found: C, 66.47; H, 5.59; N, 12.95%

Infrared Spectrum

IR spectrum was obtained as potassium bromide pellets. Absorption bands are given in $cm^{-1}$: 1724, 1376, 1159, 812.

Stage B: 5-(N,N-dimethylcarbamate)-2-methylisoquinolinium triflate.

To 331 mg (1.53 mmol) of compound prepared in stage A dissolved in 5 mL of anhydrous dichloromethane was added, under $N_2$, 190 μL (1.68 mmol) of methyl trifluoromethanesulfonate. The reaction mixture was stirred overnight at room temperature. The precipitate was filtered and gave 534 mg (yield: 92%) of compound of molecular formula $C_{14}H_{15}F_3N_2O_5S$. Aspect: white powder.

Melting point: 170° C.

NMR Spectrum of the Proton

In DMSO-$d_6$ at 300 MHz, chemical shifts (ppm) and multiplicity: 10.06 (s, 1H), 8.69 (d, J=7.0 Hz, 1H), 8.49 (d, J=7.0 Hz, 1H), 8.36 (dd, J=6.8 and 2.5 Hz, 1H), 8.07 (m, 2H), 4.48 (s, 3H), 3.23 (s, 3H), 2.99 (s, 3H).

NMR Spectrum of the Carbon

In DMSO-$d_6$ at 75 MHz, chemical shifts (ppm) and nature of the carbon: 153.6 (C), 151.4 (CH), 146.6 (C), 136.6 (CH), 131.9 (CH), 131.2 (C), 129.3 (CH), 128.2 (C), 127.9 (CH), 120.4 (CH), 48.3 ($CH_3$), 37.0 ($CH_3$), 36.8 ($CH_3$).

NMR Spectrum of the Fluor

In DMSO-$d_6$ at 282.5 MHz, chemical shifts (ppm): −78.2.

Elemental Analyse

Anal. calcd for $C_{14}H_{15}F_3N_2O_5S$: C, 44.21; H, 3.98; N, 7.37; S, 8.43. Found: C, 44.05; H, 4.11; N, 7.47; S, 8.26%.

Infrared Spectrum

IR spectrum was obtained as potassium bromide pellets. Absorption bands are given in $cm^{-1}$: 1728 (C=O), 1265, 1162, 1031.

EXAMPLE 72

Preparation of 7-(N,N-Dimethylcarbamate)-2-Methylisoquinolinium Triflate

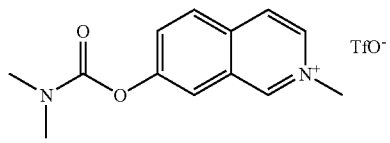

Stage A: 7-(N,N-dimethylcarbamate)isoquinoline.

To a solution of 111 mg (0.77 mmol) of 7-hydroxyisoquinoline in 20 mL of acetone was added finely powdered $K_2CO_3$ (0.528 g, 3.82 mmol) and 85 μL (0.92 mmol) of N,N-dimethylcarbamoyl chloride. This mixture was heated under reflux overnight and then filtered. After evaporation of the solvent, a purification by column chromatography on silica gel with dichloromethane/iPrOH (9/1) as eluent gave 150 mg (yield: 90%) of compound of molecular formula $C_{12}H_{12}N_2O_2$. Aspect: white powder.

Melting point: 104° C.

NMR Spectrum of the Proton

In $CDCl_3$ at 300 MHz, chemical shifts (ppm) and multiplicity: 9.21 (s, 1H), 8.50 (d, J=5.8 Hz, 1H), 7.83 (d, J=8.9 Hz, 1H), 7.72 (d, J=2.1 Hz, 1H), 7.64 (d, J=5.8 Hz, 1H), 7.50 (dd, J=8.9 and 2.3 Hz, 1H), 3.17 (s, 3H), 3.06 (s, 3H).

NMR Spectrum of the Carbon

In $CDCl_3$ at 75 MHz, chemical shifts (ppm) and nature of the carbon: 154.9 (C), 152.4 (CH), 150.3 (C), 133.8 (C), 129.4 (C), 128.2 (CH), 126.8 (CH), 120.6 (CH), 118.5 (CH), 37.2 ($CH_3$), 36.9 ($CH_3$).

Infrared Spectrum

IR spectrum was obtained as potassium bromide pellets. Absorption bands are given in $cm^{-1}$: 1722 (C=O), 1383, 1184.

Elemental Analyse

Anal. calcd for $C_{12}H_{12}N_2O_2$: C, 66.65; H, 5.59; N, 12.96. Found: C, 66.67; H, 6.28; N, 12.81%.

Stage B: 7-(N,N-dimethylcarbamate)-2-methylisoquinolinium triflate.

To 50 mg (0.23 mmol) of compound prepared in stage A dissolved in 5 mL of anhydrous dichloromethane was added, under $N_2$, 29 μL (0.26 mmol) of methyl trifluoromethanesulfonate. The reaction mixture was stirred overnight at room temperature. Evaporation of the solvent gave 87 mg (yield: 100%) of compound of molecular formula $C_{14}H_{15}F_3N_2O_5S$. Aspect: pale yellow powder.

Melting point: 150° C.

NMR Spectrum of the Proton

In DMSO-$d_6$ at 300 MHz, chemical shifts (ppm) and multiplicity: 9.90 (s, 1H), 8.68 (d, J=6.6 Hz, 1H), 8.57 (d, J=6.8 Hz, 1H), 8.37 (d, J=8.9 Hz, 1H), 8.25 (d, J=2.1 Hz, 1H), 8.08 (dd, J=8.9 and 2.3 Hz, 1H), 4.46 (s, 3H), 3.13 (s, 3H), 2.97 (s, 3H).

NMR Spectrum of the Carbon

In DMSO-$d_6$ at 75 MHz, chemical shifts (ppm) and nature of the carbon: 153.6 (C), 152.6 (C), 150.3 (CH), 136.0 (CH), 134.7 (C), 133.2 (CH), 129.3 (CH), 128.2 (C), 125.6 (CH), 120.5 (CH), 48.4 ($CH_3$), 36.8 ($CH_3$), 36.6 ($CH_3$).

NMR Spectrum of the Fluor

In DMSO-$d_6$ at 282.5 MHz, chemical shifts (ppm): −77.8.

Infrared Spectrum

IR spectrum was obtained as potassium bromide pellets. Absorption bands are given in $cm^{-1}$: 1721 (C=O), 1250, 1165, 1027.

Elemental Analyse

Anal. calcd for $C_{14}H_{15}F_3N_2O_5S$: C, 44.21; H, 3.98; N, 7.37; S, 8.43. Found: C, 43.95; H, 4.18; N, 7.25; S, 8.83%.

EXAMPLE 73

Preparation of Methyl 5,7-Bis(N,N-Dimethylcarbamate)-1-Methylquinolinium-3-Carboxylate Triflate

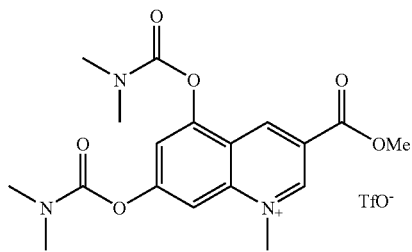

Stage A: 5,7-dihydroxyquinoline-3-carboxylic acid.

1 g (4.7 mmol) of 5,7-dimethoxy-3-cyanoquinoline [described in Tetrahedron Lett. 1998, 39, 4013-4016] dissolved in 20 mL of an aqueous solution of HBr (48Wt %) was heated under reflux for 24 hours. After cooling the reaction mixture to room temperature, the pH was adjusted between 5 and 6, and the precipitate was filtered off and dried at 70° C. 0.66 g (yield: 69%) of product of molecular formula $C_{10}H_7NO_4$ was obtained. Aspect: yellow powder.

Melting point: >260° C.

NMR Spectrum of the Proton

In DMSO-$d_6$ at 300 MHz, chemical shifts (ppm) and multiplicity: 11.0 (br, 1H), 10.6 (br, 1H); 9.11 (s, 1H), 8.87 (s, 1H), 6.80 (s, 1H), 6.61 (s, 1H).

Infrared Spectrum

IR spectrum was obtained as potassium bromide pellets. Absorption bands are given in cm$^{-1}$: 1651 (C=O), 1384, 1282, 785.

Stage B: methyl 5,7-dihydroxyquinoline-3-carboxylate.

To a solution of 0.2 g (1 mmol) of compound prepared in stage A in 15 mL of methanol was added at 0° C. 438 μL (6 mmol) of thionyl chloride. The reaction mixture was then heated under reflux overnight. The cooled mixture was then hydrolysed with 5 mL of water and neutralized with an aqueous solution of NaOH 2M. Extraction was performed with dichloromethane (3×30 mL). The combined organic layers were dried over MgSO$_4$, filtered and evaporated under reduce pressure giving 70 mg (yield: 32%) of product of molecular formula $C_{11}H_9NO_4$. Aspect: yellow powder.

NMR Spectrum of the Proton

In DMSO-$d_6$ at 300 MHz, chemical shifts (ppm) and multiplicity: 9.09 (s, 1H), 8.85 (s, 1H), 6.79 (s, 1H), 6.61 (s, 1H), 3.89 (s, 3H).

Stage C: methyl 5,7-bis(N,N-dimethylcarbamate)quinoline-3-carboxylate.

To a solution of 70 mg (0.32 mmol) of compound prepared in stage B in 15 mL of acetone was added finely powdered K$_2$CO$_3$ (0.442 g, 3.2 mmol) and 65 μL (0.70 mmol) of N,N-dimethylcarbamoyl chloride. This mixture was heated under reflux overnight and then filtered. After evaporation of the solvent, a purification by column chromatography on silica gel with cyclohexane/iPrOH (8/2) and 1% of triethylamine as eluent gave 42 mg (yield: 12%) of compound of molecular formula $C_{17}H_{19}N_3O_6$. Aspect: pale yellow powder.

Melting point: 135° C.

NMR Spectrum of the Proton

In CDCl$_3$ at 300 MHz, chemical shifts (ppm) and multiplicity: 9.40 (s, 1H), 8.90 (s, 1H), 7.73 (s, 1H), 7.38 (s, 1H), 3.99 (s, 3H), 3.24 (s, 3H), 3.12 (s, 3H), 3.06 (s, 3H), 3.02 (s, 3H).

NMR Spectrum of the Carbon

In CDCl$_3$ at 75 MHz, chemical shifts (ppm) and nature of the carbon: 165.8 (C), 154.0 (C), 153.9 (C), 153.8 (C), 150.9 (CH), 150.6 (C), 148.1 (C), 133.1 (CH), 122.5 (C), 119.3 (C), 117.3 (CH), 115.9 (CH), 52.6 (CH$_3$), 37.1 (CH$_3$), 36.9 (CH$_3$), 36.8 (CH$_3$), 36.7 (CH$_3$).

Infrared Spectrum

IR spectrum was obtained as potassium bromide pellets. Absorption bands are given in cm$^{-1}$: 1727, 1386, 1288, 1171.

Stage D: methyl 5,7-bis(N,N-dimethylcarbamate)-1-methylquinolinium-3-carboxylate triflate.

To 30 mg (0.08 mmol) of compound prepared in stage C dissolved in 1.5 mL of anhydrous dichloromethane was added, under N$_2$, 10 μL (0.09 mmol) of methyl trifluoromethanesulfonate. The reaction mixture was stirred overnight at room temperature. Evaporation of the solvent gave 43 mg (yield: 100%) of compound of molecular formula $C_{19}H_{22}F_3N_3O_9S$. Aspect: pale yellow powder.

NMR Spectrum of the Proton

In CDCl$_3$ at 300 MHz, chemical shifts (ppm) and multiplicity: 9.81 (s, 1H), 9.47 (s, 1H), 8.10 (s, 1H), 7.81 (s, 1H), 4.66 (s, 3H), 4.05 (s, 3H), 3.26 (s, 3H), 3.14 (s, 3H), 3.07 (s, 3H), 3.02 (s, 3H).

NMR Spectrum of the Carbon

In CDCl$_3$ at 75 MHz, chemical shifts (ppm) and nature of the carbon: 162.1 (C), 159.3 (C), 151.3 (CH), 150.5 (C), 141.9 (CH), 140.9 (C), 123.2 (C), 121.3 (C), 118.4 (CH), 106.9 (CH), 53.90 (CH$_3$), 47.08 (CH$_3$), 37.37 (CH$_3$), 37.09 (CH$_3$), 37.06 (CH$_3$), 36.90 (CH$_3$).

EXAMPLE 74

Methyl 8-(N,N-Dimethylcarbamate)-1-Methylquinolinium-3-Carboxylate Triflate

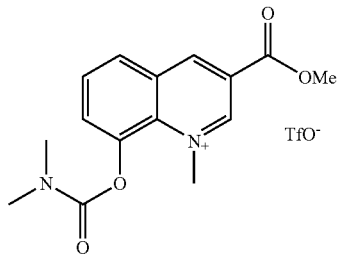

Stage A: methyl 8-methoxyquinoline-3-carboxylate.

To a solution of tert-butyl N-(2-formyl-6-methoxyphenyl) carbamate (2.85 g, 11.35 mmol) [described in Org. Lett. 2002, 4(1), 39-42] and methyl trans-3-methoxyacrylate (2.70 mL, 24.96 mmol) dissolved in 60 ml of methanol, was added slowly 40 mL of an aqueous solution of hydrochloric acid 3M. The resulting mixture was stirred under reflux for 3 hours. The reaction mixture was then cooled to room temperature and neutralised by adding Na$_2$CO$_3$. The aqueous solution was extracted with CH$_2$Cl$_2$ (4×70 mL). The combined organic layers were dried over MgSO$_4$, filtered and evaporated under vacuum giving 2.12 g of compound of molecular formula $C_{12}H_{11}NO_3$. The crude product was used without further purification in the next stage. Aspect: orange powder.

Melting point: 104° C.

NMR Spectrum of the Proton

In DMSO-$d_6$ at 300 MHz, chemical shifts (ppm) and multiplicity: 9.26 (d, J=2.1 Hz, 1H), 8.96 (d, J=2.1 Hz, 1H), 7.73 (d, J=8.1 Hz, 1H), 7.64 (dd, J=7.9 and 7.9 Hz, 1H), 7.36 (d, J=7.7 Hz, 1H), 3.99 (s, 3H), 3.96 (s, 3H).

NMR Spectrum of the Carbon

In DMSO-$d_6$ at 75 MHz, chemical shifts (ppm) and nature of the carbon: 165.3 (C), 155.1 (C), 147.8 (CH), 140.9 (C), 138.3 (CH), 128.1 (CH), 127.7 (C), 123.0 (C), 120.8 (CH), 111.0 (CH), 55.9 ($CH_3$), 52.6 ($CH_3$).

Infrared Spectrum

IR spectrum was obtained as potassium bromide pellets. Absorption bands are given in $cm^{-1}$: 1714 (C=O), 1381, 1281, 1129.

High Resolution Mass Spectrometry

HRMS (EI): calcd for ($M^+$) $C_{12}H_{11}NO_3$: m/z 217.0739. Found: 217.0726.

Stage B: 8-Hydroxyquinoline-3-carboxylic acid.

1.5 g (6.9 mmol) of compound prepared in stage A dissolved in 23 mL of an aqueous solution of HBr (48Wt %) was heated under reflux for 24 hours. After cooling the reaction mixture to room temperature, the pH was adjusted between 5 and 6, and the precipitate was filtered off and dried at 70° C. 0.89 g (yield: 68%) of product of molecular formula $C_{10}H_7NO_3$ was obtained. Aspect: brown solid.

Melting point: 109° C.

NMR Spectrum of the Proton

In DMSO-$d_6$ at 300 MHz, chemical shifts (ppm) and multiplicity: 10.18 (br, 1H), 9.23 (s, 1H), 8.90 (s, 1H), 7.56 (m, 2H), 7.21 (dd, J=7.4 and 1.5 Hz, 1H).

NMR Spectrum of the Carbon

In DMSO-$d_6$ at 75 MHz, chemical shifts (ppm) and nature of the carbon: 166.7 (C), 153.8 (C), 147.8 (CH), 140.1 (C.°), 138.9 (CH), 128.8 (CH), 128.0 (C), 124.3 (C), 119.5 (CH), 114.4 (CH).

Stage C: Methyl 8-hydroxyquinoline-3-carboxylate.

To a solution of 0.3 g (1.59 mmol) of compound prepared in stage B in 20 mL of methanol was added at 0° C. 694 µL (9.52 mmol) of thionyl chloride. The reaction mixture was then heated under reflux overnight. The cooled mixture was then neutralized with a saturated aqueous solution of $NaHCO_3$. Extraction was performed with dichloromethane (3×30 mL). The combined organic layers were dried over $MgSO_4$, filtered and evaporated under reduced pressure. A purification by column chromatography on silica gel with ethyl acetate/dichloromethane (3/2) as eluent gave 138 mg (yield: 43%) of compound of molecular $C_{11}H_9NO_3$. Aspect: yellow powder.

Melting point: 140° C.

NMR Spectrum of the Proton

In $CDCl_3$ at 300 MHz, chemical shifts (ppm) and multiplicity: 9.32 (d, J=1.9 Hz, 1H), 8.85 (d, J=2.1 Hz, 1H), 8.15 (br, 1H), 7.54 (dd, J=8.1 and 7.7 Hz, 1H), 7.45 (dd, J=8.3 and 1.3 Hz, 1H), 7.29 (dd, J=7.5 and 1.3 Hz, 1H), 4.03 (s, 3H).

Infrared Spectrum

IR spectrum was obtained as potassium bromide pellets. Absorption bands are given in $cm^{-1}$: 1731 (C=O), 1500, 1240, 1212, 772.

Elemental Analyse

Anal. calcd for $C_{11}H_9NO_3$: C, 65.02; H, 4.46; N, 6.89. Found: C, 64.62; H, 4.36; N, 6.96%.

Stage D: Methyl 8-(N,N-dimethylcarbamate)quinoline-3-carboxylate.

To a solution of 123 mg (0.60 mmol) of compound prepared in stage C in 50 mL of acetone was added finely powdered $K_2CO_3$ (0.417 g, 3.0 mmol) and 67 µL (0.72 mmol) of N,N-dimethylcarbamoyl chloride. This mixture was heated under reflux overnight and then filtered. After evaporation of the solvent, a purification by column chromatography on silica gel with cyclohexane/iPrOH (8/2) and 1% of triethylamine as eluent gave 123 mg (yield: 75%) of compound of molecular formula $C_{14}H_{14}N_2O_4$. Aspect: pale yellow powder.

Melting point: 98° C.

NMR Spectrum of the Proton

In $CDCl_3$ at 300 MHz, chemical shifts (ppm) and multiplicity: 9.44 (d, J=1.9 Hz, 1H), 8.81 (d, J=2.1 Hz, 1H), 7.77 (m, 1H), 7.57 (m, 2H), 3.98 (s, 3H), 3.27 (s, 3H), 3.06 (s, 3H).

Infrared Spectrum

IR spectrum was obtained as potassium bromide pellets. Absorption bands are given in $cm^{-1}$: 1723 (C=O), 1376, 1165, 776.

Elemental Analyse

Anal. calcd for $C_{14}H_{14}N_2O_4$: C, 61.31; H, 5.14; N, 10.21. Found: C, 61.26; H, 5.16; N, 10.18%.

Stage E: Methyl 8-(N,N-dimethylcarbamate)-1-methylquinolinium-3-carboxylate triflate.

To 116 mg (0.42 mmol) of compound prepared in stage D dissolved in 10 mL of anhydrous dichloromethane was added, under $N_2$, 53 µL (0.47 mmol) of methyl trifluoromethanesulfonate. The reaction mixture was stirred overnight at room temperature. Evaporation of the solvent gave 182 mg (yield: 100%) of compound of molecular formula $C_{16}H_{17}F_3N_2O_7S$. Aspect: pale yellow powder.

Melting point: 102° C.

NMR Spectrum of the Proton

In $CDCl_3$ at 300 MHz, chemical shifts (ppm) and multiplicity: 9.64 (s, 1H), 9.47 (s, 1H), 8.23 (d, J=7.7 Hz, 1H), 7.89 (m, 2H), 4.81 (s, $CH_3$), 3.98 (s, $CH_3$), 3.20 (s, $CH_3$), 3.03 (s, $CH_3$).

NMR Spectrum of the Carbon

In $CDCl_3$ at 75 MHz, chemical shifts (ppm) and nature of the carbon: 161.7 (C), 153.3 (C), 152.8 (CH), 148.7 (CH), 142.2 (C), 133.7 (C), 133.5 (CH), 131.2 (CH), 130.9 (C), 130.12 (CH), 124.3 (C), 53.7 ($CH_3$), 51.1 ($CH_3$), 37.2 ($CH_3$), 36.8 ($CH_3$).

NMR Spectrum of the Fluor

In $CDCl_3$ at 282.5 MHz, chemical shifts (ppm): −78.8.

Elemental Analyse

Anal. calcd for $C_{16}H_{17}F_3N_2O_7S$: C, 43.84; H, 3.91; N, 6.39; S, 7.31. Found: C, 44.12; H, 4.04; N, 6.42; S, 7.69%.

Infrared Spectrum

IR spectrum was obtained as potassium bromide pellets. Absorption bands are given in $cm^{-1}$: 1735, 1263, 1153, 1031.

EXAMPLE 75

2-Methyl-5-(N,N-Dimethylthiocarbamate)-O-Isoquinolinium Triflate

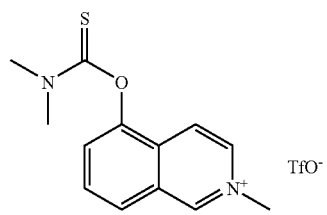

Stage A: 5-(N,N-dimethylthiocarbamate)-O-isoquinoline.

To a solution of 480 mg (3.30 mmol) of 5-hydroxyisoquinoline in 50 mL of acetone was added finely powdered $K_2CO_3$ (2.28 g, 16.5 mmol) and 490 mg (3.96 mmol) of N,N-dimethylthiocarbamoyl chloride. This mixture was heated under reflux overnight and then filtered. After evaporation of the solvent, the crude product was dissolved in 30 mL of dichloromethane and washed with an aqueous solution of $Na_2CO_3$ 2M. The organic layer was dried over $MgSO_4$, filtered and evaporated under reduced pressure. The solid obtained was triturated with pentane giving 0.733 g (yield: 96%) of compound of molecular formula $C_{12}H_{12}N_2OS$. Aspect: pale yellow powder.

Melting point: 137° C.

NMR Spectrum of the Proton

In $CDCl_3$ at 300 MHz, chemical shifts (ppm) and multiplicity: 9.28 (s, 1H), 8.52 (d, J=6.0 Hz, 1H), 7.88 (d, J=8.3 Hz, 1H), 7.61 (m, 2H), 7.41 (d, J=7.5 Hz, 1H), 3.50 (s, 3H), 3.49 (s, 3H).

NMR Spectrum of the Carbon

In $CDCl_3$ at 75 MHz, chemical shifts (ppm) and nature of the carbon: 187.3 (C), 152.5 (CH), 148.8 (C), 143.4 (CH), 130.3 (C), 129.4 (C), 126.9 (CH), 125.6 (CH), 124.0 (CH), 114.6 (CH), 43.5 ($CH_3$), 38.9 ($CH_3$).

Infrared Spectrum

IR spectrum was obtained as potassium bromide pellets. Absorption bands are given in $cm^{-1}$: 1542 (C=S), 1400, 1375, 1124.

Stage B: 2-methyl-5-(N,N-dimethylthiocarbamate)-O-isoquinolinium triflate.

To 100 mg (0.43 mmol) of compound prepared in stage A dissolved in 5 mL of anhydrous dichloromethane was added, under $N_2$, 54 µL (0.47 mmol) of methyl trifluoromethanesulfonate. The reaction mixture was stirred overnight at room temperature. Evaporation of the solvent and trituration of the solid with diethyl ether gave 151 mg (yield: 89%) of compound of molecular formula $C_{14}H_{15}F_3N_2O_4S_2$. Aspect: pale yellow powder.

Melting point: 115° C.

NMR Spectrum of the Proton

In $CDCl_3$ at 300 MHz, chemical shifts (ppm) and multiplicity: 9.99 (s, 1H), 8.47 (d, J=7.0 Hz, 1H), 8.35 (d, J=8.3 Hz, 1H), 8.24 (d, J=6.8 Hz, 1H), 7.93 (dd, J=7.9 and 8.1 Hz, 1H), 7.78 (d, J=7.5 Hz, 1H), 4.54 (s, 3H), 3.51 (s, 3H), 3.47 (s, 3H).

NMR Spectrum of the Carbon

In $CDCl_3$ at 75 MHz, chemical shifts (ppm) and nature of the carbon: 186.1 (C), 149.1 (C), 132.2 (C), 131.8 (CH), 131.1 (CH), 128.8 (CH), 128.7 (C), 121.7 (CH), 48.6 ($CH_3$), 43.9 ($CH_3$), 39.4 ($CH_3$).

NMR Spectrum of the Fluor

In $CDCl_3$ at 282.5 MHz, chemical shifts (ppm): −78.9.

Infrared Spectrum

IR spectrum was obtained as potassium bromide pellets. Absorption bands are given in $cm^{-1}$: 1557 (C=S), 1278, 1164, 1029.

EXAMPLE 76

Methyl 1-Methyl-5-(N-Ethylcarbamate)-1,4-Dihydroquinoline-3-Carboxylate

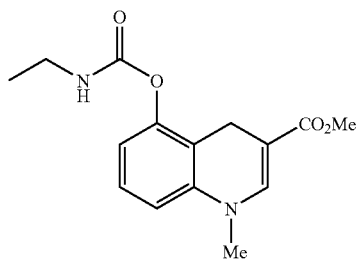

Stage A: Methyl 5-(N-ethylcarbamate)-quinoline-3-carboxylate.

To 321 mg (1.58 mmol) of compound prepared in stage C of example 67 dissolved in dry tetrahydrofuran (10 mL) was added 0.10 g (1.90 mmol) of NaH (50% dispersion in mineral oil). The reaction mixture was stirred for 1 hour and then 130 µL (1.64 mmol) of ethyl isocyanate was introduced before heating under reflux overnight. After cooling to room temperature, 15 mL of water was added and the THF was evaporated under reduced pressure. The aqueous layer was extracted with dichloromethane (3×10 mL). The combined organic layers were dried over MgSO4, filtered and evaporated under vacuum. A purification by column chromatography on silica gel with petroleum ether/iPrOH (3/1) as eluent gave 408 mg (yield: 94%) of compound of molecular formula $C_{14}H_{14}N_2O_4$.

NMR Spectrum of the Proton

In $CDCl_3$ at 300 MHz, chemical shifts (ppm) and multiplicity: 9.43 (d, 1.7 Hz, 1H), 8.98 (d, J=1.7 Hz, 1H), 8.03 (d, J=8.5 Hz, 1H), 7.80 (t, J=8.1 Hz, 1H), 7.47 (d, J=7.7 Hz, 1H), 5.39 (t, J=7.2 Hz, 1H), 3.36 (quint, J=7.2 Hz, 2H), 1.29 (t, J=7.2 Hz, 3H).

Mass Spectrometry

EI ($MH^+$) $C_{15}H_{14}N_2O_4$: m/z 275.

Stage B: Methyl 5-(N-ethylcarbamate)-1-methylquinolinium-3-carboxylate triflate.

To 80 mg (0.27 mmol) of compound prepared in stage A dissolved in 2 mL of anhydrous dichloromethane was added, under $N_2$, 36 µL (0.32 mmol) of methyl trifluoromethanesulfonate. The reaction mixture was stirred for 2 hours at room temperature. Evaporation of the solvent gave 125 mg (yield: 100%) of compound of molecular formula $C_{16}H_{17}F_3N_2O_7S$. Aspect: white powder.

NMR Spectrum of the Proton

In DMSO-$d_6$ at 300 MHz, chemical shifts (ppm) and multiplicity: 10.07 (s, 1H), 9.49 (s, 1H), 8.48 (t, J=5.8 Hz, 1H), 8.42 (m, 2H), 8.04 (dd, J=3.2 Hz and 5.3 Hz, 1H), 4.73 (s, 3H), 4.05 (s, 3H), 3.18 (q, J=7.2 Hz, 2H), 1.20 (t, J=7.2 Hz, 3H).

NMR Spectrum of the Carbon

In DMSO-$d_6$ at 75 MHz, chemical shifts (ppm): 162.7, 153.0, 151.2, 149.0, 141.2, 140.1, 138.3, 123.9, 123.2, 122.7, 116.2, 53.9, 46.3, 36.0, 15.0.

Stage C: Methyl 5-(N-ethylcarbamate)-1-methyl-1,4-dihydroquinoline-3-carboxylate.

50 mg (0.11 mmol) of compound prepared in stage B was dissolved in 3 mL of degassed $CH_2Cl_2$ ($N_2$) and 3 mL of degassed water ($N_2$) and under an atmosphere of nitrogen. 92 mg (0.53 mmol) of sodium dithionite dissolved in 1 mL of degassed water ($N_2$) and 34 mg (0.32 mmol) of $Na_2CO_3$ dissolved in 1 mL of degassed water ($N_2$) were introduced simultaneously. The reaction mixture was stirred for 1 hour and the same quantity of sodium dithionite and $Na_2CO_3$ were introduced in the same way. After stirring 1 hour the reaction mixture, 184 mg (1.06 mmol) of sodium dithionite dissolved in 2 mL of degassed water ($N_2$) and 68 mg (0.64 mmol) of $Na_2CO_3$ dissolved in 2 mL of degassed water ($N_2$) were introduced simultaneously. Stirring was pursued for 1 supplementary hour. 100 μL of glacial acetic acid was added and the organic layer was separated. After extraction of the aqueous layer with dichloromethane (3×10 mL), the organic layers were combined, dried over $MgSO_4$, filtered and evaporated under reduced pressure at room temperature giving 20 mg (yield: 62%) of compound of molecular formula $C_{15}H_{18}N_2O_4$. Aspect: yellow powder.

NMR Spectrum of the Proton

In $CDCl_3$ at 300 MHz, chemical shifts (ppm) and multiplicity: 7.19 (s, 1H), 7.11 (t, J=8.1 Hz, 1H), 6.77 (J=8.3 Hz, 1H), 6.55 (d, J=8.3 Hz, 1H), 5.14 (s, 1H), 3.71 (s, 3H), 3.62 (s, 2H), 3.28 (q, J=7.2 Hz, 2H), 3.18 (s, 3H), 1.20 (t, J=7.2 Hz, 3H).

NMR Spectrum of the Carbon

In $CDCl_3$ at 75 MHz, chemical shifts (ppm) and nature of the carbon: 168.6 (C), 154.3 (C), 150.0 (C), 143.2 (CH), 140.4 (C), 127.7 (CH), 117.3 (CH), 117.1 (C), 110.0 (CH), 97.1 (C), 51.4 ($CH_3$), 39.7 ($CH_3$), 36.6 ($CH_2$), 21.6 ($CH_2$), 15.5 ($CH_3$).

EXAMPLE 77

Ethyl 1-Methyl-8-(N,N-Dimethylcarbamate)Quinolinium-3-Carboxylate Triflate

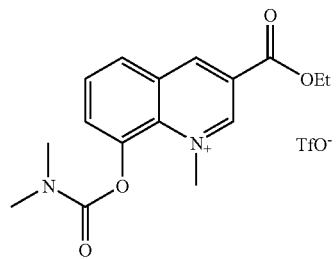

Stage A: Ethyl 8-hydroxyquinoline-3-carboxylate.

To a solution of 950 mg (5.02 mmol) of compound prepared in stage B of example 74 in 60 mL of ethanol was added at 0° C. 2.2 mL (30.13 mmol) of thionyl chloride. The reaction mixture was then heated under reflux overnight. The cooled mixture was then neutralized with a saturated aqueous solution of $NaHCO_3$. Extraction was performed with dichloromethane (3×30 mL). The combined organic layers were dried over $MgSO_4$, filtered and evaporated under reduced pressure. A purification by column chromatography on silica gel with ethyl acetate/dichloromethane (3/2) as eluent gave 719 mg (yield: 66%) of compound of molecular $C_{12}H_{11}NO_3$. Aspect: pale brown powder.

Melting point: 118° C.

NMR Spectrum of the Proton

In DMSO-$d_6$ at 300 MHz, chemical shifts (ppm) and multiplicity: 10.22 (br, 1H), 9.23 (s, 1H), 8.94 (s, 1H), 7.62 (d, J=7.2 Hz, 1H), 7.54 (dd, J=7.7 and 8.1 Hz, 1H), 7.23 (d, J=7.4 Hz, 1H), 4.41 (q, J=7.2 Hz, 2H), 1.38 (t, J=7.2 Hz, 3H).

NMR Spectrum of the Carbon

In DMSO-$d_6$ at 75 MHz, chemical shifts (ppm) and nature of the carbon: 164.8 (C), 153.6 (C), 147.0 (CH), 139.9 (C), 138.5 (CH), 128.7 (CH), 127.5 (C), 123.1 (C), 119.3 (CH), 114.3 (CH), 61.3 ($CH_2$), 14.2 ($CH_3$).

Infrared Spectrum

IR spectrum was obtained as potassium bromide pellets. Absorption bands are given in $cm^{-1}$: 1718 (C=O), 1502, 1257, 1189, 778.

Elemental Analyse

Anal. calcd for $C_{12}H_{11}NO_3$: C, 66.35; H, 5.10; N, 6.45. Found: C, 66.43; H, 5.17; N, 6.42%.

Stage B: Ethyl 8-(N,N-dimethylcarbamate)quinoline-3-carboxylate.

To a solution of 300 mg (1.38 mmol) of compound prepared in stage A in 150 mL of acetone was added finely powdered $K_2CO_3$ (954 g, 6.91 mmol) and 153 μL (1.66 mmol) of N,N-dimethylcarbamoyl chloride. This mixture was heated under reflux overnight and then filtered. After evaporation of the solvent, a purification by column chromatography on silica gel with cyclohexane/iPrOH (4/1) and 1% of triethylamine as eluent gave 339 mg (yield: 87%) of compound of molecular formula $C_{15}H_{16}N_2O_4$. Aspect: pale yellow powder.

Melting point: 91° C.

NMR Spectrum of the Proton

In $CDCl_3$ at 300 MHz, chemical shifts (ppm) and multiplicity: 9.47 (s, 1H), 8.84 (s, 1H), 7.80 (m, 1H), 7.58 (m, 2H), 4.46 (q, J=7.2 Hz, 2H), 3.30 (s, 3H), 3.08 (s, 3H), 1.45 (t, J=7.2 Hz, 3H).

NMR Spectrum of the Carbon

In $CDCl_3$ at 75 MHz, chemical shifts (ppm) and nature of the carbon: 165.1 (C), 155.0 (C), 150.0 (CH), 148.1 (C), 143.4 (C), 138.5 (CH), 128.0 (C), 127.2 (CH), 126.5 (CH), 124.0 (CH), 123.6 (C), 61.5 ($CH_2$), 36.8 ($CH_3$), 14.3 ($CH_3$).

Infrared Spectrum

IR spectrum was obtained as potassium bromide pellets. Absorption bands are given in $cm^{-1}$: 1719 (C=O), 1373, 1270, 1232, 1165.

Stage C: Ethyl 8-(N,N-dimethylcarbamate)-1-methylquinolinium-3-carboxylate triflate.

To 153 mg (0.53 mmol) of compound prepared in stage B dissolved in 10 mL of anhydrous dichloromethane was added, under $N_2$, 66 μL (0.58 mmol) of methyl trifluoromethanesulfonate. The reaction mixture was stirred for 3 hours at room temperature. Evaporation of the solvent and trituration of the solid with diethyl ether gave 196 mg (yield: 82%) of compound of molecular formula $C_{17}H_{19}F_3N_2O_7S$. Aspect: pale yellow powder.

Melting point: 136° C.

NMR Spectrum of the Proton

In $CDCl_3$ at 300 MHz, chemical shifts (ppm) and multiplicity: 9.69 (s, 1H), 9.48 (s, 1H), 8.25 (dd, J=7.9 and 1.3 Hz, 1H), 7.97 (dd, J=7.9 and 7.9 Hz, H), 7.89 (dd, J=7.7 and 1.3 Hz, 1H), 4.88 (s, $CH_3$), 4.49 (q, J=7.2 Hz, 2H), 3.24 (s, $CH_3$), 3.07 (s, $CH_3$), 1.44 (t, J=7.2 Hz, 3H).

NMR Spectrum of the Carbon

In $CDCl_3$ at 75 MHz, chemical shifts (ppm) and nature of the carbon: 161.2 (C), 153.5 (C), 153.0 (CH), 148.7 (CH), 142.4 (C), 134.0 (C), 133.6 (CH), 131.3 (CH), 131.1 (C), 130.2 (CH), 124.9 (C), 63.6 ($CH_2$), 51.4 ($CH_3$), 37.4 ($CH_3$), 37.0 ($CH_3$), 14.1 ($CH_3$).

NMR Spectrum of the Fluor
In CDCl$_3$ at 282.5 MHz, chemical shifts (ppm): −78.8.
Infrared Spectrum
IR spectrum was obtained as potassium bromide pellets. Absorption bands are given in cm$^{-1}$: 1739 (C=O), 1260, 1154.

EXAMPLE 78

1-Methyl-3-(N-Propylcarboxamido)-7-(N,N-Dimethylcarbamate)-1,4-Dihydroquinoline

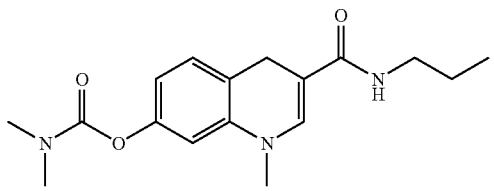

Stage A: 7-hydroxy-3-(N-propylcarboxamido)quinoline.

To 100 mg (0.46 mmol) of compound prepared in stage B of example 1, dissolved in 5 mL of toluene, was added under N$_2$, 94 mg (0.97 mmol) N-propylamine hydrochloride dissolved in 1 ml (2 mmol) of trimethylaluminum (2M in heptane). The reaction mixture was then heated under reflux for 5 days. Evaporation and chromatography on silica gel with dichloromethane/ethanol (9/1) as eluent gave 25 mg (yield: 25%) of product of molecular formula C$_{13}$H$_{14}$N$_2$O$_2$. Aspect: pale brown powder.
Melting point: 198° C.
NMR Spectrum of the Proton
In DMSO-d$_6$ at 300 MHz, chemical shifts (ppm) and multiplicity: 10.51 (br, 1H), 9.14 (d, J=2.1 Hz, 1H), 8.67 (m, 2H), 7.92 (d, J=8.9 Hz, 1H), 7.25 (m, 2H), 3.26 (q, J=6.8 Hz, 2H), 1.58 (sext, J=7.4 Hz, 2H), 0.91 (t, J=7.4 Hz, 3H).
NMR Spectrum of the Carbon
In DMSO-d$_6$ at 75 MHz, chemical shifts (ppm): 165.0 (C), 160.1 (C), 150.5 (C), 149.1 (CH), 135.0 (CH), 130.6 (CH), 124.4 (C), 120.8 (C), 120.1 (CH), 109.9 (CH), 41.1 (CH$_2$), 22.5 (CH$_2$), 11.6 (CH$_3$).

Stage B: 7-(N,N-dimethylcarbamate)-3-(N-propylcarboxamido)quinoline

To a solution of compound obtained in stage A (170 mg, 0.74 mmol) in dry THF (10 mL) was added 43 mg (1.77 mmol) of NaH (50% dispersion in mineral oil). The mixture was stirred at room temperature for 1 hour after which time dimethylcarbamoyl chloride (81 L, 0.89 mmol) was added. The resulting mixture was refluxed for 12 hours. After addition of water (10 mL) and extraction with CH$_2$Cl$_2$ (3×15 mL), the resulting combined organic layers were dried over MgSO$_4$, filtered and evaporated under vacuum to give 215 mg (yield: 97%) of compound of molecular formula C$_{16}$H$_{19}$N$_3$O$_3$. Aspect: pale yellow powder.
Melting point: 168° C.
NMR Spectrum of the Proton
In CDCl$_3$ at 300 MHz, chemical shifts (ppm) and multiplicity: 9.16 (d, J=2.3 Hz, 1H), 8.47 (d, J=2.1 Hz, 1H), 7.78 (m, 2H), 7.40 (dd, J=9.0 and 2.3 Hz, 1H), 6.59 (br, 1H), 3.47 (q, J=7.3 Hz, 2H), 3.17 (s, 3H), 3.06 (s, 3H), 1.68 (sext, J=7.2 Hz, 2H), 1.01 (t, J=7.3 Hz, 3H).
NMR Spectrum of the Carbon
In CDCl$_3$ at 75 MHz, chemical shifts (ppm) and nature of the carbon: 165.7 (C), 154.5 (C), 153.5 (C), 149.8 (C), 148.7 (CH), 135.3 (CH), 129.7 (CH), 127.0 (C), 124.6 (C), 123.6 (CH), 120.2 (CH), 42.1 (CH$_2$), 37.0 (CH$_3$), 36.8 (CH$_3$), 23.0 (CH$_2$), 11.6 (CH$_3$).

Stage C: 7-(N,N-dimethylcarbamate)-3-(N-propylcarboxamido)-1-methylquinolinium triflate To 50 mg (0.17 mmol) of compound prepared in stage B dissolved in 5 mL of anhydrous dichloromethane was added, under N$_2$, 24 µL (0.20 mmol) of methyl trifluoromethanesulfonate. The reaction mixture was stirred for 2 hours at room temperature. Evaporation of the solvent gave 72 mg (yield: 93%) of compound of molecular formula C$_{18}$H$_{22}$F$_3$N$_3$O$_6$S. Aspect: pale yellow powder.
Melting point: 190° C.
NMR Spectrum of the Proton
In CDCl$_3$ at 300 MHz, chemical shifts (ppm) and multiplicity: 9.75 (s, 1H), 9.60 (s, 1H), 8.53 (br, 1H), 8.42 (d, J=9.1 Hz, 1H), 8.19 (s, 1H), 7.80 (d, J=8.9 Hz, 1H), 4.66 (s, 3H), 3.45 (q, J=6.8 Hz, 2H), 3.20 (s, 3H), 3.09 (s, 3H), 1.70 (sext, J=7.4 Hz, 2H), 0.97 (t, J=7.3 Hz, 3H).
NMR Spectrum of the Fluor
In CDCl$_3$ at 282.5 MHz, chemical shifts (ppm): −78.6.

Stage D: 1-methyl-3-(N-propylcarboxamido)-7-(N,N-dimethylcarbamate)-1,4-dihydroquinoline 20 mg (0.04 mmol) of compound prepared in stage C was dissolved in 6 mL of degassed CH$_2$Cl$_2$ (N$_2$) and 6 mL of degassed water (N$_2$) and under an atmosphere of nitrogen. 38 mg (0.20 mmol) of sodium dithionite dissolved in, 1 ml of degassed water (N$_2$) and 14 mg (0.12 mmol) of Na$_2$CO$_3$ dissolved in 1 mL of degassed water (N$_2$) were introduced simultaneously. The reaction mixture was stirred for 1 hour and the same quantity of sodium dithionite and Na$_2$CO$_3$ were introduced in the same way. After stirring 1 hour the reaction mixture, 76 mg (0.40 mmol) of sodium dithionite dissolved in 2 mL of degassed water (N$_2$) and 28 mg (0.24 mmol) of Na$_2$CO$_3$ dissolved in 2 mL of degassed water (N$_2$) were introduced simultaneously. Stirring was pursued for 1 supplementary hour. 100 µL of glacial acetic acid was added and the organic layer was separated. After extraction of the aqueous layer with dichloromethane (3×10 mL), the organic layers were combined, dried over MgSO$_4$, filtered and evaporated under reduced pressure at room temperature giving 10 mg (yield: 79%) of compound of molecular formula C$_{17}$H$_{23}$N$_3$O$_3$.
NMR Spectrum of the Proton
In CDCl$_3$ at 300 MHz, chemical shifts (ppm) and multiplicity: 7.14 (s, 1H), 6.92 (d, J=8.1 Hz, 1H), 6.59 (dd, J=8.1 and 2.1 Hz, 1H), 6.41 (d, J=2.1 Hz, 1H), 5.29 (br, 1H), 3.66 (s, 2H), 3.25 (q, J=6.8 Hz, 2H), 3.10 (s, 3H), 3.03 (s, 3H), 2.94 (s, 3H), 1.50 (sext, J=7.5 Hz, 2H), 0.88 (t, J=7.4 Hz, 3H).

EXAMPLE 79

Ethyl 1-Methyl 5-(N,N-Dimethylcarbamate)Pyridinium-3-Carboxylate Triflate

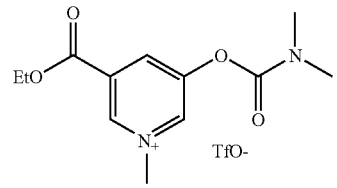

Stage A: 5-hydroxynicotinic acid

To 10.1 g (0.05 mol) of 5-bromonicotinic acid was added 10 g of NaOh dissolved in 63 mL of water, 3.1 g of coppersulfate pentahydrate and 0.42 g of copper (0). The reaction mixture was vigorously stirred and heated under reflux for 30 hours. After cooling the mixture to room temperature, 4.8 g of $Na_2S.H_2O$ was added and stirring was pursued overnight. The reaction mixture was heated to 70° C. and treated with $H_2S$ gas until disappearance of the white precipitate (3 h). After cooling to room temperature, the mixture was filtered and the pH of the filtrate was adjusted to 5.2 with concentrated hydrochloric acid. The precipitate was filtered and the pH of the % filtrate was adjusted to 4.6 with concentrated hydrochloric acid. The white precipitate was then filtered, washed with water and dried under reduced pressure giving 4.3 g (yield: 62%) of product of molecular formula $C_7H_5NO_3$. Aspect: white powder.

Melting point: >260° C.

NMR Spectrum of the Proton

In DMSO-$d_6$ at 300 MHz, chemical shifts (ppm) and multiplicity: 8.48 (d, J=1.5 Hz, 1H), 8.26 (d, J=2.6 Hz, 1H), 7.51 (d, J=1.9 Hz, 1H).

Infrared Spectrum

IR spectrum was obtained as potassium bromide pellets. Absorption bands are given in $cm^{-1}$: 3273, 1538, 1393, 1294.

Stage B: ethyl 5-hydroxynicotinate

To 2.5 g (18 mmol) of compound prepared in stage A dissolved in 50 mL of ethanol and cooled to 0° C. was added carefully 4.4 mL (61 mmol) of thionyl chloride. The reaction mixture was then heated under reflux for 24 hours and then evaporated under reduce pressure. The crude product was poured into water and then filtered giving 2.5 g (yield: 83%) of compound of molecular formula $C_8H_9NO_3$. Aspect: white powder.

Melting point: 150° C.

NMR Spectrum of the Proton

In DMSO-$d_6$ at 300 MHz, chemical shifts (ppm) and multiplicity: 8.74 (d, J=1.2 Hz, 1H), 8.60 (d, J=2.6 Hz, 1H), 8.07 (m, 1H), 4.44 (q, J=7.1 Hz, 2H), 1.42 (t, J=7.1 Hz, 3H).

Infrared Spectrum

IR spectrum was obtained as potassium bromide pellets. Absorption bands are given in $cm^{-1}$: 3044, 2874, 2677, 1731.

Stage C: ethyl 5-(N,N-dimethylcarbamate)pyridine-3-carboxylate

To a solution of compound obtained in stage B (200 mg, 1.2 mmol) in dry THF (20 mL) was added 66 mg (1.32 mmol) of NaH (50% dispersion in mineral oil). The mixture was stirred at room temperature for 1 hour after which time dimethylcarbamoyl chloride (120 L, 1.32 mmol) was added. The resulting mixture was refluxed for 2 hours. After addition of water (10 mL) and extraction with $CH_2Cl_2$ (3×15 mL), the resulting combined organic layers were dried over $MgSO_4$, filtered and evaporated under vacuum to give 280 mg (yield: 99%) of compound of molecular formula $C_{11}H_{14}N_2O_4$. Aspect: orange oil.

NMR Spectrum of the Proton

In $CDCl_3$ at 300 MHz, chemical shifts (ppm) and multiplicity: 8.96 (d, J=1.5 Hz, 1H), 8.52 (d, J=2.6 Hz, 1H), 8.00 (d, J=1.9 Hz, 1H), 4.31 (q, J=7.1 Hz, 2H), 2.74 (s, 3H), 2.65 (s, 3H), 1.31 (t, J=7.1 Hz, 3H).

Stage D: ethyl 1-methyl 5-(N,N-dimethylcarbamate)pyridinium-3-carboxylate triflate To 270 mg (1.13 mmol) of compound prepared in stage C dissolved in 20 mL of anhydrous dichloromethane was added, under $N_2$, 143 µL (1.26 mmol) of methyl trifluoromethanesulfonate. The reaction mixture was stirred for 2 hours at room temperature. Evaporation of the solvent and subsequent trituration with diethyl ether gave 280 mg (yield: 61%) of compound of molecular formula $C_{13}H_{17}F_3N_2O_7S$. Aspect: white powder.

Melting point: 110° C.

NMR Spectrum of the Proton

In $D_2O$ at 300 MHz, chemical shifts (ppm) and multiplicity: 9.23 (s, 1H), 8.98 (s, 1H), 8.79 (s, 1H), 4.43 (m, 5H), 3.07 (s, 3H), 2.95 (s, 3H), 1.34 (t, J=7.1 Hz, 3H).

NMR Spectrum of the Carbon

In DMSO-$d_6$ at 75 MHz, chemical shifts (ppm): 161.5 (C), 152.2 (C), 149.9 (C), 143.6 (CH), 138.4 (C), 130.1 (CH), 63.2 ($CH_2$), 48.9 ($CH_3$), 37.0 ($CH_3$), 36.6 ($CH_3$), 14.3 ($CH_3$).

Elemental Analyse

Anal. calcd for $C_{12}H_{17}F_3N_2O_7S$: C, 38.31; H. 4.26; N, 6.96; S, 7.97. Found: C, 38.62; H. 4.21; N, 6.86; S, 8.03%.

EXAMPLE 80

Ethyl 1-[4-(N,N-Dimethylcarbamate)Benzyl)]Pyridinium-3-Carboxylate Iodide

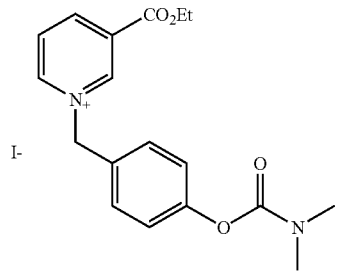

Stage A: 4-(hydroxymethyl)phenyl dimethylcarbamate

To a solution of 5 g (40.3 mmol) of 4-(hydroxymethyl) phenol in 500 mL of acetone was added finely powdered $K_2CO_3$ (27.83 g, 0.2 mol) and 3.71 mL (40.3 mmol) of N,N-dimethylcarbamoyl chloride. This mixture was heated under reflux overnight and then filtered. After evaporation of the solvent, a purification by column chromatography on silica gel with cyclohexane/iPrOH (9/1) and as eluent gave 7.16 g (yield: 91%) of compound of molecular formula $C_{10}H_{13}NO_3$. Aspect: white powder.

Melting point: 76° C.

NMR Spectrum of the Proton

In $CDCl_3$ at 300 MHz, chemical shifts (ppm) and multiplicity: 7.34 (d, J=8.5 Hz, 2H), 7.09 (d, J=8.5 Hz, 2H), 4.66 (d, J=6.0 Hz, 2H), 3.10 (s, 3H), 3.01 (s, 3H), 1.75 (t, J=5.8 Hz, 1H).

NMR Spectrum of the Carbon

In $CDCl_3$ at 75 MHz, chemical shifts (ppm): 155.1 (C), 150.7 (C), 138.3 (C), 127.9 (CH), 121.7 (CH), 64.4 ($CH_2$), 36.7 ($CH_3$), 36.5 ($CH_3$).

Stage B: 4-(chloromethyl)phenyl dimethylcarbamate 2,4,6-trichloro[1,3,5]triazine (1.78 g, 9.65 mmol) was added to DMF (2.5 mL), maintained at 25° C. After the formation of a white solid (2 hours), $CH_2Cl_2$ (25 mL) was added, followed by the compound prepared in stage A (1.79 g, 9.17 mmol). After the addition, the mixture was stirred overnight at room temperature. Water (20 mL) was added, and then the organic layer was washed with 15 mL of a saturated aqueous solution of $Na_2CO_3$, followed by 1N aqueous HCL and brine. The organic layers were dried over MgSO4 and evaporated under vacuum giving 1.82 g (yield: 92%) of compound of molecular formula $C_{10}H_{12}ClNO_2$. Aspect: pale yellow powder.

Melting point: 68° C.

NMR Spectrum of the Proton

In $CDCl_3$ at 300 MHz, chemical shifts (ppm) and multiplicity: 7.37 (d, J=8.5 Hz, 2H), 7.10 (d, J=8.7 Hz, 2H), 4.58 (s, 2H), 3.10 (s, 3H), 3.01 (s, 3H).

NMR Spectrum of the Carbon

In $CDCl_3$ at 75 MHz, chemical shifts (ppm): 154.8 (C), 151.6 (C), 134.4 (C), 129.7 (CH), 122.1 (CH), 45.8 ($CH_2$), 36.8 ($CH_3$), 36.6 ($CH_3$).

Stage C: Ethyl 1-[4-(N,N-dimethylcarbamate)benzyl)]pyridinium-3-carboxylate iodide A mixture of ethyl nicotinate (71 mg, 0.47 mmol), compound prepared in stage B (100 mg, 0.47 mmol) and potassium iodide (78 mg, 0.47 mg) in 3 mL of acetonitrile was heated under reflux for 43 hours. After evaporation of the solvent, 5 mL of dichloromethane was added and the mixture was filtrate. Evaporation of the filtrate and a purification by column chromatography on silica gel with $CH_2Cl_2$/ethyl acetate (8/2) and then $CH_2Cl_2$/EtOH (9/1) as eluent gave 185 mg (yield: 85%) of product of molecular formula $C_{18}H_{21}IN_2O_4$. Aspect: orange viscous oil.

NMR Spectrum of the Proton

In $CDCl_3$ at 300 MHz, chemical shifts (ppm) and multiplicity: 9.78 (d, J=6.0 Hz, 1H), 9.64 (s, 1H), 8.89 (d, J=8.1 Hz, 1H), 8.18 (dd, J=6.4 and 7.7 Hz, 1H), 7.72 (d, J=8.5 Hz, 2H), 7.12 (d, J=8.5 Hz, 2H), 6.32 (s, 2H), 4.45 (q, J=7.2 Hz, 2H), 3.07 (s, 3H), 2.97 (s, 3H), 1.42 (t, J=7.2 Hz, 3H).

NMR Spectrum of the Carbon

In $CDCl_3$ at 75 MHz, chemical shifts (ppm): 161.0 (C), 154.4 (C), 153.0 (C), 147.5 (CH), 145.5 (CH), 145.3 (CH), 131.3 (CH), 130.9 (C), 129.0 (C), 128.7 (CH), 123.2 (CH), 63.7 ($2\times CH_2$), 36.8 ($CH_3$), 36.6 ($CH_3$), 14.4 ($CH_3$).

EXAMPLE 81

Inclusion of Compound Described in Example 2 in Hydroxypropyl-beta-cyclodextrin 40 mg (0.13 mmol) of compound described in example 2 and 1.46 g of hydroxypropyl-beta-cyclodextrin (DS 0.58-Mw 1386 g.·$L^{-1}$) were dissolved in 15 mL of dichloromethane and 10 mL of methanol. The limpid mixture was evaporated under reduced pressure at room temperature giving 1.80 g of a pale yellow powder containing 2 wt % of product described in example 2 (mol/mol ratio for the complex "dihydro-compound/beta-cyclodextrine": ⅛). The included molecule is now soluble (10 g·$L^{-1}$) in a mixture of 9 wt % NaCl aqueous solution (80 Vol. %), dimethylsulfoxide (10 Vol. %) and Chremofor EL (10 Vol. %).

NMR Spectrum of the Proton

In $D_2O$ at 300 MHz, chemical shifts (ppm) and multiplicity of characteristic peaks: 7.21 (m, 2H), 6.76 (m, 2H), 4.60-5.30 (HPBCP), 3.40-4.10 (HPBCP), 3.21 (s, 3H), 3.14 (s, 3H), 2.98 (s, 3H), 1.11 (HPBCP).

EXAMPLE 82

Inclusion of Compound Described in Example 67 in Hydroxypropyl-beta-cyclodextrin 61 mg (0.21 mmol) of compound described in example 67 and 1.47 g of hydroxypropyl-beta-cyclodextrin (DS 0.58-Mw 1386 g·$L^{-1}$) were dissolved in 15 mL of dichloromethane and 10 mL of methanol. The limpid mixture was evaporated under reduced pressure at room temperature. The solid obtained was then dissolved in 3 mL of MilliQ water and filtered through filter with 45 micron pore size. The filter was rinsed with 9 mL of MilliQ water. The aqueous solution was then freeze dried giving 2 g of a pale yellow powder containing 4 wt % of product described in example 67 (mol/mol ratio for the complex "dihydro-compound/beta-cyclodextrine": ⅛). The included molecule is now soluble (20 g·$L^{-1}$) in a 9 wt % NaCl aqueous solution.

NMR Spectrum of the Proton

In $D_2O$ at 300 MHz, chemical shifts (ppm) and multiplicity of characteristic peaks: 7.30 (s., 1H), 7.20 (dd, J=7.7 and 8.9 Hz, 1H), 6.74 (m, 2H), 4.60-5.3 (HPBCP), 3.30-4.10 (HPBCP), 3.18 (s, 3H), 3.11 (s, 3H), 2.95 (s, 3H), 1.11 (HPBCP).

Biological Tests: Protocols and Results (Table 2)

Cholinesterase Activity Determination.

Acetylcholinesterase (AChE) activity of both bio precursors and inhibitors was determined by a modified Ellman method ([1] ELLMAN, G. L., COURTNEY, K. D., ANDRES, V., J R. AND FEATHERSTONE, R. M.: A new and rapid colorimetric determination of acetylcholinesterase activity. Biochem. Pharmacol. 7: 88-95, 1961.) using acetylthiocholine iodide as substrate. The assay mixture (Phosphate buffer, pH=7.4, 52 mM, 3 mL) contained 5,5'-dithiobis-2-nitrobenzoic acid (0.5 mM), human erythrocyte membranes as a AChE source and studied ligand at various concentrations. The 10.0 minutes incubation time at room temperature was selected for the enzyme assay after preliminary experiments performed to ensure that the enzyme activity is linear with respect to reaction time and enzyme concentration. The blank was also run under the same conditions and with the same components without the enzyme.

An apparent $IC_{50}$ was determined and expressed by comparison with that of Donepezil ($IC_{50}$=50 nM).

Muscarinic Receptors Binding.

The ability of bio precursors and/or inhibitors to nonselectively bind muscarinic receptors was evaluated with conventional radioligand binding method.

The assay mixture (PBS Buffer, 300 µL), rat striatal membranes as a muscarinic receptors source (1 g/L, 100 µL), unknown compound at various concentrations (50 µL) and $^3$H—N-methylscopolamine as specific radioligand of muscarinic receptors. The 60.0 minutes incubation time at room temperature was selected after preliminary experiments performed to ensure that the equilibrium between studied ligand and radioligand on muscarinic receptors is reached. The reaction was stopped by rapid vacuum filtration through Whatman GF/C filter paper (pre-soaked in a solution of polyethylenimine (0.1%) to reduce binding to filters). Filters were subsequently washed with ice-cold buffer (PBS Buffer, 3×1.5 mL) and placed overnight in 3 mL of Ready-Safe scintillation cocktail (Beckman Coulter, Inc.). Radioactivity was measured using a Wallac liquid scintillation counter. Each experiment was carried out twice in duplicate.

Protein Determination.

Protein concentration was determined by the method of Lowry (Lowry O H, Rosebrough N J, Farr A L, Randall R J (1951) Protein measurement with the folin phenol reagent. *J Biol Chem* 193, 265-275) with bovine serum as the standard.

Acute Toxicity.

The toxicity studies were carried out using female and male Swiss albinos mice (25-35 g). Animals were kept in a temperature-controlled environment (23±2° C.) with a 12 h light-dark cycle and food and water were freely available. The animals were divided into one control group and five treated groups, each group consisting of six animals. The control group received saline and each treated group received the studied ligand in a dose of 1, 3, 10, 30 and 100 mg/kg by intraperitoneal injection. The animals were observed continuously for 3 h, and then they were observed each hour during 72 h after administering the compound in order to observe any changes in general behaviour or other physiological activities. At the end of the experiment, animals were sacrificed by cervical displacement.

Pharmacokinetic.

Monitoring of the Bio Precursor Concentrations in Mouse Plasma by Reversed-Phase High-Performance Liquid Chromatography 1. Apparatus The HPLC system consisted of an LC-10AD Shimadzu pump (Croissy Beaubourg, France), an LC-10 Shimadzu automatic sample injector, and a SPD 10AVP UV detector (Shimadzu, Croissy Beaubourg, France) with an integrator (Shimadzy Class VP data system version 5; Shimadzu, France). The separation was performed on a nucleosil C18 particle size 5 m, 250×4.60 mm (I.D.) column (Touzart & Matignon, Paris, France).

2. Optimal HPLC Conditions

The mobile phasis consisted of 50% acetonitrile in phosphate buffer (25 mM, pH 6.5). The rate of the mobile phase delivery through the HPLC system was 1 ml/min. Compound 67 was monitored at 240 nm with a time constant of 20 ms. The analytical and guard columns and the mobile phase were all maintained at 30° C. Compound 67 in samples (mice plasma) was quantified by comparing the peak height of compound 67 in samples with a standard calibration curve of compound 67 in human plasma provided by EFS (Etablissement Francais du Sang, Bois-Guillaume, France).

3. Preparation of Calibration Standards

A stock solution of compound 67 was prepared by dissolving 0.01 mmol (2.9 mg) in 1 ml of methanol to obtain a final concentration of $10^{-2}$M. Further solutions were obtained by serial dilutions of the stock solution with deionised Milli-Q filter water. Both a 20 l aliquot of a 1000 nM compound 67 solution and a 20 l aliquot of a 10,000 nM of 5,7-dimethoxy-3-cyanoquinoline as internal standard were injected into the HPLC system to determine the retention times under the experimental chromatographic conditions (8.4 and 9.8 min respectively). Standard plasmatic concentrations of compound 67 ranged between 25 and 1000 nM. The calibration curves were obtained by linear regression: the ratio of compound 67 peak height was plotted to 5,7-dimethoxy-3-cyanoquinoline peak height was plotted vs. compound 67 concentration in nM. The suitability of the calibration model was confirmed by back-calculating the concentration of calibration standards.

To 200 μL of plasma (human or mice), 100 μL of phosphate buffer (50 mM, pH 6) and internal standard (100 μL, $10^{-5}$M) were added. This sample was extracted by dichloromethane (2×200 μL), the solvent was collected and evaporated to dryness under nitrogen at room temperature. The residue was dissolved in methanol (40 μL) and ready to inject in HPLC system.

4. Method Validation

Plasmas with 33, 66, 333, and 666 nM of compound 67, prepared for quality control, were for extra-low, low, medium, and high-level plasmatic concentrations, respectively. The precision and accuracy of the method were evaluated by testing five replicates of four plasmatic concentrations of compound 67 for the within-day. The precision and accuracy were defined as the relative standard deviation (RSD) and as the error from the theoretical nominal concentration, respectively. The linearity data were obtained by means of calibration curves (n=5). The limit of quantification (LOQ) was defined as the lowest concentration at which the precision expressed by the RSD was lower than 15% and the accuracy expressed by the relative difference of the measured and true value was also lower than 15%.

5. Determination of Half-Life and Distribution Volume of Compound 67 (IP-10 mg/kg) in Mice The pharmacokinetic study was carried out using female and male Swiss albinos mice (25-35 g). Animals were kept in a temperature-controlled environment (23±2° C.) with a 12 h light-dark cycle and food and water were freely available. The animals were divided into one control group and four treated groups, each group consisting of six animals. The control group received saline and each treated group received compound 67 in a dose of 10 mg/kg by intraperitoneal injection of compound 82 and was sacrificed by cervical displacement at various times (15, 30, 60, 120 min) and blood was collected. The blood was centrifuged at 3000 RPM for 10 min, the plasma was collected and keep at −30° C. until HPLC analysis. In this test, a pharmaceutical composition was prepared for injection.

This pharmaceutical composition contained:

| | |
|---|---|
| the compound of example 67: | 500 mg |
| a sterile aqueous excipient: | 10 ml. |

Plasmatic half-life time: $T_{1/2}$=14 min.

Apparent volume of distribution: $V_d$=42 L/kg $C_0$: 806 nM

TABLE 2

| Example | compound | Inhibition of human acetylcholinesterase (apparent $IC_{50}$) | Displacement of [$^3$H] N-methylscopolamine from muscarinic receptors |
|---|---|---|---|
| 1 | 1D | 0.5 μM | 0% at $10^{-5}$ M |
| 1 | 1E | No inhibition until solubility limit | 0% at $10^{-5}$ M |
| 2 | 2E | 7 nM | 0% at $10^{-5}$ M |
| 2 | 2F | No inhibition until solubility limit | 0% at $10^{-5}$ M |
| 67 | 67E | 110 nM | 0% at $10^{-5}$ M |
| 67 | 67F | No inhibition until solubility limit | 0% at $10^{-5}$ M |
| 68 | 68D | 29 nM | 0% à $10^{-5}$ M |
| 68 | 68E | No inhibition until solubility limit | 0% at $10^{-5}$ M |
| 69 | 69D | 15 nM | 0% à $10^{-5}$ M |
| 70 | 70D | 860 nM | 0% à $10^{-5}$ M |
| 70 | 70E | No inhibition until solubility limit | 0% à $10^{-5}$ M |
| 71 | 71B | 50 nM | Not determined |
| 72 | 72B | 5 μM | Not determined |
| 73 | 73D | >10 μM | Not determined |
| 74 | 74E | 1.4 μM | Not determined |
| 75 | 75B | >10 μM | Not determined |
| 76 | 76B | 6 μM | Not determined |
| 76 | 76C | No inhibition until solubility limit | Not determined |
| 77 | 77C | 8 μM | Not determined |
| 78 | 78C | 50 μM | 20% at $10^{-5}$ M |
| 78 | 78D | No inhibition until solubility limit | 25% at $10^{-5}$ M |
| 79 | 79D | 80 μM | Not determined |
| 80 | 80C | 227 nM | Not determined |

The invention claimed is:

1. A compound of formula G

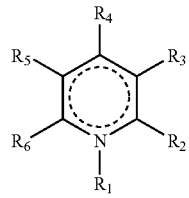

or a pharmaceutical salt or a stereoisomer of G;
wherein:

the dotted circle line represents one double bond between $CR_5$-$CR_6$, and another double bond between either $CR_2$-$CR_3$ or $CR_3$-$CR_4$; and a) except as provided in c) below, $R_1$, $R_2$, $R_3$, and $R_4$, which may be identical or different, are each selected from the group consisting of hydrogen, OH, ($C_1$-$C_8$) alkyl, aryl, heteroaryl, ($C_1$-$C_8$) alkylaryl, aryl($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z and $Z_1$, and b) $R_5$ and $R_6$ taken together with the carbon atoms to which $R_5$ and $R_6$ are attached form a ring selected from the group consisting of a 6-membered aromatic ring and a 5- or 6-membered heterocyclic ring, the ring being optionally substituted by one or more group, identical or different, each selected from the group consisting of OH, ($C_1$-$C_8$) alkyl, aryl, heteroaryl, ($C_1$-$C_8$) alkylaryl, aryl ($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z and, $Z_1$; and c) at least one group among $R_2$ and $R_3$ is an electron withdrawing group selected from the group consisting of COOR, COSR, CONRR', CN, COR, $CF_3$, SOR, $SO_2R$, SONRR', $SO_2NRR'$, $NO_2$, halogen and heteroaryl, wherein R, and R' are each a group selected from the group consisting of H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, thioalkyl, thioalkoxyalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl and halogenoheteroaryl, or R and R' taken together with the nitrogen atom to which they are attached form an heterocyclic ring of at least 3 members optionally substituted by one or more groups being as defined for $R_2$, or R and R' taken together with the nitrogen atom to which they are attached form a fused polyheterocyclic system, optionally tetrahydroisoquinoline, indoline or isoindoline, optionally substituted by one or more group being as defined for $R_2$;

and wherein

Z is a group defined by formula -(L)$_m$-$Z_1$, wherein L is selected from the group consisting of ($C_1$-$C_8$) alkyl, aryl, heteroaryl, phenyl, ($C_1$-$C_8$) alkylaryl and aryl($C_1$-$C_8$) alkyl;

$Z_1$ is defined by formula

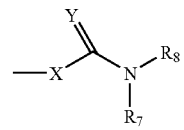

wherein X and Y are each selected from the group consisting of O and S; wherein $R_7$ and $R_8$, which may be identical or different, are each selected from the group consisting of hydrogen, ($C_1$-$C_8$) alkyl, aryl, heteroaryl, ($C_1$-$C_8$) alkylaryl, phenyl, cyclopropyl and $(CH_2)_n$—COOH; and wherein n and m are each an integer $\geq 1$, optionally m is comprised between 1 and 4 and n is comprised between 1 and 6;

and provided that at least one of $R_1$, $R_2$, $R_3$ and $R_4$ is Z or $Z_1$ and that $R_1$ is not H or $Z_1$.

2. A compound according to claim 1 of formula G$^+$

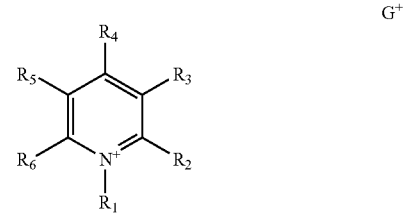

optionally under an ammonium salt form G$^+$ W$^-$ wherein W is the leaving group of an alkylating agent of formula $R_1$—W or under a pharmacologically acceptable salt.

3. A compound according to claim 1 of formula G3a, G3b or G3$^{30}$

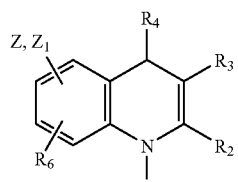

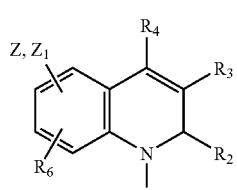

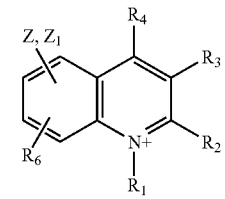

wherein, $R_6$' is selected from the group consisting of hydrogen, OH, ($C_1$-$C_8$) alkyl, aryl, heteroaryl, ($C_1$-$C_8$) alkylaryl, aryl ($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z and $Z_1$.

4. A compound according to claim 3 of formula G3a or G3b or G3+ wherein
   a) $R_2$ and $R_3$, or $R_3$ and $R_4$, taken together with the carbon atoms to which they are attached form a 5 to 7 membered heterocycle; or
   b) $R_1$ and $R_2$, taken together with the atoms to which they are attached form a 5 to 7 membered heterocycle, or a 5 to 7 membered heterocycle substituted by one or more groups being as defined for $R_2$.

5. A compound according to claim 3 of formula G3a or G3+ wherein
   $R_1$ is ($C_1$-$C_4$) alkyl, $R_2$ is H or ($C_1$-$C_4$) alkyl, $R_3$ is a said electron withdrawing group, $R_4$ and $R_6'$ are each H and $Z_1$ is $OCONR_7R_8$.

6. A compound according to claim 1, wherein $R_3$ is a heteroaryl group selected from the group consisting of oxazolinyl, thiazolinyl, oxazolyl, thiazolyl, triazolyl and tetrazolyl, and any of the foregoing optionally substituted by one or more groups being as defined for $R_2$.

7. A compound according to claim 1 wherein
   $R_1$ is selected from the group consisting of ($C_1$-$C_4$) alkyl and $-(L)_m$-$Z_1$ wherein L is aryl and m is 1;
   $R_2$ is selected from the group consisting of H, ($C_1$-$C_4$) alkyl, phenyl and aryl; and
   $Z_1$ is

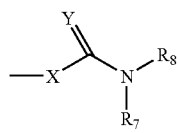

wherein X and Y are each O, or X is O and Y is S, or X is S and Y is O; $R_7$ and $R_8$, which may be identical or different, are each selected from the group consisting of hydrogen, ($C_1$-$C_4$) alkyl, ($C_1$-$C_4$) alkylaryl and phenyl.

8. A compound according to claim 1 comprising at least one radical C=Y, Y being O or S, and an oxidable and non protonable nitrogen atom N wherein the distance d between the one carbon atom of the radical group C=Y and the nitrogen atom, when oxidized, is comprised between 0.3 and 0.8 nanometers.

9. A compound according to claim 1, selected from the group consisting of:
Ethyl 1-methyl-7-(N,N-dimethylcarbamate)-1,4-dihydroquinoline-3-carboxylate;
Ethyl 1-methyl-5-(N,N-dimethylcarbamate)-1,4-dihydroquinoline-3-carboxylate;
Ethyl 1-methyl-5,7-di(N,N-dimethylcarbamate)-1,4-dihydroquinoline-3-carboxylate;
Ethyl 1-methyl-5,8-di(N,N-dimethylcarbamate)-1,4-dihydroquinoline-3-carboxylate;
Ethyl 1-methyl-5-(N,N-dimethylthiocarbamate)-1,4-dihydro-5-O-quinoline-3-carboxylate;
Ethyl 1-methyl-5-(N,N-dimethylthiocarbamate)-1,4-dihydro-5-S-quinoline-3-carboxylate;
1-Methyl-5-(N,N-dimethylcarbamate)-3-(N,N-diethylearboxamido)-1,4-dihydroquinoline;
1-Methyl-7-(N,N-dimethylcarbamate)-3-(4,5-dihydro-4,4-dimethyl-2-oxazolyl)-1,4-dihydroquinoline;
1-Methyl-5-(N,N-dimethylcarbamate)-3-trifluoromethyl-1,4-dihydroquinoline;
(+/−)-1-Methyl-3-(4-methylphenylsulfinyl)-5-(N,N-dimethylcarbamate)-1,4-quinoline;
1-Methyl-3-(4-methylphenylsulfonyl)-5-(N,N-dimethylcarbamate)-1,4-dihydroquinoline;
1-Methyl-5-(N,N-dimethylcarbamate)-3-(N-phenylsulfomanide)-1,4-dihydroquinoline;
1-Methyl-6,7-di(N,N-dimethylcarbamate)-3-nitro-1,4-dihydroquinoline;
Ethyl 1-methyl-2-phenyl-6,7-di(N,N-dimethylcarbamate)-1,4-dihydroquinoline-3-carboxylate;
Ethyl 1,2,4-trimethyl-7-(N,N-dimethylcarbamate)-1,4-dihydroquinoline-3-carboxylate;
Ethyl 1-[2-(N,N-dimethylcarbamate)benzyl]-1,4-dihydroquinoline-3-carboxylate;
1-[2-(N,N-dimethylcarbamate)benzyl]-1,4-dihydro-3-(dimethylcarbamoyl)quinoline;
1-[2-(N,N-dimethylcarbamate)benzyl]-1,4-dihydro-3-(4,5-dihydro-4,4-dimethyl-2-oxazolyl)quinoline;
N,N-Dimethyl-1-[2-(N,N-dimethylcarbamate)benzyl]-1,4-dihydroquinoline-3-sulfonamide;
1-[2-(N,N-dimethylcarbamate)benzyl]-3-(trifluoromethyl)-1,4-dihydroquinoline;
Ethyl 1-methyl-2-[2-(N,N-dimethylcarbamate)phenyl]-1,4-dihydroquinoline-3-carboxylate;
Ethyl 1-methyl-8-[2-(N,N-dimethylcarbamate)phenyl]-1,4-dihydroquinoline-3-carboxylate;
Ethyl 1-methyl-7-(N,N-dimethylcarbamate)-1,2-dihydroquinoline-3-carboxylate;
Ethyl 1-methyl-5-(N,N-dimethylthiocarbamate)-1,2-dihydro-5-S-quinoline-3-carboxylate;
1-Methyl 5-(N,N-dimethylcarbamate)-3-(4,5-dihydro-4,4-dimethyl-2-oxazolyl)1,2-dihydroquinoline;
Methyl 1-methyl-5-(N,N-dimethylcarbamate)-1,4-dihydroquinoline-3-carboxylate;
1-Methyl-3-(N-methylcarboxamido)-5-(N,N-dimethylcarbamate)-1,4-dihydroquinoline;
[3-(N,N-methylcarboxamido)-5-(N,N-dimethylcarbamate)]-1,4-dihydroquinoline or 1,2-dihydroquinoline;
Morpholine 4-[1-methyl-5-(N,N-dimethylcarbamate)-1,4-dihydroquinolyl-3-carbonyl];
[Methyl 1-methyl-5,7-bis(N,N-dimethylcarbamate)-3-carboxylate]-1,4-dihydroquinoline or 1,2-dihydroquinoline;
[Methyl 1-methyl-8-(N,N-dimethylcarbamate)-3-carboxylate]-1,4-dihydroquinoline or 1,2-dihydroquinoline;
Methyl 1-methyl-5-(N-ethylcarbamate)-1,4-dihydroquinoline-3-carboxylate;
[Ethyl 1-methyl-8-(N,N-dimethylcarbamate)-3-carboxylate]-1,4-dihydroquinoline or 1,2-dihydroquinoline;
1-Methyl-3-(N-propylcarboxamido)-7-(N,N-dimethylcarbamate)-1,4-dihydroquinoline;
and the corresponding ammonium form of any of the foregoing.

10. An inclusion complex comprising the compound according to claim 1 and a beta-cyclodextrine.

11. A pharmaceutical composition comprising at least one compound according to claim 1 and a pharmacologically acceptable carrier.

12. A compound according to claim 4, wherein the 5 to 7 membered heterocycle, is selected from the group consisting of lactame, N-alkyllactame, N-aryllactame, N-heteroaryllactame, lactone and thiolactone.

13. An inclusion complex according to claim 10, wherein the beta-cyclodextrine is hydroxypropyl-betacyclodextrine.

14. A compound of formula G'3;

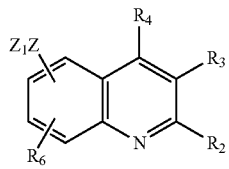

wherein;

a) except as provided in c) below, $R_2$, $R_3$ and $R_4$, which may be identical or different, are each selected from the group consisting of hydrogen, OH, ($C_1$-$C_8$) alkyl, aryl, heteroaryl, ($C_1$-$C_8$) alkylaryl, aryl($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z and $Z_1$; and b) $R_6$ is selected from the group consisting of OH, ($C_1$-$C_8$) alkyl, aryl, heteroaryl, ($C_1$-$C_8$) alkylaryl, aryl ($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z, and $Z_1$; and c) at least one group among $R_2$, and $R_3$ is an electron withdrawing group selected from the group consisting of COOR, COSR, CONRR', CN, COR, $CF_3$, SOR, $SO_2R$, SONRR', $SO_2NRR'$, $NO_2$, halogen and heteroaryl, wherein R, and R' are each a group selected from the group consisting of H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, thioalkyl, thioalkoxyalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl and halogenoheteroaryl, or R and R' taken together with the nitrogen atom to which they are attached form an heterocyclic ring of at least 3 members, optionally substituted by one or more groups being as defined for $R_2$, or R and R' taken together with the nitrogen atom to which they are attached form a fused polyheterocyclic system, optionally tetrahydroisoquinoline, indoline or isoindoline, optionally substituted by one or more group being as defined for $R_2$;

and wherein

Z is a group defined by formula $-(L)_m-Z_1$, wherein L is selected from the group consisting of ($C_1$-$C_8$) alkyl, aryl, heteroaryl, phenyl, ($C_1$-$C_8$) alkylaryl and aryl($C_1$-$C_8$) alkyl;

$Z_1$ is defined by formula

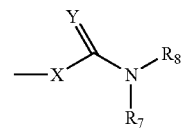

wherein X and Y are each, selected from the group consisting of O and S; wherein $R_7$ and $R_8$, which may be identical or different, are each selected from the group consisting of hydrogen, ($C_1$-$C_8$) alkyl, aryl, heteroaryl, ($C_1$-$C_8$) alkylaryl, phenyl, cyclopropyl and$(CH_2)_n$—COOH; and wherein n and m are each an integer $\geq 1$, optionally m is comprised between 1 and 4 and n is comprised between 1 and 6;

and provided that at least one of $R_2$, $R_3$ and $R_4$ is Z or $Z_1$.

15. A compound according to claim 14, wherein R and R' taken together with the nitrogen atom to which they are attached form a 5 or 6 membered heterocyclic ring.

16. A compound according to claim 1, wherein R and R' taken together with the nitrogen atom to which they are attached form a 5 or 6 membered heterocyclic ring.

17. A compound according to claim 3 wherein $R_3$ is a said electron withdrawing group.

18. A compound according to claim 1 of the formula G3+

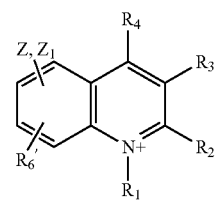

wherein, $R_6'$ is selected from the group consisting of hydrogen, OH, ($C_1$-$C_8$) alkyl, aryl, heteroaryl, ($C_1$-$C_8$) alkylaryl, aryl ($C_1$-$C_8$) alkyl, alkoxy, hydroxy ($C_1$-$C_8$) alkyl, alkoxy ($C_1$-$C_8$) alkyl, phenyl, $(CH_2)_n$—COOH, Z and $Z_1$.

* * * * *

UNITED STATES PATENT AND TRADEMARK OFFICE
CERTIFICATE OF CORRECTION

PATENT NO. : 7,977,354 B2  Page 1 of 1
APPLICATION NO. : 11/909911
DATED : July 12, 2011
INVENTOR(S) : Marsais et al.

It is certified that error appears in the above-identified patent and that said Letters Patent is hereby corrected as shown below:

Column 80, line 29, delete "chermical", and insert therefor --chemical--.
Column 108, line 37, delete "G3 30", and insert therefor --G3+--.

Signed and Sealed this
Twenty-seventh Day of September, 2011

David J. Kappos
*Director of the United States Patent and Trademark Office*